(12) United States Patent
Inturrisi et al.

(10) Patent No.: US 8,951,979 B2
(45) Date of Patent: Feb. 10, 2015

(54) PAIN TREATMENT USING ERK2 INHIBITORS

(75) Inventors: Charles E. Inturrisi, Torrington, CT (US); Qinghao Xu, New York, NY (US); Sandra M. Garraway, Brooklyn, NY (US)

(73) Assignee: Cornell University, Ithaca, NY (US)

(*) Notice: Subject to any disclaimer, the term of this patent is extended or adjusted under 35 U.S.C. 154(b) by 186 days.

(21) Appl. No.: 12/997,836

(22) PCT Filed: Jun. 12, 2009

(86) PCT No.: PCT/US2009/003523
§ 371 (c)(1),
(2), (4) Date: Dec. 13, 2010

(87) PCT Pub. No.: WO2009/151620
PCT Pub. Date: Dec. 17, 2009

(65) Prior Publication Data
US 2011/0293628 A1     Dec. 1, 2011

Related U.S. Application Data

(60) Provisional application No. 61/061,254, filed on Jun. 13, 2008.

(51) Int. Cl.
*C12N 15/11* (2006.01)
*A61K 31/506* (2006.01)
*C12N 15/113* (2010.01)

(52) U.S. Cl.
CPC ........ *A61K 31/506* (2013.01); *C12N 15/1137* (2013.01); *C12Y 207/11024* (2013.01); *C12N 2310/11* (2013.01); *C12N 2310/14* (2013.01); *C12N 2799/025* (2013.01)
USPC ...................................................... 514/44 A

(58) Field of Classification Search
USPC ....................................................... 514/44 A
See application file for complete search history.

(56) References Cited

U.S. PATENT DOCUMENTS

| | | | |
|---|---|---|---|
| 6,007,991 A * | 12/1999 | Sivaraman et al. | 435/6.16 |
| 6,271,210 B1 * | 8/2001 | Sivaraman et al. | 514/44 A |
| 2004/0258671 A1 * | 12/2004 | Watkins | 424/93.21 |
| 2005/0019927 A1 * | 1/2005 | Hildinger et al. | 435/456 |
| 2005/0054706 A1 * | 3/2005 | Arkinstall et al. | 514/396 |
| 2005/0107325 A1 * | 5/2005 | Manoharan et al. | 514/44 |
| 2005/0239731 A1 * | 10/2005 | McSwiggen et al. | 514/44 |
| 2006/0189639 A1 * | 8/2006 | Stewart et al. | 514/267 |

FOREIGN PATENT DOCUMENTS

| | | |
|---|---|---|
| WO | PCT/US03/002510 | 9/2003 |
| WO | WO-03072590 A1 | 9/2003 |
| WO | WO2008109358 A1 * | 9/2008 |
| WO | WO-2009151620 A2 | 12/2009 |
| WO | WO-2009151620 A9 | 4/2010 |

OTHER PUBLICATIONS

Ohori et al., Naunyn-Schmiederberg's Ach Pharmacol (2007) 374: 311-316.*
Ma et al. Expert Opin. Ther. Targets 2005, 9:699-713.*
Ji RR Curr. Opin. Investig. Drug 2004, 71-5.*
Cui et al. (Molecular Pain 4:17, pp. 1-11, Apr. 2008).*
Adwanikar et al. Pain 111 2004 125-135.*
Guo et al. BMC Neuroscience 8:53, pp. 1-14, 2007.*
Ji et al. HEP 2006 177:359-389.*
Zhuang et al. Pain 114 2005, 149-159.*
Yuan et al. (Nucleic Acid Res. 32: W130-134, 2004).*
U.S. Appl. No. 11/083,583, Patent Board Decision-Examiner affirmed, mailed on Nov. 28, 2012, pp. 1-11.*
"International Application Serial No. PCT/US2009/003523, Search Report mailed Feb. 2, 2010", 7 Pgs.
"International Application Serial No. PCT/US2009/003523, Written Opinion mailed Feb. 2, 2010", 4 Pgs.
Garraway, S. M., et al., "Design and Evaluation of Small Interfering RNAs That Target Expression of the N-Methyl-D-aspartate Receptor NR1 Subunit Gene in the Spinal Cord Dorsal Horn", The Journal of Pharmacology and Experimental Therapeutics, 322(3), 982-988, 2007.
Zampieri, C. A., et al., "The ERK Mitogen-Activated Protein Kinase Pathway Contributes to Ebola Virus Glycoprotein-Induced Cytotoxicity", Journal of Virology, 81(3), (Feb. 2007), 1230-1240.
"International Application Serial No. PCT/US2009/003523, International Prelimianry Report on Patentability mailed Dec. 23, 2010", 5 pgs.
Alter, Benedict J., et al., "Genetic Targeting of ERK1 Suggests a Predominant Role for ERK2 in Murine Pain Models", The Journal of Neuroscience, 30(34), (2010), 11537-11547.

* cited by examiner

*Primary Examiner* — Brian Whiteman
(74) *Attorney, Agent, or Firm* — Schwegman Lundberg & Woessner, P.A.

(57) ABSTRACT

This application describes methods and compositions for reducing, inhibiting and/or treating pain that involve use of ERK2 inhibitors.

18 Claims, 20 Drawing Sheets

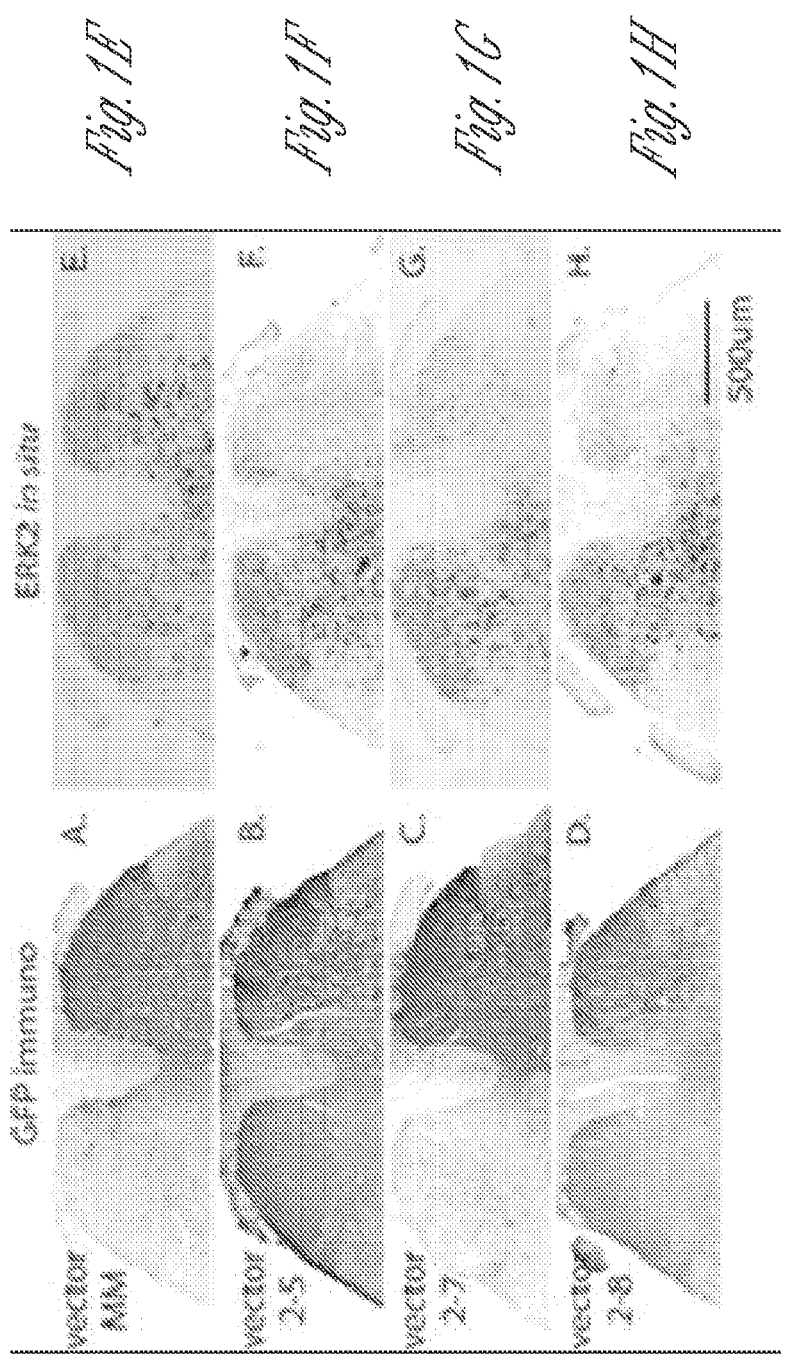

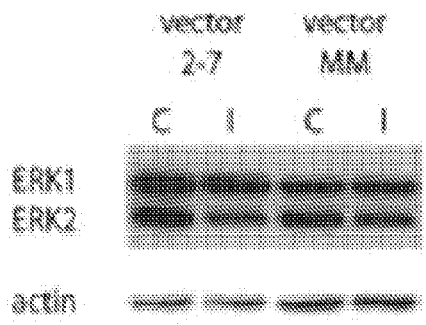 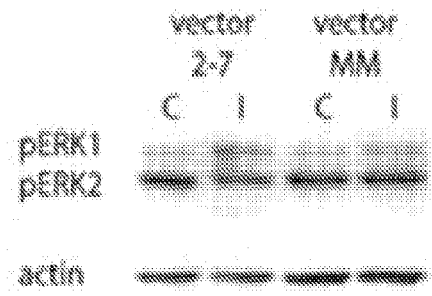
Fig. 2A  Fig. 2D
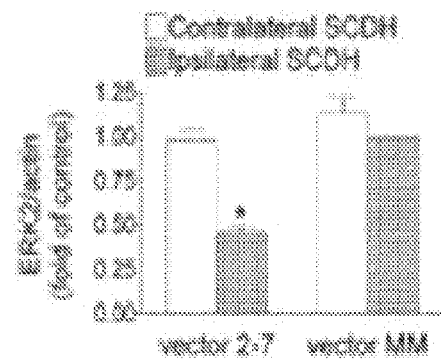 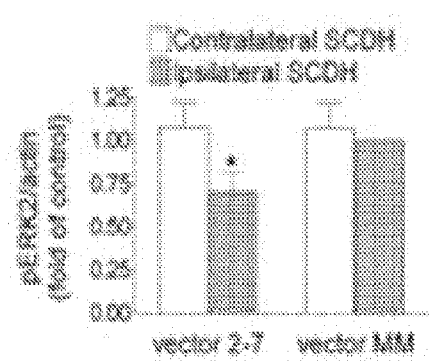
Fig. 2B  Fig. 2E
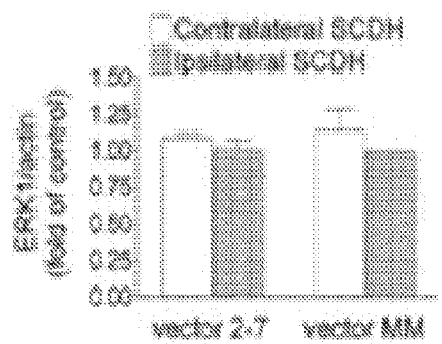 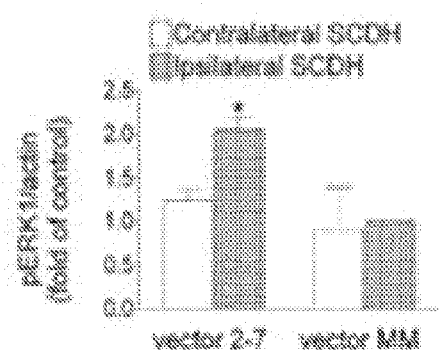
Fig. 2C  Fig. 2F

Fig.2G1
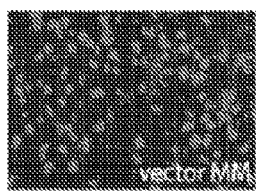
Fig.2G4
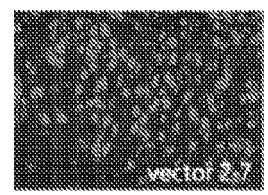
Fig.2G7
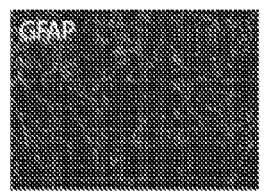
Fig.2G2
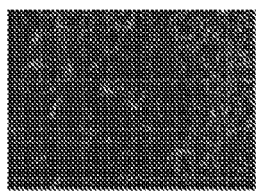
Fig.2G5
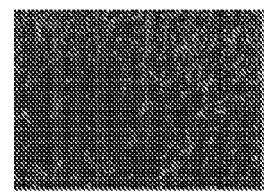
Fig.2G8
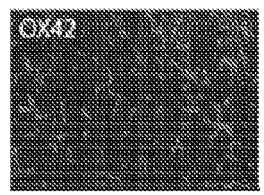
Fig.2G3
Fig.2G6
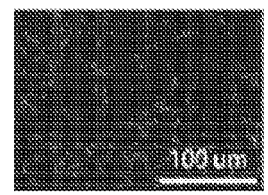
Fig.2G9

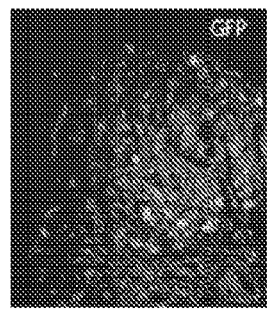
*Fig.3G1*
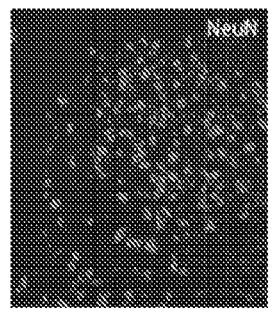
*Fig.3G4*
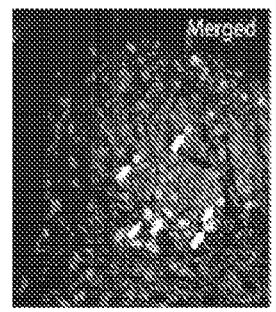
*Fig.3G7*
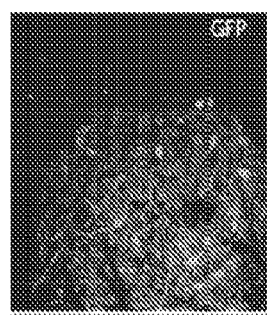
*Fig.3G2*
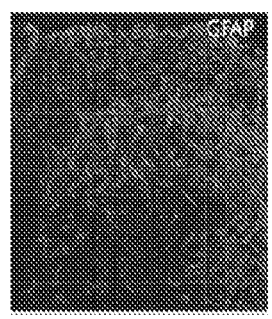
*Fig.3G5*
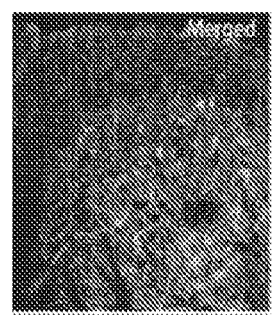
*Fig.3G8*
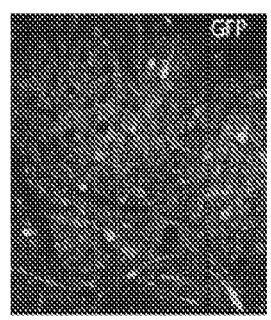
*Fig.3G3*
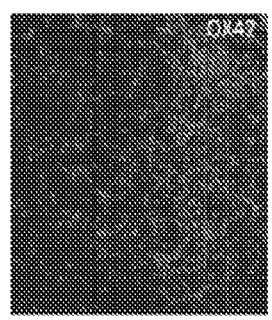
*Fig.3G6*
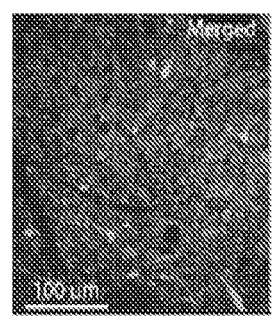
*Fig.3G9*

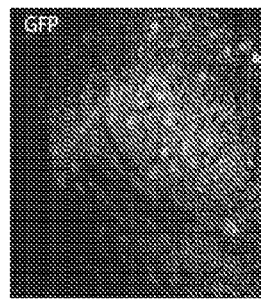 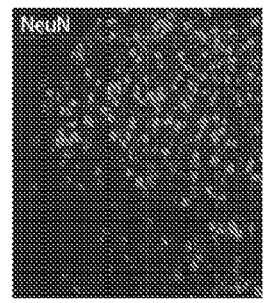 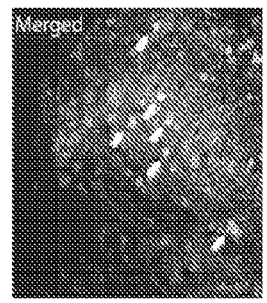
*Fig.3H1*  *Fig.3H4*  *Fig.3H7*
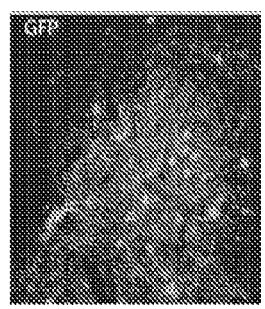 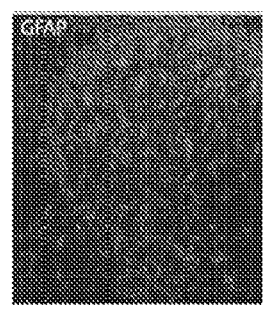 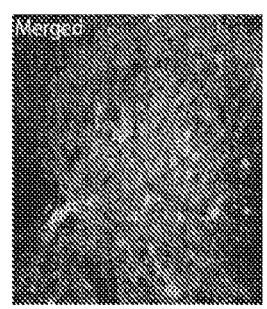
*Fig.3H2*  *Fig.3H5*  *Fig.3H8*
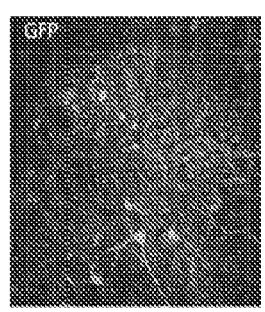 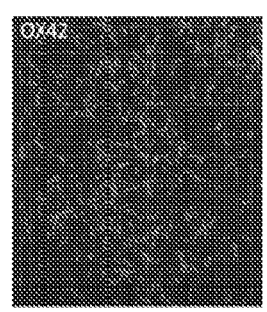 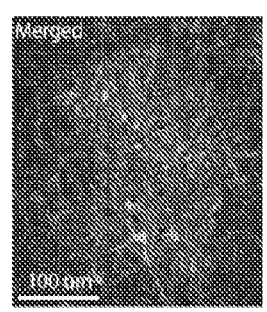
*Fig.3H3*  *Fig.3H6*  *Fig.3H9*

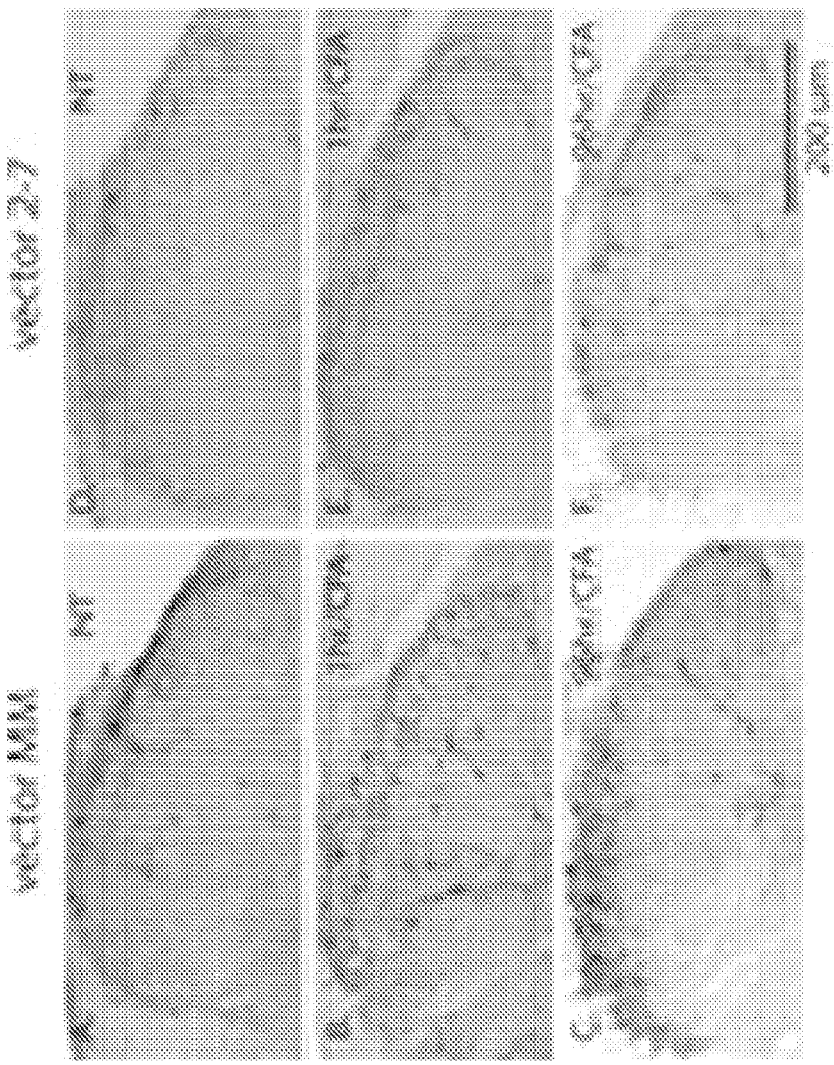

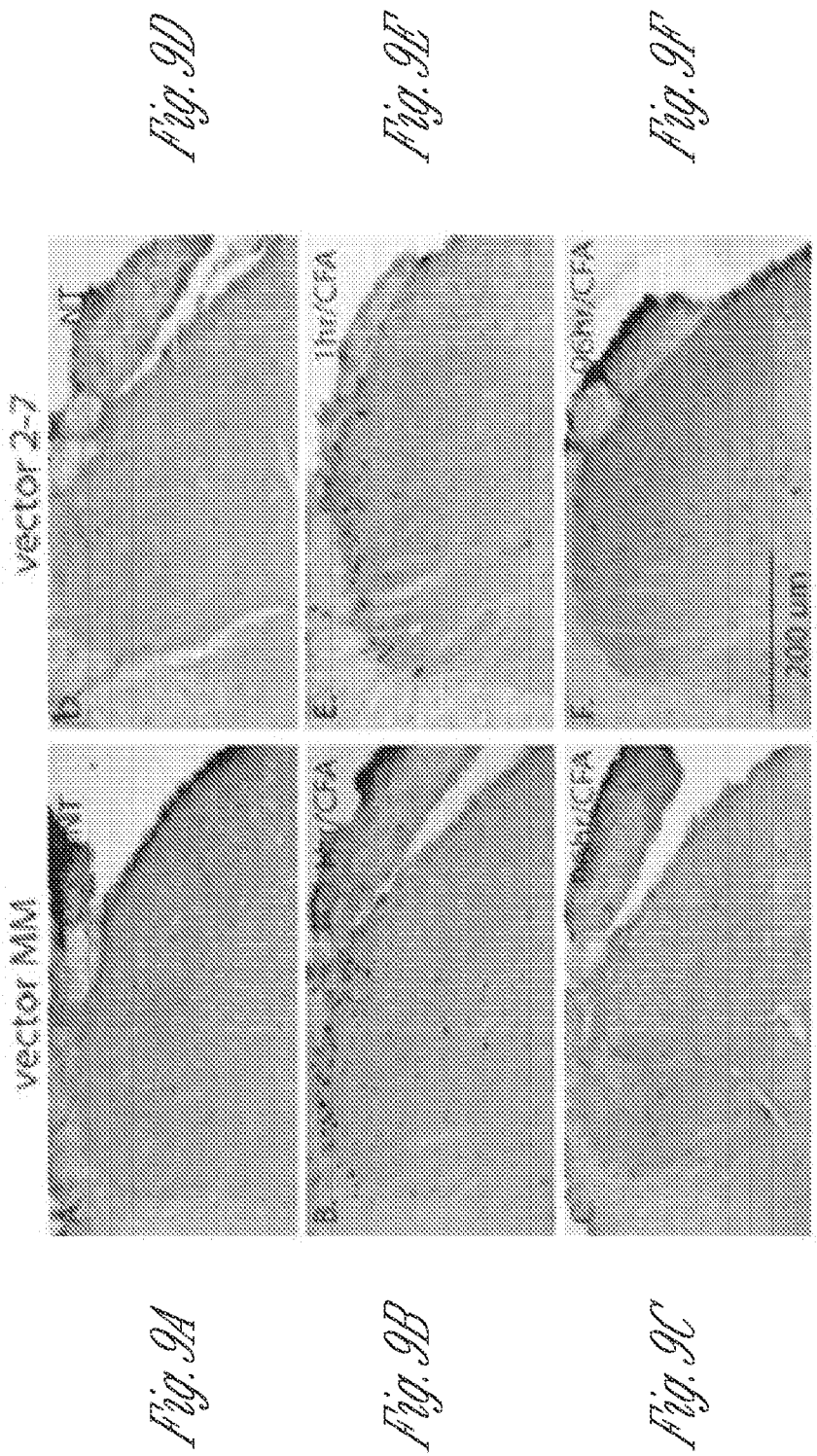

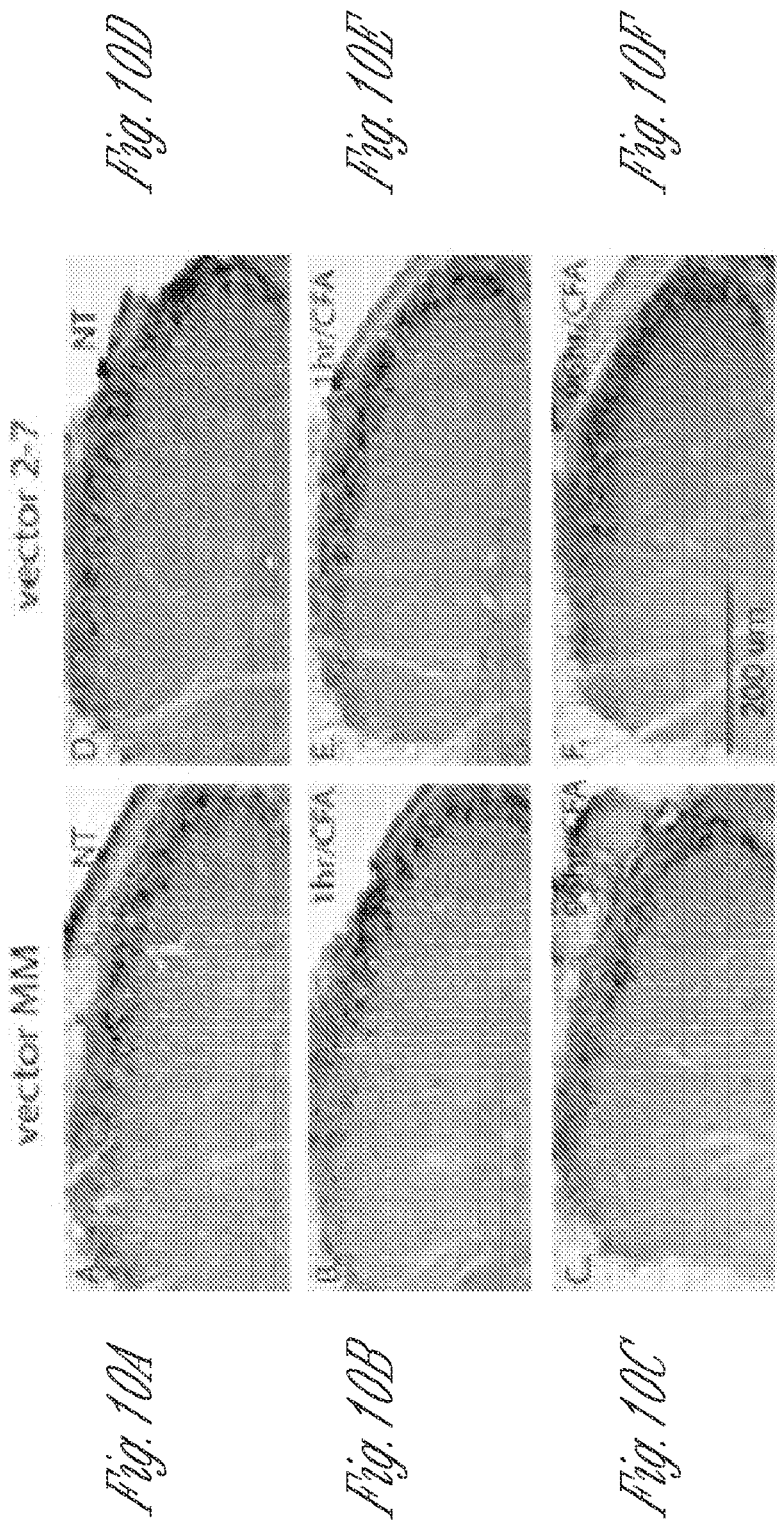

SEQUENCE LISTING

<160> NUMBER OF SEQ ID NOS: 786

<210> SEQ ID NO 1
<211> LENGTH: 360
<212> TYPE: PRT
<213> ORGANISM: Homo sapiens

<400> SEQUENCE: 1

Met Ala Ala Ala Ala Ala Ala Gly Ala Gly Pro Glu Met Val Arg Gly
 1               5                  10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

```
Asp His Asp His Thr Gly Phe Leu Thr Glu Tyr Val Ala Thr Arg Trp
                180                 185                 190

Tyr Arg Ala Pro Glu Ile Met Leu Asn Ser Lys Gly Tyr Thr Lys Ser
            195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
                260                 265                 270

Val Pro Trp Asn Arg Leu Phe Pro Asn Ala Asp Ser Lys Ala Leu Asp
            275                 280                 285

Leu Leu Asp Lys Met Leu Thr Phe Asn Pro His Lys Arg Ile Glu Val
290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
                340                 345                 350

Arg Phe Gln Pro Gly Tyr Arg Ser
                355                 360

<210> SEQ ID NO 2
<211> LENGTH: 1499
<212> TYPE: DNA
<213> ORGANISM: Homo sapiens

<400> SEQUENCE: 2
gcccctccct ccgcccgccc gccggcccgc ccgtcagtct ggcaggcagg caggcaatcg      60
gtccgagtgg ctgtcggctc ttcagctctc ccgctcggcg tcttccttcc tcctcccggt     120
cagcgtcggc ggctgcaccg gcggcggcgc agtccctgcg ggaggggcga caagagctga     180
gcggcggccg ccgagcgtcg agctcagcgc ggcggaggcg gcggcggccc ggcagccaac     240
atggcggcgc cggcggcggc gggcgcgggc ccggagatgg tccgcgggca ggtgttcgac     300
gtggggccgc gctacaccaa cctctcgtac atcggcgagg gcgcctacgg catggtgtgc     360
tctgcttatg ataatgtcaa caaagttcga gtagctatca gaaaatcagc cccctttgag     420
caccagacct actgccagag aaccctgagg gagataaaaa tcttactgcg cttcagacat     480
gagaacatca ttggaatcaa tgacattatt cgagcaccaa ccatcgagca aatgaaagat     540
gtatatatag tacaggacct catggaaaca gatctttaca agctcttgaa gacacaacac     600
ctcagcaatg accatatctg ctattttctc taccagatcc tcagagggtt aaaatatatc     660
cattcagcta acgttctgca ccgtgacctc aagccttcca acctgctgct caacaccacc     720
tgtgatctca gatctgtga ctttggcctg gcccgtgttg cagatccaga ccatgatcac     780
acagggttcc tgacagaata tgtggccaca cgttggtaca gggctccaga aattatgttg     840
aattccaagg gctacaccaa gtccattgat atttggtctg taggctgcat tctggcagaa     900
atgctttcta caggcccat cttccaggg aagcattatc ttgaccagct gaaccacatt     960
ttgggtattc ttggatcccc atcacaagaa gacctgaatt gtataataaa tttaaaagct    1020
```

-continued

```
aggaactatt tgctttctct tccacacaaa ataaggtgc catggaacag gctgttccca    1080
aatgctgact ccaaagctct ggacttattg gacaaaatgt tgacattcaa cccacacaag    1140
aggattgaag tagaacaggc tctggcccac ccatatctgg agcagtatta cgacccgagt    1200
gacgagccca tcgccgaagc accattcaag ttcgacatgg aattggatga cttgcctaag    1260
gaaaagctca agaactaat ttttgaagag actgctagat tccagccagg atacagatct    1320
taaatttgtc aggtacctgg agtttaatac agtgagctct agcaagggag gcgctgcctt    1380
ttgtttctag aatattatgt tcctcaaggt ccattatttt gtattctttt ccaagctcct    1440
tattggaagg tatttttta aatttagaat taaaaattat ttagaaagtt acatataaa     1499
```

<210> SEQ ID NO 3
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 3
gcaggagcuu guggaaauau u                                              21

<210> SEQ ID NO 4
<211> LENGTH: 23
<212> TYPE: DNA
<213> ORGANISM: Homo sapiens

<400> SEQUENCE: 4
gagcaggagc ttgtggaaat acc                                            23

<210> SEQ ID NO 5
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 5
uauuuccaca agcuccugcu u                                              21

<210> SEQ ID NO 6
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 6
gcugcauucu ggcagaaauu u                                              21

<210> SEQ ID NO 7
<211> LENGTH: 23
<212> TYPE: DNA
<213> ORGANISM: Homo sapiens

<400> SEQUENCE: 7
aggctgcatt ctggcagaaa tgc                                            23

<210> SEQ ID NO 8
<211> LENGTH: 21
<212> TYPE: RNA
<213> ORGANISM: Artificial Sequence
<220> FEATURE:
<223> OTHER INFORMATION: a synthetic siRNA sequence

```
<400> SEQUENCE: 8
auuucugcca gaaugcagcu u                                              21

<210> SEQ ID NO 9
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 9
gugcucugcu uaugauaauu u                                              21

<210> SEQ ID NO 10
<211> LENGTH: 23
<212> TYPE: DNA
<213> ORGANISM: Homo sapiens

<400> SEQUENCE: 10
gtgtgctctg cttatgataa tgt                                            23

<210> SEQ ID NO 11
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 11
auuaucauaa gcagagcacu u                                              21

<210> SEQ ID NO 12
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 12
cgugcaugua uaguuuaauu u                                              21

<210> SEQ ID NO 13
<211> LENGTH: 23
<212> TYPE: DNA
<213> ORGANISM: Homo sapiens

<400> SEQUENCE: 13
accgtgcatg tatagtttaa ttg                                            23

<210> SEQ ID NO 14
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 14
auuaaacuau acaugcacgu u                                              21

<210> SEQ ID NO 15
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 15
guccucaagu acucaaauau u                                              21

<210> SEQ ID NO 16
<211> LENGTH: 23
<212> TYPE: DNA
<213> ORGANISM: Homo sapiens

<400> SEQUENCE: 16
ctgtcctcaa gtactcaaat att                                            23

<210> SEQ ID NO 17
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 17
uauuugagua cuugaggacu u                                              21

<210> SEQ ID NO 18
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 18
ccgugcaugu auaguuuaau u                                              21

<210> SEQ ID NO 19
<211> LENGTH: 23
<212> TYPE: DNA
<213> ORGANISM: Homo sapiens

<400> SEQUENCE: 19
caccgtgcat gtatagttta att                                            23

<210> SEQ ID NO 20
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 20
uuaaacuaua caugcacggu u                                              21

<210> SEQ ID NO 21
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 21
ggugccuucu ugguauuguu u                                              21

<210> SEQ ID NO 22
<211> LENGTH: 23
<212> TYPE: DNA
<213> ORGANISM: Homo sapiens
```

```
<400> SEQUENCE: 22
ttggtgcctt cttggtattg tac                                             23

<210> SEQ ID NO 23
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 23
acaauaccaa gaaggcaccu u                                               21

<210> SEQ ID NO 24
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 24
gaggaacacu gcgucuuuau u                                               21

<210> SEQ ID NO 25
<211> LENGTH: 23
<212> TYPE: DNA
<213> ORGANISM: Homo sapiens

<400> SEQUENCE: 25
gagaggaaca ctgcgtcttt aaa                                             23

<210> SEQ ID NO 26
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 26
uaaagacgca guguccucu u                                                21

<210> SEQ ID NO 27
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 27
guggucacuu guaccauauu u                                               21

<210> SEQ ID NO 28
<211> LENGTH: 23
<212> TYPE: DNA
<213> ORGANISM: homo sapiens

<400> SEQUENCE: 28
ctgtggtcac ttgtaccata tag                                             23

<210> SEQ ID NO 29
<211> LENGTH: 21
<212> TYPE: RNA
<213> ORGANISM: Artificial Sequence
<220> FEATURE:
```

<223> OTHER INFORMATION: a synthetic siRNA sequence

<400> SEQUENCE: 29
auaugguaca agugaccacu u                                              21

<210> SEQ ID NO 30
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 30
cccaaguuua agggaaauau u                                              21

<210> SEQ ID NO 31
<211> LENGTH: 23
<212> TYPE: DNA
<213> ORGANISM: homo sapiens

<400> SEQUENCE: 31
atcccaagtt taagggaaat att                                            23

<210> SEQ ID NO 32
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 32
uauuucccuu aaacuugggu u                                              21

<210> SEQ ID NO 33
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 33
cagccauuca gaggaaacuu u                                              21

<210> SEQ ID NO 34
<211> LENGTH: 23
<212> TYPE: DNA
<213> ORGANISM: homo sapiens

<400> SEQUENCE: 34
ttcagccatt cagaggaaac tgt                                            23

<210> SEQ ID NO 35
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 35 aguuccucu gaauggcugu u                                               21

<210> SEQ ID NO 36
<211> LENGTH: 21
<212> TYPE: RNA
<213> ORGANISM: Artificial Sequence

```
<220> FEATURE:
<223> OTHER INFORMATION: a synthetic siRNA sequence

<400> SEQUENCE: 36
gugggaugga auugaaagau u                                              21

<210> SEQ ID NO 37
<211> LENGTH: 23
<212> TYPE: DNA
<213> ORGANISM: homo sapiens

<400> SEQUENCE: 37
cagtgggatg gaattgaaag aac                                            23

<210> SEQ ID NO 38
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 38
ucuuucaauu ccaucccacu u                                              21

<210> SEQ ID NO 39
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 39
ggcucuucuu acauuuguau u                                              21

<210> SEQ ID NO 40
<211> LENGTH: 23
<212> TYPE: DNA
<213> ORGANISM: homo sapiens

<400> SEQUENCE: 40
ttggctcttc ttacatttgt aaa                                            23

<210> SEQ ID NO 41
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 41
uacaaaugua agaagagccu u                                              21

<210> SEQ ID NO 42
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 42
ccggauaaca cugauuaguu u                                              21

<210> SEQ ID NO 43
<211> LENGTH: 23
<212> TYPE: DNA
```

```
<213> ORGANISM: homo sapiens

<400> SEQUENCE: 43
taccggataa cactgattag tca                                          23

<210> SEQ ID NO 44
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 44
acuaaucagu guuauccggu u                                            21

<210> SEQ ID NO 45
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 45
caccaaccau cgagcaaauu u                                            21

<210> SEQ ID NO 46
<211> LENGTH: 23
<212> TYPE: DNA
<213> ORGANISM: homo sapiens

<400> SEQUENCE: 46
agcaccaacc atcgagcaaa tga                                          23

<210> SEQ ID NO 47
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 47
auuugcucga ugguuggugu u                                            21

<210> SEQ ID NO 48
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 48
gguagucacu aacauauauu u                                            21

<210> SEQ ID NO 49
<211> LENGTH: 23
<212> TYPE: DNA
<213> ORGANISM: homo sapiens

<400> SEQUENCE: 49
atggtagtca ctaacatata taa                                          23

<210> SEQ ID NO 50
<211> LENGTH: 21
<212> TYPE: RNA
<213> ORGANISM: Artificial Sequence
```

```
<220> FEATURE:
<223> OTHER INFORMATION: a synthetic siRNA sequence

<400> SEQUENCE: 50
auauauguua gugacuaccu u                                              21

<210> SEQ ID NO 51
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 51
gugccuucuu gguauuguau u                                              21

<210> SEQ ID NO 52
<211> LENGTH: 23
<212> TYPE: DNA
<213> ORGANISM: homo sapiens

<400> SEQUENCE: 52
tggtgccttc ttggtattgt acc                                            23

<210> SEQ ID NO 53
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 53
uacaauacca agaaggcacu u                                              21

<210> SEQ ID NO 54
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 54
caggguuccu gacagaauau u                                              21

<210> SEQ ID NO 55
<211> LENGTH: 23
<212> TYPE: DNA
<213> ORGANISM: homo sapiens

<400> SEQUENCE: 55
cacagggttc ctgacagaat atg                                            23

<210> SEQ ID NO 56
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 56
uauucuguca ggaacccugu u                                              21

<210> SEQ ID NO 57
<211> LENGTH: 21
<212> TYPE: RNA
```

```
<213> ORGANISM: Artificial Sequence
<220> FEATURE:
<223> OTHER INFORMATION: a synthetic siRNA sequence

<400> SEQUENCE: 57
ccaccuguga ucucaagauu u                                              21

<210> SEQ ID NO 58
<211> LENGTH: 23
<212> TYPE: DNA
<213> ORGANISM: homo sapiens

<400> SEQUENCE: 58
caccacctgt gatctcaaga tct                                            23

<210> SEQ ID NO 59
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 59
aucuugagau cacagguggu u                                              21

<210> SEQ ID NO 60
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 60
cccuugagcu acuucaaauu u                                              21

<210> SEQ ID NO 61
<211> LENGTH: 23
<212> TYPE: DNA
<213> ORGANISM: homo sapiens

<400> SEQUENCE: 61
cgcccttgag ctacttcaaa tgt                                            23

<210> SEQ ID NO 62
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 62
auuugaagua gcucaagggu u                                              21

<210> SEQ ID NO 63
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 63
gugcagauga gaagcuauau u                                              21

<210> SEQ ID NO 64
<211> LENGTH: 23
```

```
<212> TYPE: DNA
<213> ORGANISM: homo sapiens

<400> SEQUENCE: 64
tggtgcagat gagaagctat aac                                              23

<210> SEQ ID NO 65
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 65
uauagcuucu caucugcacu u                                                21

<210> SEQ ID NO 66
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 66
gcucugcuua ugauaauguu u                                                21

<210> SEQ ID NO 67
<211> LENGTH: 23
<212> TYPE: DNA
<213> ORGANISM: homo sapiens

<400> SEQUENCE: 67
gtgctctgct tatgataatg tca                                              23

<210> SEQ ID NO 68
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 68
acauuaucau aagcagagcu u                                                21

<210> SEQ ID NO 69
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 69
gucagaaaca aauggaaauu u                                                21

<210> SEQ ID NO 70
<211> LENGTH: 23
<212> TYPE: DNA
<213> ORGANISM: homo sapiens

<400> SEQUENCE: 70
gggtcagaaa caaatggaaa tcc                                              23

<210> SEQ ID NO 71
<211> LENGTH: 21
<212> TYPE: RNA
```

```
<213> ORGANISM: Artificial Sequence
<220> FEATURE:
<223> OTHER INFORMATION: a synthetic siRNA sequence

<400> SEQUENCE: 71
auuuccauuu guuucugacu u                                              21

<210> SEQ ID NO 72
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 72
gccuacgauu gaaugaaau u                                               21

<210> SEQ ID NO 73
<211> LENGTH: 23
<212> TYPE: DNA
<213> ORGANISM: homo sapiens

<400> SEQUENCE: 73
atgcctacga ttgaaatgaa aac                                            23

<210> SEQ ID NO 74
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 74
uuucauuuca aucguaggcu u                                              21

<210> SEQ ID NO 75
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 75
cccugguucu cucuaaagau u                                              21

<210> SEQ ID NO 76
<211> LENGTH: 23
<212> TYPE: DNA
<213> ORGANISM: homo sapiens

<400> SEQUENCE: 76
ttccctggtt ctctctaaag agg                                            23

<210> SEQ ID NO 77
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 77
ucuuuagaga gaaccagggu u                                              21

<210> SEQ ID NO 78
<211> LENGTH: 21
```

```
<212> TYPE: RNA
<213> ORGANISM: Artificial Sequence
<220> FEATURE:
<223> OTHER INFORMATION: a synthetic siRNA sequence

<400> SEQUENCE: 78
ggguagaaga auacuguauu u                                                 21

<210> SEQ ID NO 79
<211> LENGTH: 23
<212> TYPE: DNA
<213> ORGANISM: homo sapiens

<400> SEQUENCE: 79
ctgggtagaa gaatactgta ttg                                               23

<210> SEQ ID NO 80
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 80
auacaguauu cuucuacccu u                                                 21

<210> SEQ ID NO 81
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 81
ccaaguuuaa gggaaauauu u                                                 21

<210> SEQ ID NO 82
<211> LENGTH: 23
<212> TYPE: DNA
<213> ORGANISM: homo sapiens

<400> SEQUENCE: 82
tcccaagttt aagggaaata ttt                                               23

<210> SEQ ID NO 83
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 83
auauuucccu uaaacuuggu u                                                 21

<210> SEQ ID NO 84
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 84
ggugugcucu gcuuaugauu u                                                 21

<210> SEQ ID NO 85
```

```
<211> LENGTH: 23
<212> TYPE: DNA
<213> ORGANISM: homo sapiens

<400> SEQUENCE: 85
atggtgtgct ctgcttatga taa                                              23

<210> SEQ ID NO 86
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 86
aucauaagca gagcacaccu u                                                21

<210> SEQ ID NO 87
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 87
gagcaaauga aagauguauu u                                                21

<210> SEQ ID NO 88
<211> LENGTH: 23
<212> TYPE: DNA
<213> ORGANISM: homo sapiens

<400> SEQUENCE: 88
tcgagcaaat gaaagatgta tat                                              23

<210> SEQ ID NO 89
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 89
auacaucuuu cauuugcucu u                                                21

<210> SEQ ID NO 90
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 90
cagagcaaga agucauaaau u                                                21

<210> SEQ ID NO 91
<211> LENGTH: 23
<212> TYPE: DNA
<213> ORGANISM: homo sapiens

<400> SEQUENCE: 91
ttcagagcaa gaagtcataa aga                                              23

<210> SEQ ID NO 92
<211> LENGTH: 21
```

```
<212> TYPE: RNA
<213> ORGANISM: Artificial Sequence
<220> FEATURE:
<223> OTHER INFORMATION: a synthetic siRNA sequence

<400> SEQUENCE: 92
uuuaugacuu cuugcucugu u                                             21

<210> SEQ ID NO 93
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 93
guccucuucu aaauagaaau u                                             21

<210> SEQ ID NO 94
<211> LENGTH: 23
<212> TYPE: DNA
<213> ORGANISM: homo sapiens

<400> SEQUENCE: 94
gagtcctctt ctaaatagaa aac                                           23

<210> SEQ ID NO 95
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 95
uuucuauuua gaagaggacu u                                             21

<210> SEQ ID NO 96
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 96
cuggcagaaa ugcuuucuau u                                             21

<210> SEQ ID NO 97
<211> LENGTH: 23
<212> TYPE: DNA
<213> ORGANISM: homo sapiens

<400> SEQUENCE: 97
ttctggcaga aatgctttct aac                                           23

<210> SEQ ID NO 98
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 98
uagaaagcau uucugccagu u                                             21

<210> SEQ ID NO 99
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 99
gccuuguuca auaauuacuu u                                              21

<210> SEQ ID NO 100
<211> LENGTH: 23
<212> TYPE: DNA
<213> ORGANISM: homo sapiens

<400> SEQUENCE: 100
ttgccttgtt caataattac tgt                                            23

<210> SEQ ID NO 101
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 101
aguaauuauu gaacaaggcu u                                              21

<210> SEQ ID NO 102
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 102
gcuccagaaa uuauguugau u                                              21

<210> SEQ ID NO 103
<211> LENGTH: 23
<212> TYPE: DNA
<213> ORGANISM: homo sapiens

<400> SEQUENCE: 103
gggctccaga aattatgttg aat                                            23

<210> SEQ ID NO 104
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 104
ucaacauaau uucuggagcu u                                              21

<210> SEQ ID NO 105
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 105
cccagcacuu ggauuuacau u                                              21
```

```
<210> SEQ ID NO 106
<211> LENGTH: 23
<212> TYPE: DNA
<213> ORGANISM: homo sapiens

<400> SEQUENCE: 106
ggcccagcac ttggatttac ata                                            23

<210> SEQ ID NO 107
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 107
uguaaaucca agugcugggu u                                              21

<210> SEQ ID NO 108
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 108
gccuuguaua ugguaaagau u                                              21

<210> SEQ ID NO 109
<211> LENGTH: 23
<212> TYPE: DNA
<213> ORGANISM: homo sapiens

<400> SEQUENCE: 109
ttgccttgta tatggtaaag att                                            23

<210> SEQ ID NO 110
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 110
ucuuuaccau auacaaggcu u                                              21

<210> SEQ ID NO 111
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 111
gcgcuagcua ucauguguau u                                              21

<210> SEQ ID NO 112
<211> LENGTH: 23
<212> TYPE: DNA
<213> ORGANISM: homo sapiens

<400> SEQUENCE: 112
aagcgctagc tatcatgtgt agt                                            23

<210> SEQ ID NO 113
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 113
uacacaugau agcuagcgcu u                                              21

<210> SEQ ID NO 114
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 114
ggagucagau uggcaugaau u                                              21

<210> SEQ ID NO 115
<211> LENGTH: 23
<212> TYPE: DNA
<213> ORGANISM: homo sapiens

<400> SEQUENCE: 115
gtggagtcag attggcatga aac                                            23

<210> SEQ ID NO 116
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 116
uucaugccaa ucugacuccu u                                              21

<210> SEQ ID NO 117
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 117
gcaucugggu agaagaauau u                                              21

<210> SEQ ID NO 118
<211> LENGTH: 23
<212> TYPE: DNA
<213> ORGANISM: homo sapiens

<400> SEQUENCE: 118
tggcatctgg gtagaagaat act                                            23

<210> SEQ ID NO 119
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 119
uauucuucua cccagaugcu u                                              21
```

```
<210> SEQ ID NO 120
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 120
ggcauuaugu aaugacuuau u                                              21

<210> SEQ ID NO 121
<211> LENGTH: 23
<212> TYPE: DNA
<213> ORGANISM: homo sapiens

<400> SEQUENCE: 121
tgggcattat gtaatgactt att                                            23

<210> SEQ ID NO 122
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 122
uaagucauua cauaaugccu u                                              21

<210> SEQ ID NO 123
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 123
gcucuucuua cauuuguaau u                                              21

<210> SEQ ID NO 124
<211> LENGTH: 23
<212> TYPE: DNA
<213> ORGANISM: homo sapiens

<400> SEQUENCE: 124
tggctcttct tacatttgta aaa                                            23

<210> SEQ ID NO 125
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 125
uuacaaaugu aagaagagcu u                                              21

<210> SEQ ID NO 126
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 126
gcugguguuu gaaacaugau u                                              21
```

```
<210> SEQ ID NO 127
<211> LENGTH: 23
<212> TYPE: DNA
<213> ORGANISM: homo sapiens

<400> SEQUENCE: 127
atgctggtgt ttgaaacatg ata                                              23

<210> SEQ ID NO 128
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 128
ucauguuuca aacaccagcu u                                                21

<210> SEQ ID NO 129
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 129
gggcacuuua agucagugau u                                                21

<210> SEQ ID NO 130
<211> LENGTH: 23
<212> TYPE: DNA
<213> ORGANISM: homo sapiens

<400> SEQUENCE: 130
tagggcactt taagtcagtg aca                                              23

<210> SEQ ID NO 131
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 131
ucacugacuu aaagugcccu u                                                21

<210> SEQ ID NO 132
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 132
gcaguacuua auguuuguau u                                                21

<210> SEQ ID NO 133
<211> LENGTH: 23
<212> TYPE: DNA
<213> ORGANISM: homo sapiens

<400> SEQUENCE: 133
gtgcagtact taatgtttgt aag                                              23
```

-continued

```
<210> SEQ ID NO 134
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 134
uacaaacauu aaguacugcu u                                              21

<210> SEQ ID NO 135
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 135
cagauuaggu caucuuaauu u                                              21

<210> SEQ ID NO 136
<211> LENGTH: 23
<212> TYPE: DNA
<213> ORGANISM: homo sapiens

<400> SEQUENCE: 136
tacagattag gtcatcttaa ttc                                            23

<210> SEQ ID NO 137
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 137
auuaagauga ccuaaucugu u                                              21

<210> SEQ ID NO 138
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 138
ggugagaaau uugccuuguu u                                              21

<210> SEQ ID NO 139
<211> LENGTH: 23
<212> TYPE: DNA
<213> ORGANISM: homo sapiens

<400> SEQUENCE: 139
gtggtgagaa atttgccttg ttc                                            23

<210> SEQ ID NO 140
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 140
acaaggcaaa uuucucaccu u                                              21
```

<210> SEQ ID NO 141
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 141
gaagcuauaa cagugaauau u                                          21

<210> SEQ ID NO 142
<211> LENGTH: 23
<212> TYPE: DNA
<213> ORGANISM: homo sapiens

<400> SEQUENCE: 142
gagaagctat aacagtgaat atg                                        23

<210> SEQ ID NO 143
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 143
uauucacugu uauagcuucu u                                          21

<210> SEQ ID NO 144
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 144
gaagaccuga auuguauaau u                                          21

<210> SEQ ID NO 145
<211> LENGTH: 23
<212> TYPE: DNA
<213> ORGANISM: homo sapiens

<400> SEQUENCE: 145
aagaagacct gaattgtata ata                                        23

<210> SEQ ID NO 146
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 146
uuauacaauu caggucuucu u                                          21

<210> SEQ ID NO 147
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 147
gagcacucaa gaaaguucuu u                                          21

<210> SEQ ID NO 148
<211> LENGTH: 23
<212> TYPE: DNA
<213> ORGANISM: homo sapiens

<400> SEQUENCE: 148
tagagcactc aagaaagttc tga                                           23

<210> SEQ ID NO 149
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 149
agaacuuucu ugagugcucu u                                             21

<210> SEQ ID NO 150
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 150
cuccagaaau uauguugaau u                                             21

<210> SEQ ID NO 151
<211> LENGTH: 23
<212> TYPE: DNA
<213> ORGANISM: homo sapiens

<400> SEQUENCE: 151
ggctccagaa attatgttga att                                           23

<210> SEQ ID NO 152
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 152
uucaacauaa uuucuggagu u                                             21

<210> SEQ ID NO 153
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 153
gcuucagaca ugagaacauu u                                             21

<210> SEQ ID NO 154
<211> LENGTH: 23
<212> TYPE: DNA
<213> ORGANISM: homo sapiens

<400> SEQUENCE: 154
gcgcttcaga catgagaaca tca                                           23

<210> SEQ ID NO 155
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 155
auguucucau gucugaagcu u                                              21

<210> SEQ ID NO 156
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 156
guuccuuuau ucacaaucuu u                                              21

<210> SEQ ID NO 157
<211> LENGTH: 23
<212> TYPE: DNA
<213> ORGANISM: homo sapiens

<400> SEQUENCE: 157
atgttccttt attcacaatc tta                                            23

<210> SEQ ID NO 158
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 158
agauugugaa uaaaggaacu u                                              21

<210> SEQ ID NO 159
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 159
gugucacucu guaguuacuu u                                              21

<210> SEQ ID NO 160
<211> LENGTH: 23
<212> TYPE: DNA
<213> ORGANISM: homo sapiens

<400> SEQUENCE: 160
cagtgtcact ctgtagttac tgt                                            23

<210> SEQ ID NO 161
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 161
aguaacuaca gagugacacu u                                              21

<210> SEQ ID NO 162
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 162
gcuguaaagu ggaagcaauu u                                                21

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166
<211> LENGTH: 23
<212> TYPE: DNA
<213> ORGANISM: homo sapiens

<400> SEQUENCE: 166
cagctgtaaa gtggaagcaa tat                                              23

<210> SEQ ID NO 167
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 167
auugcuucca cuuuacagcu u                                                21

<210> SEQ ID NO 168
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 168
ccacaugccu acgauugaau u                                                21

<210> SEQ ID NO 169
<211> LENGTH: 23
<212> TYPE: DNA
<213> ORGANISM: homo sapiens

<400> SEQUENCE: 169
tgccacatgc ctacgattga aat                                              23

```
-continued

<210> SEQ ID NO 170
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 170
uucaaucgua ggcauguggu u                                              21

<210> SEQ ID NO 171
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 171
gucagcaucu caaguucauu u                                              21

<210> SEQ ID NO 172
<211> LENGTH: 23
<212> TYPE: DNA
<213> ORGANISM: homo sapiens

<400> SEQUENCE: 172
atgtcagcat ctcaagttca ttt                                            23

<210> SEQ ID NO 173
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 173
augaacuuga gaugcugacu u                                              21

<210> SEQ ID NO 174
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 174
gggacacaga aaugugacuu u                                              21

<210> SEQ ID NO 175
<211> LENGTH: 23
<212> TYPE: DNA
<213> ORGANISM: homo sapiens

<400> SEQUENCE: 175
acgggacaca gaaatgtgac tgt                                            23

<210> SEQ ID NO 176
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 176
agucacauuu cuguguccu u                                               21
```

```
<210> SEQ ID NO 177
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 177
ccagugggau ggaauugaau u                                              21

<210> SEQ ID NO 178
<211> LENGTH: 23
<212> TYPE: DNA
<213> ORGANISM: homo sapiens

<400> SEQUENCE: 178
agccagtggg atggaattga aag                                            23

<210> SEQ ID NO 179
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 179
uucaauucca ucccacuggu u                                              21

<210> SEQ ID NO 180
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 180
ccugcuaaua ugaacagaau u                                              21

<210> SEQ ID NO 181
<211> LENGTH: 23
<212> TYPE: DNA
<213> ORGANISM: homo sapiens

<400> SEQUENCE: 181
tgcctgctaa tatgaacaga aat                                            23

<210> SEQ ID NO 182
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 182
uucuguucau auuagcaggu u                                              21

<210> SEQ ID NO 183
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 183
cugcuaauau gaacagaaau u                                              21
```

<210> SEQ ID NO 184
<211> LENGTH: 23
<212> TYPE: DNA
<213> ORGANISM: homo sapiens

<400> SEQUENCE: 184
gcctgctaat atgaacagaa atg                                              23

<210> SEQ ID NO 185
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 185
uuucuguuca uauuagcagu u                                                21

<210> SEQ ID NO 186
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 186
gagucagauu ggcaugaaau u                                                21

<210> SEQ ID NO 187
<211> LENGTH: 23
<212> TYPE: DNA
<213> ORGANISM: homo sapiens

<400> SEQUENCE: 187
tggagtcaga ttggcatgaa acc                                              23

<210> SEQ ID NO 188
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 188
uuucaugcca aucugacucu u                                                21

<210> SEQ ID NO 189
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 189
cugccugcua auaugaacau u                                                21

<210> SEQ ID NO 190
<211> LENGTH: 23
<212> TYPE: DNA
<213> ORGANISM: homo sapiens

<400> SEQUENCE: 190
gactgcctgc taatatgaac aga                                              23

<210> SEQ ID NO 191
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 191
uguucauauu agcaggcagu u                                              21

<210> SEQ ID NO 192
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 192
cgucuuuaaa ugagaaaguu u                                              21

<210> SEQ ID NO 193
<211> LENGTH: 23
<212> TYPE: DNA
<213> ORGANISM: homo sapiens

<400> SEQUENCE: 193
tgcgtcttta aatgagaaag tat                                            23

<210> SEQ ID NO 194
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 194
acuuucucau uuaaagacgu u                                              21

<210> SEQ ID NO 195
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 195
gcuacaccaa guccauugau u                                              21

<210> SEQ ID NO 196
<211> LENGTH: 23
<212> TYPE: DNA
<213> ORGANISM: homo sapiens

<400> SEQUENCE: 196
gggctacacc aagtccattg ata                                            23

<210> SEQ ID NO 197
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 197
ucaauggacu ugguguagcu u                                              21

```
<210> SEQ ID NO 198
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 198
cagggaagca uuaucuugau u                                              21

<210> SEQ ID NO 199
<211> LENGTH: 23
<212> TYPE: DNA
<213> ORGANISM: homo sapiens

<400> SEQUENCE: 199
tccagggaag cattatcttg acc                                            23

<210> SEQ ID NO 200
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 200
ucaagauaau gcuucccugu u                                              21

<210> SEQ ID NO 201
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 201
cuccaaagcu cuggacuuau u                                              21

<210> SEQ ID NO 202
<211> LENGTH: 23
<212> TYPE: DNA
<213> ORGANISM: homo sapiens

<400> SEQUENCE: 202
gactccaaag ctctggactt att                                            23

<210> SEQ ID NO 203
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 203
uaaguccaga gcuuuggagu u                                              21

<210> SEQ ID NO 204
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 204
```

```
gcaauggaga auggguuauu u                                                21

<210> SEQ ID NO 205
<211> LENGTH: 23
<212> TYPE: DNA
<213> ORGANISM: homo sapiens

<400> SEQUENCE: 205
cagcaatgga gaatgggtta tat                                              23

<210> SEQ ID NO 206
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 206
auaacccauu cuccauugcu u                                                21

<210> SEQ ID NO 207
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 207
gggucagaaa caauggaau u                                                 21

<210> SEQ ID NO 208
<211> LENGTH: 23
<212> TYPE: DNA
<213> ORGANISM: homo sapiens

<400> SEQUENCE: 208
atgggtcaga aacaaatgga aat                                              23

<210> SEQ ID NO 209
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 209
uuccauuugu uucugacccu u                                                21

<210> SEQ ID NO 210
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 210
guaccauaua gagguguaau u                                                21

<210> SEQ ID NO 211
<211> LENGTH: 23
<212> TYPE: DNA
<213> ORGANISM: homo sapiens

<400> SEQUENCE: 211
ttgtaccata tagaggtgta aca                                              23
```

<210> SEQ ID NO 212
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 212
uuacaccucu auaugguacu u                                              21

<210> SEQ ID NO 213
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 213
guggguguuu caguaaccau u                                              21

<210> SEQ ID NO 214
<211> LENGTH: 23
<212> TYPE: DNA
<213> ORGANISM: homo sapiens

<400> SEQUENCE: 214
atgtgggtgt ttcagtaacc acg                                            23

<210> SEQ ID NO 215
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 215
ugguuacuga aacacccacu u                                              21

<210> SEQ ID NO 216
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 216
guagagcacu caagaaaguu u                                              21

<210> SEQ ID NO 217
<211> LENGTH: 23
<212> TYPE: DNA
<213> ORGANISM: homo sapiens

<400> SEQUENCE: 217
gtgtagagca ctcaagaaag ttc                                            23

<210> SEQ ID NO 218
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 218 acuucuuga gugcucuacu u                                     21

<210> SEQ ID NO 219
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 219
ccaguccuuu cauuuaguau u                                    21

<210> SEQ ID NO 220
<211> LENGTH: 23
<212> TYPE: DNA
<213> ORGANISM: homo sapiens

<400> SEQUENCE: 220
ttccagtcct ttcatttagt ata                                  23

<210> SEQ ID NO 221
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 221
uacuaaauga aaggacuggu u                                    21

<210> SEQ ID NO 222
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 222
gccugcuaau augaacagau u                                    21

<210> SEQ ID NO 223
<211> LENGTH: 23
<212> TYPE: DNA
<213> ORGANISM: homo sapiens

<400> SEQUENCE: 223
ctgcctgcta atatgaacag aaa                                  23

<210> SEQ ID NO 224
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 224
ucuguucaua uuagcaggcu u                                    21

<210> SEQ ID NO 225
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 225
cagugaauau gugguuucuu u                                                 21

<210> SEQ ID NO 226
<211> LENGTH: 23
<212> TYPE: DNA
<213> ORGANISM: homo sapiens

<400> SEQUENCE: 226
aacagtgaat atgtggtttc tct                                               23

<210> SEQ ID NO 227
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 227
agaaaccaca uauucacugu u                                                 21

<210> SEQ ID NO 228
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 228
gaguccucuu cuaaauagau u                                                 21

<210> SEQ ID NO 229
<211> LENGTH: 23
<212> TYPE: DNA
<213> ORGANISM: homo sapiens

<400> SEQUENCE: 229
tggagtcctc ttctaaatag aaa                                               23

<210> SEQ ID NO 230
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 230
ucuauuuaga agaggacucu u                                                 21

<210> SEQ ID NO 231
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 231
gucacuugua ccauauagau u                                                 21

<210> SEQ ID NO 232
<211> LENGTH: 23
<212> TYPE: DNA
<213> ORGANISM: homo sapiens

<400> SEQUENCE: 232
tggtcacttg taccatatag agg                                              23

<210> SEQ ID NO 233
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 233
ucuauauggu acaagugacu u                                                21

<210> SEQ ID NO 234
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 234
cuauccagca gaucauuuau u                                                21

<210> SEQ ID NO 235
<211> LENGTH: 23
<212> TYPE: DNA
<213> ORGANISM: homo sapiens

<400> SEQUENCE: 235
tgctatccag cagatcattt agg                                              23

<210> SEQ ID NO 236
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 236
uaaaugaucu gcuggauagu u                                                21

<210> SEQ ID NO 237
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 237
cuggguagaa gaauacuguu u                                                21

<210> SEQ ID NO 238
<211> LENGTH: 23
<212> TYPE: DNA
<213> ORGANISM: homo sapiens

<400> SEQUENCE: 238
atctgggtag aagaatactg tat                                              23

<210> SEQ ID NO 239
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 239
acaguauucu ucuacccagu u                                              21

<210> SEQ ID NO 240
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 240
ccaucgagca aaugaaagau u                                              21

<210> SEQ ID NO 241
<211> LENGTH: 23
<212> TYPE: DNA
<213> ORGANISM: homo sapiens

<400> SEQUENCE: 241
aaccatcgag caaatgaaag atg                                            23

<210> SEQ ID NO 242
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 242
ucuuucauuu gcucgauggu u                                              21

<210> SEQ ID NO 243
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 243 cguccucaa guacucaaau u                                               21

<210> SEQ ID NO 244
<211> LENGTH: 23
<212> TYPE: DNA
<213> ORGANISM: homo sapiens

<400> SEQUENCE: 244
ttctgtcctc aagtactcaa ata                                            23

<210> SEQ ID NO 245
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 245
uuugaguacu ugaggacagu u                                              21

<210> SEQ ID NO 246
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 246
gcaccauuca aguucgacau u                                             21

<210> SEQ ID NO 247
<211> LENGTH: 23
<212> TYPE: DNA
<213> ORGANISM: homo sapiens

<400> SEQUENCE: 247
aagcaccatt caagttcgac atg                                           23

<210> SEQ ID NO 248
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 248
ugucgaacuu gaauggugcu u                                             21

<210> SEQ ID NO 249
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 249
ccucaaagcu agcagagauu u                                             21

<210> SEQ ID NO 250
<211> LENGTH: 23
<212> TYPE: DNA
<213> ORGANISM: homo sapiens

<400> SEQUENCE: 250
gtcctcaaag ctagcagaga tac                                           23

<210> SEQ ID NO 251
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 251
aucucugcua gcuuugaggu u                                             21

<210> SEQ ID NO 252
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 252
caugccacgu aauauuucau u                                             21

<210> SEQ ID NO 253
<211> LENGTH: 23
<212> TYPE: DNA
<213> ORGANISM: homo sapiens

<400> SEQUENCE: 253
cacatgccac gtaatatttc agc                                              23

<210> SEQ ID NO 254
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 254
ugaaauauua cguggcaugu u                                                21

<210> SEQ ID NO 255
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 255
caccauucaa guucgacauu u                                                21

<210> SEQ ID NO 256
<211> LENGTH: 23
<212> TYPE: DNA
<213> ORGANISM: homo sapiens

<400> SEQUENCE: 256
agcaccattc aagttcgaca tgg                                              23

<210> SEQ ID NO 257
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 257
augucgaacu ugaauggugu u                                                21

<210> SEQ ID NO 258
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 258
guuaugugca guacuuaauu u                                                21

<210> SEQ ID NO 259
<211> LENGTH: 23
<212> TYPE: DNA
<213> ORGANISM: homo sapiens

<400> SEQUENCE: 259
gcgttatgtg cagtacttaa tgt                                              23

<210> SEQ ID NO 260
<211> LENGTH: 21
<212> TYPE: RNA
<213> ORGANISM: Artificial Sequence
<220> FEATURE:
<223> OTHER INFORMATION: a synthetic siRNA sequence

```
<400> SEQUENCE: 260
auuaaguacu gcacauaacu u                                          21

<210> SEQ ID NO 261
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 261
ccuuguauau gguaaagauu u                                          21

<210> SEQ ID NO 262
<211> LENGTH: 23
<212> TYPE: DNA
<213> ORGANISM: homo sapiens

<400> SEQUENCE: 262
tgccttgtat atggtaaaga tta                                        23

<210> SEQ ID NO 263
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 263
aucuuuacca uauacaaggu u                                          21

<210> SEQ ID NO 264
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 264
cccaaaugcu gacuccaaau u                                          21

<210> SEQ ID NO 265
<211> LENGTH: 23
<212> TYPE: DNA
<213> ORGANISM: homo sapiens

<400> SEQUENCE: 265
ttcccaaatg ctgactccaa agc                                        23

<210> SEQ ID NO 266
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 266
uuuggaguca gcauuugggu u                                          21

<210> SEQ ID NO 267
<211> LENGTH: 21
<212> TYPE: RNA
<213> ORGANISM: Artificial Sequence
<220> FEATURE:
<223> OTHER INFORMATION: a synthetic siRNA sequence
```

<400> SEQUENCE: 267
ggauggaauu gaaagaacuu u                                              21

<210> SEQ ID NO 268
<211> LENGTH: 23
<212> TYPE: DNA
<213> ORGANISM: homo sapiens

<400> SEQUENCE: 268
tgggatggaa ttgaaagaac taa                                            23

<210> SEQ ID NO 269
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 269
aguucuuuca auuccauccu u                                              21

<210> SEQ ID NO 270
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 270
cugcgucuuu aaaugagaau u                                              21

<210> SEQ ID NO 271
<211> LENGTH: 23
<212> TYPE: DNA
<213> ORGANISM: homo sapiens

<400> SEQUENCE: 271
cactgcgtct ttaaatgaga aag                                            23

<210> SEQ ID NO 272
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 272
uucucauuua aagacgcagu u                                              21

<210> SEQ ID NO 273
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 273
gccauucaga ggaaacuguu u                                              21

<210> SEQ ID NO 274
<211> LENGTH: 23
<212> TYPE: DNA
<213> ORGANISM: homo sapiens

```
<400> SEQUENCE: 274
cagccattca gaggaaactg ttt                                              23

<210> SEQ ID NO 275
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 275
acaguuuccu cugaauggcu u                                                21

<210> SEQ ID NO 276
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 276
gucuaguccu ucguuauguu u                                                21

<210> SEQ ID NO 277
<211> LENGTH: 23
<212> TYPE: DNA
<213> ORGANISM: homo sapiens

<400> SEQUENCE: 277
ttgtctagtc cttcgttatg ttc                                              23

<210> SEQ ID NO 278
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 278
acauaacgaa ggacuagacu u                                                21

<210> SEQ ID NO 279
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 279
gugucccugu auuaccaaau u                                                21

<210> SEQ ID NO 280
<211> LENGTH: 23
<212> TYPE: DNA
<213> ORGANISM: homo sapiens

<400> SEQUENCE: 280
ttgtgtccct gtattaccaa aat                                              23

<210> SEQ ID NO 281
<211> LENGTH: 21
<212> TYPE: RNA
<213> ORGANISM: Artificial Sequence
<220> FEATURE:
<223> OTHER INFORMATION: a synthetic siRNA sequence
```

```
<400> SEQUENCE: 281
uuugguaaua cagggacacu u                                              21

<210> SEQ ID NO 282
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 282
cagcauguca gcaucucaau u                                              21

<210> SEQ ID NO 283
<211> LENGTH: 23
<212> TYPE: DNA
<213> ORGANISM: homo sapiens

<400> SEQUENCE: 283
tacagcatgt cagcatctca agt                                            23

<210> SEQ ID NO 284
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 284
uugagaugcu gacaugcugu u                                              21

<210> SEQ ID NO 285
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 285
guguaacacu ugucaagaau u                                              21

<210> SEQ ID NO 286
<211> LENGTH: 23
<212> TYPE: DNA
<213> ORGANISM: homo sapiens

<400> SEQUENCE: 286
aggtgtaaca cttgtcaaga agc                                            23

<210> SEQ ID NO 287
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 287
uucuugacaa guguuacacu u                                              21

<210> SEQ ID NO 288
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 288
guguagagca cucaagaaau u                                          21

<210> SEQ ID NO 289
<211> LENGTH: 23
<212> TYPE: DNA
<213> ORGANISM: homo sapiens

<400> SEQUENCE: 289
gcgtgtagag cactcaagaa agt                                        23

<210> SEQ ID NO 290
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 290
uuucuugagu gcucuacacu u                                          21

<210> SEQ ID NO 291
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 291
cagcagauca uuuaggaaau u                                          21

<210> SEQ ID NO 292
<211> LENGTH: 23
<212> TYPE: DNA
<213> ORGANISM: homo sapiens

<400> SEQUENCE: 292
tccagcagat catttaggaa aaa                                        23

<210> SEQ ID NO 293
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 293
uuuccuaaau gaucugcugu u                                          21

<210> SEQ ID NO 294
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 294
cagauccuca gaggguuaau u                                          21

<210> SEQ ID NO 295
<211> LENGTH: 23
<212> TYPE: DNA
<213> ORGANISM: homo sapiens
```

```
<400> SEQUENCE: 295
accagatcct cagagggtta aaa                                              23

<210> SEQ ID NO 296
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 296
uuaacccucu gaggaucugu u                                                21

<210> SEQ ID NO 297
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 297
gaacaucauu ggaaucaauu u                                                21

<210> SEQ ID NO 298
<211> LENGTH: 23
<212> TYPE: DNA
<213> ORGANISM: homo sapiens

<400> SEQUENCE: 298
gagaacatca ttggaatcaa tga                                              23

<210> SEQ ID NO 299
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 299
auugauucca augauguucu u                                                21

<210> SEQ ID NO 300
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 300
gcuaucaugu guaguagauu u                                                21

<210> SEQ ID NO 301
<211> LENGTH: 23
<212> TYPE: DNA
<213> ORGANISM: homo sapiens

<400> SEQUENCE: 301
tagctatcat gtgtagtaga tgc                                              23

<210> SEQ ID NO 302
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 302
aucuacuaca caugauagcu u                                              21

<210> SEQ ID NO 303
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 303
cugcuuauga uaaugucaau u                                              21

<210> SEQ ID NO 304
<211> LENGTH: 23
<212> TYPE: DNA
<213> ORGANISM: homo sapiens

<400> SEQUENCE: 304
ctctgcttat gataatgtca aca                                            23

<210> SEQ ID NO 305
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 305
uugacauuau cauaagcagu u                                              21

<210> SEQ ID NO 306
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 306
cuuggcuuau ccacuuugau u                                              21

<210> SEQ ID NO 307
<211> LENGTH: 23
<212> TYPE: DNA
<213> ORGANISM: homo sapiens

<400> SEQUENCE: 307
gtcttggctt atccactttg act                                            23

<210> SEQ ID NO 308
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 308
ucaaagugga uaagccaagu u                                              21

<210> SEQ ID NO 309
<211> LENGTH: 21
<212> TYPE: RNA
<213> ORGANISM: Artificial Sequence
```

```
<220> FEATURE:
<223> OTHER INFORMATION: a synthetic siRNA sequence

<400> SEQUENCE: 309
gucucaaaua uucugucaau u                                             21

<210> SEQ ID NO 310
<211> LENGTH: 23
<212> TYPE: DNA
<213> ORGANISM: homo sapiens

<400> SEQUENCE: 310
aggtctcaaa tattctgtca aac                                           23

<210> SEQ ID NO 311
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 311
uugacagaau auuugagacu u                                             21

<210> SEQ ID NO 312
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 312
gcuuucuggu uugaaagauu u                                             21

<210> SEQ ID NO 313
<211> LENGTH: 23
<212> TYPE: DNA
<213> ORGANISM: homo sapiens

<400> SEQUENCE: 313
ttgctttctg gtttgaaaga tgc                                           23

<210> SEQ ID NO 314
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 314
aucuuucaaa ccagaaagcu u                                             21

<210> SEQ ID NO 315
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 315
caaccaucga gcaaaugaau u                                             21

<210> SEQ ID NO 316
<211> LENGTH: 23
<212> TYPE: DNA
```

```
<213> ORGANISM: homo sapiens

<400> SEQUENCE: 316
accaaccatc gagcaaatga aag                                        23

<210> SEQ ID NO 317
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 317
uucauuugcu cgaugguugu u                                          21

<210> SEQ ID NO 318
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 318
caucgagcaa augaaagauu u                                          21

<210> SEQ ID NO 319
<211> LENGTH: 23
<212> TYPE: DNA
<213> ORGANISM: homo sapiens

<400> SEQUENCE: 319
accatcgagc aaatgaaaga tgt                                        23

<210> SEQ ID NO 320
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 320
aucuuucauu ugcucgaugu u                                          21

<210> SEQ ID NO 321
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 321
guucagcaua guacuucaau u                                          21

<210> SEQ ID NO 322
<211> LENGTH: 23
<212> TYPE: DNA
<213> ORGANISM: homo sapiens

<400> SEQUENCE: 322
ctgttcagca tagtacttca aag                                        23

<210> SEQ ID NO 323
<211> LENGTH: 21
<212> TYPE: RNA
<213> ORGANISM: Artificial Sequence
```

```
<220> FEATURE:
<223> OTHER INFORMATION: a synthetic siRNA sequence

<400> SEQUENCE: 323
uugaaguacu augcugaacu u                                              21

<210> SEQ ID NO 324
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 324
ccacuaacuu cauucuagau u                                              21

<210> SEQ ID NO 325
<211> LENGTH: 23
<212> TYPE: DNA
<213> ORGANISM: homo sapiens

<400> SEQUENCE: 325
aaccactaac ttcattctag aat                                            23

<210> SEQ ID NO 326
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 326
ucuagaauga aguuaguggu u                                              21

<210> SEQ ID NO 327
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 327
caccucagca augaccauau u                                              21

<210> SEQ ID NO 328
<211> LENGTH: 23
<212> TYPE: DNA
<213> ORGANISM: homo sapiens

<400> SEQUENCE: 328
aacacctcag caatgaccat atc                                            23

<210> SEQ ID NO 329
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 329
uauggucauu gcugaggugu u                                              21

<210> SEQ ID NO 330
<211> LENGTH: 21
<212> TYPE: RNA
```

<213> ORGANISM: Artificial Sequence
<220> FEATURE:
<223> OTHER INFORMATION: a synthetic siRNA sequence

<400> SEQUENCE: 330
cagugucacu cuguaguuau u                                              21

<210> SEQ ID NO 331
<211> LENGTH: 23
<212> TYPE: DNA
<213> ORGANISM: homo sapiens

<400> SEQUENCE: 331
agcagtgtca ctctgtagtt act                                            23

<210> SEQ ID NO 332
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 332
uaacuacaga gugacacugu u                                              21

<210> SEQ ID NO 333
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 333
cuagcuauca uguguaguau u                                              21

<210> SEQ ID NO 334
<211> LENGTH: 23
<212> TYPE: DNA
<213> ORGANISM: homo sapiens

<400> SEQUENCE: 334
cgctagctat catgtgtagt aga                                            23

<210> SEQ ID NO 335
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 335
uacuacacau gauagcuagu u                                              21

<210> SEQ ID NO 336
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 336
guagcuuuga gaagcuacau u                                              21

<210> SEQ ID NO 337
<211> LENGTH: 23

```
<212> TYPE: DNA
<213> ORGANISM: homo sapiens

<400> SEQUENCE: 337
cagtagcttt gagaagctac atg                                          23

<210> SEQ ID NO 338
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 338
uguagcuucu caaagcuacu u                                            21

<210> SEQ ID NO 339
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 339
gucaaacccu aacaaagaau u                                            21

<210> SEQ ID NO 340
<211> LENGTH: 23
<212> TYPE: DNA
<213> ORGANISM: homo sapiens

<400> SEQUENCE: 340
ctgtcaaacc ctaacaaaga agc                                          23

<210> SEQ ID NO 341
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 341
uucuuuguua ggguuugacu u                                            21

<210> SEQ ID NO 342
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 342
gacauuuggu ucuuaucaau u                                            21

<210> SEQ ID NO 343
<211> LENGTH: 23
<212> TYPE: DNA
<213> ORGANISM: homo sapiens

<400> SEQUENCE: 343
tggacatttg gttcttatca ata                                          23

<210> SEQ ID NO 344
<211> LENGTH: 21
<212> TYPE: RNA
```

<213> ORGANISM: Artificial Sequence
<220> FEATURE:
<223> OTHER INFORMATION: a synthetic siRNA sequence

<400> SEQUENCE: 344
uugauaagaa ccaaaugucu u                                              21

<210> SEQ ID NO 345
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 345
guguuugaaa caugauacuu u                                              21

<210> SEQ ID NO 346
<211> LENGTH: 23
<212> TYPE: DNA
<213> ORGANISM: homo sapiens

<400> SEQUENCE: 346
tggtgtttga aacatgatac tcc                                            23

<210> SEQ ID NO 347
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 347
aguaucaugu uucaaacacu u                                              21

<210> SEQ ID NO 348
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 348
gagaacauca uuggaaucau u                                              21

<210> SEQ ID NO 349
<211> LENGTH: 23
<212> TYPE: DNA
<213> ORGANISM: homo sapiens

<400> SEQUENCE: 349
atgagaacat cattggaatc aat                                            23

<210> SEQ ID NO 350
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 350
ugauuccaau gauguucucu u                                              21

<210> SEQ ID NO 351
<211> LENGTH: 21

```
<212> TYPE: RNA
<213> ORGANISM: Artificial Sequence
<220> FEATURE:
<223> OTHER INFORMATION: a synthetic siRNA sequence

<400> SEQUENCE: 351
guugugcuga acacagaaau u                                       21

<210> SEQ ID NO 352
<211> LENGTH: 23
<212> TYPE: DNA
<213> ORGANISM: homo sapiens

<400> SEQUENCE: 352
aggttgtgct gaacacagaa atg                                     23

<210> SEQ ID NO 353
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 353
uuucuguguu cagcacaacu u                                       21

<210> SEQ ID NO 354
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 354
gcuuucucuu ccacacaaau u                                       21

<210> SEQ ID NO 355
<211> LENGTH: 23
<212> TYPE: DNA
<213> ORGANISM: homo sapiens

<400> SEQUENCE: 355
ttgctttctc ttccacacaa aaa                                     23

<210> SEQ ID NO 356
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 356
uuugugugga agagaaagcu u                                       21

<210> SEQ ID NO 357
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 357
guuggugccu ucuugguauu u                                       21

<210> SEQ ID NO 358
```

```
<211> LENGTH: 23
<212> TYPE: DNA
<213> ORGANISM: homo sapiens

<400> SEQUENCE: 358
ctgttggtgc cttcttggta ttg                                              23

<210> SEQ ID NO 359
<211> LENGTH: 21
<212> TYPE: RNA
<213> ORGANISM: Artificial sequence
<220> FEATURE:
<223> OTHER INFORMATION: a synthetic siRNA sequence

<400> SEQUENCE: 359
auaccaagaa ggcaccaacu u                                                21

<210> SEQ ID NO 360
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 360
cuuggacauu ugguucuuau u                                                21

<210> SEQ ID NO 361
<211> LENGTH: 23
<212> TYPE: DNA
<213> ORGANISM: homo sapiens

<400> SEQUENCE: 361
ttcttggaca tttggttctt atc                                              23

<210> SEQ ID NO 362
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 362
uaagaaccaa auguccaagu u                                                21

<210> SEQ ID NO 363
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 363
ccugcugaaa cauuccaguu u                                                21

<210> SEQ ID NO 364
<211> LENGTH: 23
<212> TYPE: DNA
<213> ORGANISM: homo sapiens

<400> SEQUENCE: 364
ttcctgctga aacattccag tcc                                              23

<210> SEQ ID NO 365
<211> LENGTH: 21
```

```
<212> TYPE: RNA
<213> ORGANISM: Artificial Sequence
<220> FEATURE:
<223> OTHER INFORMATION: a synthetic siRNA sequence

<400> SEQUENCE: 365
acuggaaugu uucagcaggu u                                              21

<210> SEQ ID NO 366
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 366
ccaguagcuu ugagaagcuu u                                              21

<210> SEQ ID NO 367
<211> LENGTH: 23
<212> TYPE: DNA
<213> ORGANISM: homo sapiens

<400> SEQUENCE: 367
aaccagtagc tttgagaagc tac                                            23

<210> SEQ ID NO 368
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 368
agcuucucaa agcuacuggu u                                              21

<210> SEQ ID NO 369
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 369
ggucucaaau auucugucau u                                              21

<210> SEQ ID NO 370
<211> LENGTH: 23
<212> TYPE: DNA
<213> ORGANISM: homo sapiens

<400> SEQUENCE: 370
taggtctcaa atattctgtc aaa                                            23

<210> SEQ ID NO 371
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 371
ugacagaaua uuugagaccu u                                              21

<210> SEQ ID NO 372
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 372
gaacagaaau gcauuuguau u                                      21

<210> SEQ ID NO 373
<211> LENGTH: 23
<212> TYPE: DNA
<213> ORGANISM: homo sapiens

<400> SEQUENCE: 373
atgaacagaa atgcatttgt aat                                    23

<210> SEQ ID NO 374
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 374
uacaaaugca uuucuguucu u                                      21

<210> SEQ ID NO 375
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 375
guccuaacca agguaccuau u                                      21

<210> SEQ ID NO 376
<211> LENGTH: 23
<212> TYPE: DNA
<213> ORGANISM: homo sapiens

<400> SEQUENCE: 376
tggtcctaac caaggtacct atg                                    23

<210> SEQ ID NO 377
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 377
uagguaccuu gguuaggacu u                                      21

<210> SEQ ID NO 378
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 378
gcacucaaga aaguucugau u                                      21
```

```
<210> SEQ ID NO 379
<211> LENGTH: 23
<212> TYPE: DNA
<213> ORGANISM: homo sapiens

<400> SEQUENCE: 379
gagcactcaa gaaagttctg aaa                                              23

<210> SEQ ID NO 380
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 380
ucagaacuuu cuugagugcu u                                                21

<210> SEQ ID NO 381
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 381
caugaugggu cagaaacaau u                                                21

<210> SEQ ID NO 382
<211> LENGTH: 23
<212> TYPE: DNA
<213> ORGANISM: homo sapiens

<400> SEQUENCE: 382
gacatgatgg gtcagaaaca aat                                              23

<210> SEQ ID NO 383
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 383
uuguuucuga cccaucaugu u                                                21

<210> SEQ ID NO 384
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 384
caauggagaa uggguuauau u                                                21

<210> SEQ ID NO 385
<211> LENGTH: 23
<212> TYPE: DNA
<213> ORGANISM: homo sapiens

<400> SEQUENCE: 385
agcaatggag aatgggttat ata                                              23

<210> SEQ ID NO 386
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 386
uauaacccau ucuccauugu u                                             21

<210> SEQ ID NO 387
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 387
cucuauucuu gcccugaaau u                                             21

<210> SEQ ID NO 388
<211> LENGTH: 23
<212> TYPE: DNA
<213> ORGANISM: homo sapiens

<400> SEQUENCE: 388
atctctattc ttgccctgaa ata                                           23

<210> SEQ ID NO 389
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 389
uuucagggca agaauagagu u                                             21

<210> SEQ ID NO 390
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 390
cuucuaucuu cacauucauu u                                             21

<210> SEQ ID NO 391
<211> LENGTH: 23
<212> TYPE: DNA
<213> ORGANISM: homo sapiens

<400> SEQUENCE: 391
atcttctatc ttcacattca tgt                                           23

<210> SEQ ID NO 392
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 392
augaauguga agauagaagu u                                             21
```

```
<210> SEQ ID NO 393
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 393
guacuucagu gcaccuacuu u                                              21

<210> SEQ ID NO 394
<211> LENGTH: 23
<212> TYPE: DNA
<213> ORGANISM: homo sapiens

<400> SEQUENCE: 394
atgtacttca gtgcacctac tgc                                            23

<210> SEQ ID NO 395
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 395
aguaggugca cugaaguacu u                                              21

<210> SEQ ID NO 396
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 396
gaguuagaaa gguacuucuu u                                              21

<210> SEQ ID NO 397
<211> LENGTH: 23
<212> TYPE: DNA
<213> ORGANISM: homo sapiens

<400> SEQUENCE: 397
atgagttaga aaggtacttc tgt                                            23

<210> SEQ ID NO 398
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 398
agaaguaccu uucuaacucu u                                              21

<210> SEQ ID NO 399
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 399
gucacucugu aguuacuguu u                                              21
```

```
<210> SEQ ID NO 400
<211> LENGTH: 23
<212> TYPE: DNA
<213> ORGANISM: homo sapiens

<400> SEQUENCE: 400
gtgtcactct gtagttactg tgg                                          23

<210> SEQ ID NO 401
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 401
acaguaacua cagagugacu u                                            21

<210> SEQ ID NO 402
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 402
cacucaagaa aguucugaau u                                            21

<210> SEQ ID NO 403
<211> LENGTH: 23
<212> TYPE: DNA
<213> ORGANISM: homo sapiens

<400> SEQUENCE: 403
agcactcaag aaagttctga aac                                          23

<210> SEQ ID NO 404
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 404
uucagaacuu ucuugagugu u                                            21

<210> SEQ ID NO 405
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 405
gacacagaaa ugugacuguu u                                            21

<210> SEQ ID NO 406
<211> LENGTH: 23
<212> TYPE: DNA
<213> ORGANISM: homo sapiens

<400> SEQUENCE: 406
gggacacaga aatgtgactg tta                                          23
```

-continued

```
<210> SEQ ID NO 407
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 407
acagucacau uucugugucu u                                                 21

<210> SEQ ID NO 408
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 408
cacaugccua cgauugaaau u                                                 21

<210> SEQ ID NO 409
<211> LENGTH: 23
<212> TYPE: DNA
<213> ORGANISM: homo sapiens

<400> SEQUENCE: 409
gccacatgcc tacgattgaa atg                                               23

<210> SEQ ID NO 410
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 410
uuucaaucgu aggcaugugu u                                                 21

<210> SEQ ID NO 411
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 411
gacauuuggu gagagaaguu u                                                 21

<210> SEQ ID NO 412
<211> LENGTH: 23
<212> TYPE: DNA
<213> ORGANISM: homo sapiens

<400> SEQUENCE: 412
tcgacatttg gtgagagaag tac                                               23

<210> SEQ ID NO 413
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 413
acuucucuca ccaaaugucu u                                                 21
```

<210> SEQ ID NO 414
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 414
guccauugau auuggucuu u                                          21

<210> SEQ ID NO 415
<211> LENGTH: 23
<212> TYPE: DNA
<213> ORGANISM: homo sapiens

<400> SEQUENCE: 415
aagtccattg atatttggtc tgt                                       23

<210> SEQ ID NO 416
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 416
agaccaaaua ucaauggacu u                                         21

<210> SEQ ID NO 417
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 417
ccauauccuu ggcuacuaau u                                         21

<210> SEQ ID NO 418
<211> LENGTH: 23
<212> TYPE: DNA
<213> ORGANISM: homo sapiens

<400> SEQUENCE: 418
aaccatatcc ttggctacta aca                                       23

<210> SEQ ID NO 419
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 419
uuaguagcca aggauauggu u                                         21

<210> SEQ ID NO 420
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 420
cagcuguaaa guggaagcau u                                         21

```
<210> SEQ ID NO 421
<211> LENGTH: 23
<212> TYPE: DNA
<213> ORGANISM: homo sapiens

<400> SEQUENCE: 421
gtcagctgta aagtggaagc aat                                              23

<210> SEQ ID NO 422
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 422
ugcuuccacu uuacagcugu u                                                21

<210> SEQ ID NO 423
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 423
gcugaaacau uccagccuu u                                                 21

<210> SEQ ID NO 424
<211> LENGTH: 23
<212> TYPE: DNA
<213> ORGANISM: homo sapiens

<400> SEQUENCE: 424
ctgctgaaac attccagtcc ttt                                              23

<210> SEQ ID NO 425
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 425
aggacuggaa uguuucagcu u                                                21

<210> SEQ ID NO 426
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 426
cacaaucuua ggucucaaau u                                                21

<210> SEQ ID NO 427
<211> LENGTH: 23
<212> TYPE: DNA
<213> ORGANISM: homo sapiens

<400> SEQUENCE: 427
ttcacaatct taggtctcaa ata                                              23
```

```
<210> SEQ ID NO 428
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 428
uuugagaccu aagauugugu u                                              21

<210> SEQ ID NO 429
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 429
cugagucaga cugucagaau u                                              21

<210> SEQ ID NO 430
<211> LENGTH: 23
<212> TYPE: DNA
<213> ORGANISM: homo sapiens

<400> SEQUENCE: 430
tgctgagtca gactgtcaga aaa                                            23

<210> SEQ ID NO 431
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 431
uucugacagu cugacucagu u                                              21

<210> SEQ ID NO 432
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 432
gacuguuaca gcuuucuguu u                                              21

<210> SEQ ID NO 433
<211> LENGTH: 23
<212> TYPE: DNA
<213> ORGANISM: homo sapiens

<400> SEQUENCE: 433
atgactgtta cagctttctg tgc                                            23

<210> SEQ ID NO 434
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 434
acagaaagcu guaacagucu u                                              21
```

<210> SEQ ID NO 435
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 435
guacuucaaa gcaaguacuu u                                              21

<210> SEQ ID NO 436
<211> LENGTH: 23
<212> TYPE: DNA
<213> ORGANISM: homo sapiens

<400> SEQUENCE: 436
tagtacttca aagcaagtac tca                                            23

<210> SEQ ID NO 437
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 437
aguacuugcu uugaaguacu u                                              21

<210> SEQ ID NO 438
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 438
caugugguaa cuuguguuau u                                              21

<210> SEQ ID NO 439
<211> LENGTH: 23
<212> TYPE: DNA
<213> ORGANISM: homo sapiens

<400> SEQUENCE: 439
tgcatgtggt aacttgtgtt agg                                            23

<210> SEQ ID NO 440
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 440
uaacacaagu uaccacaugu u                                              21

<210> SEQ ID NO 441
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 441
ggaacuauuu gcuuucucuu u                                          21

<210> SEQ ID NO 442
<211> LENGTH: 23
<212> TYPE: DNA
<213> ORGANISM: homo sapiens

<400> SEQUENCE: 442
taggaactat ttgctttctc ttc                                        23

<210> SEQ ID NO 443
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 443
agagaaagca aauaguuccu u                                          21

<210> SEQ ID NO 444
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 444
gaucuuuaca agcucuugau u                                          21

<210> SEQ ID NO 445
<211> LENGTH: 23
<212> TYPE: DNA
<213> ORGANISM: homo sapiens

<400> SEQUENCE: 445
cagatcttta caagctcttg aag                                        23

<210> SEQ ID NO 446
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 446
ucaagagcuu guaaagaucu u                                          21

<210> SEQ ID NO 447
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 447
cagaugagaa gcuauaacau u                                          21

<210> SEQ ID NO 448
<211> LENGTH: 23
<212> TYPE: DNA
<213> ORGANISM: homo sapiens

<400> SEQUENCE: 448
tgcagatgag aagctataac agt                                        23

<210> SEQ ID NO 449
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 449
uguuauagcu ucucaucugu u                                              21

<210> SEQ ID NO 450
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 450
cucuggacuu auuggacaau u                                              21

<210> SEQ ID NO 451
<211> LENGTH: 23
<212> TYPE: DNA
<213> ORGANISM: homo sapiens

<400> SEQUENCE: 451
agctctggac ttattggaca aaa                                            23

<210> SEQ ID NO 452
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 452
uuguccaaua aguccagagu u                                              21

<210> SEQ ID NO 453
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 453
gcuuaugaua augucaacau u                                              21

<210> SEQ ID NO 454
<211> LENGTH: 23
<212> TYPE: DNA
<213> ORGANISM: homo sapiens

<400> SEQUENCE: 454
ctgcttatga taatgtcaac aaa                                            23

<210> SEQ ID NO 455
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 455

-continued

```
uguugacauu aucauaagcu u                          21

<210> SEQ ID NO 456
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 456
gcuuugagaa gcuacauguu u                          21

<210> SEQ ID NO 457
<211> LENGTH: 23
<212> TYPE: DNA
<213> ORGANISM: homo sapiens

<400> SEQUENCE: 457
tagctttgag aagctacatg tag                        23

<210> SEQ ID NO 458
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 458
acauguagcu ucucaaagcu u                          21

<210> SEQ ID NO 459
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 459
ccuacugcuu acuguugcuu u                          21

<210> SEQ ID NO 460
<211> LENGTH: 23
<212> TYPE: DNA
<213> ORGANISM: homo sapiens

<400> SEQUENCE: 460
cacctactgc ttactgttgc ttt                        23

<210> SEQ ID NO 461
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 461
agcaacagua agcaguaggu u                          21

<210> SEQ ID NO 462
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 462
```

| | |
|---|---|
| ccugaggauu uagcagagau u | 21 |

<210> SEQ ID NO 463
<211> LENGTH: 23
<212> TYPE: DNA
<213> ORGANISM: homo sapiens

<400> SEQUENCE: 463

| | |
|---|---|
| tgcctgagga tttagcagag agg | 23 |

<210> SEQ ID NO 464
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 464

| | |
|---|---|
| ucucugcuaa auccucaggu u | 21 |

<210> SEQ ID NO 465
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 465

| | |
|---|---|
| cauaucugga gcaguauuau u | 21 |

<210> SEQ ID NO 466
<211> LENGTH: 23
<212> TYPE: DNA
<213> ORGANISM: homo sapiens

<400> SEQUENCE: 466

| | |
|---|---|
| cccatatctg gagcagtatt acg | 23 |

<210> SEQ ID NO 467
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 467

| | |
|---|---|
| uaauacugcu ccagauaugu u | 21 |

<210> SEQ ID NO 468
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 468

| | |
|---|---|
| cacaacaccu cagcaaugau u | 21 |

<210> SEQ ID NO 469
<211> LENGTH: 23
<212> TYPE: DNA
<213> ORGANISM: homo sapiens

<400> SEQUENCE: 469

```
gacacaacac ctcagcaatg acc                                         23
```

<210> SEQ ID NO 470
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 470

```
ucauugcuga gguguugugu u                                           21
```

<210> SEQ ID NO 471
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 471

```
cuguugcuuu agucacuaau u                                           21
```

<210> SEQ ID NO 472
<211> LENGTH: 23
<212> TYPE: DNA
<213> ORGANISM: homo sapiens

<400> SEQUENCE: 472

```
tactgttgct ttagtcacta att                                         23
```

<210> SEQ ID NO 473
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 473

```
uuagugacua aagcaacagu u                                           21
```

<210> SEQ ID NO 474
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 474

```
caagaggauu gaaguagaau u                                           21
```

<210> SEQ ID NO 475
<211> LENGTH: 23
<212> TYPE: DNA
<213> ORGANISM: homo sapiens

<400> SEQUENCE: 475

```
cacaagagga ttgaagtaga aca                                         23
```

<210> SEQ ID NO 476
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 476
uucuacuuca auccucuugu u                                              21

<210> SEQ ID NO 477
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 477
gaguuguguu ccacggaaau u                                              21

<210> SEQ ID NO 478
<211> LENGTH: 23
<212> TYPE: DNA
<213> ORGANISM: homo sapiens

<400> SEQUENCE: 478
ctgagttgtg ttccacggaa aat                                            23

<210> SEQ ID NO 479
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 479
uuuccgugga acacaacucu u                                              21

<210> SEQ ID NO 480
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 480
cacuuggauu uacauaagau u                                              21

<210> SEQ ID NO 481
<211> LENGTH: 23
<212> TYPE: DNA
<213> ORGANISM: homo sapiens

<400> SEQUENCE: 481
agcacttgga tttacataag atg                                            23

<210> SEQ ID NO 482
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 482
ucuuauguaa auccaagugu u                                              21

<210> SEQ ID NO 483
<211> LENGTH: 21
<212> TYPE: RNA
<213> ORGANISM: Artificial Sequence
<220> FEATURE:
<223> OTHER INFORMATION: a synthetic siRNA sequence

```
<400> SEQUENCE: 483
gugucugaau ggacagucau u                                          21

<210> SEQ ID NO 484
<211> LENGTH: 23
<212> TYPE: DNA
<213> ORGANISM: homo sapiens

<400> SEQUENCE: 484
gcgtgtctga atggacagtc agg                                        23

<210> SEQ ID NO 485
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 485
ugacugucca uucagacacu u                                          21

<210> SEQ ID NO 486
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 486
cuugccuugu auaugguaau u                                          21

<210> SEQ ID NO 487
<211> LENGTH: 23
<212> TYPE: DNA
<213> ORGANISM: homo sapiens

<400> SEQUENCE: 487
tacttgcctt gtatatggta aag                                        23

<210> SEQ ID NO 488
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 488
uuaccauaua caaggcaagu u                                          21

<210> SEQ ID NO 489
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 489
gagaagcuau aacagugaau u                                          21

<210> SEQ ID NO 490
<211> LENGTH: 23
<212> TYPE: DNA
<213> ORGANISM: homo sapiens

<400> SEQUENCE: 490
```

```
atgagaagct ataacagtga ata                                           23
```

```
<210> SEQ ID NO 491
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 491
uucacuguua uagcuucucu u                                             21
```

```
<210> SEQ ID NO 492
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 492
cucaaagcua gcagagauau u                                             21
```

```
<210> SEQ ID NO 493
<211> LENGTH: 23
<212> TYPE: DNA
<213> ORGANISM: homo sapiens

<400> SEQUENCE: 493
tcctcaaagc tagcagagat acg                                           23
```

```
<210> SEQ ID NO 494
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 494
uaucucugcu agcuuugagu u                                             21
```

```
<210> SEQ ID NO 495
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 495
gugauuuggu uaaucuguau u                                             21
```

```
<210> SEQ ID NO 496
<211> LENGTH: 23
<212> TYPE: DNA
<213> ORGANISM: homo sapiens

<400> SEQUENCE: 496
ttgtgatttg gttaatctgt ata                                           23
```

```
<210> SEQ ID NO 497
<211> LENGTH: 21
<212> TYPE: RNA
<213> ORGANISM: Artificial Sequence
<220> FEATURE:
<223> OTHER INFORMATION: a synthetic siRNA sequence
```

```
<400> SEQUENCE: 497
uacagauuaa ccaaaucacu u                                              21

<210> SEQ ID NO 498
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 498
gcucuggacu uauuggacau u                                              21

<210> SEQ ID NO 499
<211> LENGTH: 23
<212> TYPE: DNA
<213> ORGANISM: homo sapiens

<400> SEQUENCE: 499
aagctctgga cttattggac aaa                                            23

<210> SEQ ID NO 500
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 500
uguccaauaa guccagagcu u                                              21

<210> SEQ ID NO 501
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 501
cacauacaua cgcacacauu u                                              21

<210> SEQ ID NO 502
<211> LENGTH: 23
<212> TYPE: DNA
<213> ORGANISM: homo sapiens

<400> SEQUENCE: 502
cacacataca tacgcacaca tgc                                            23

<210> SEQ ID NO 503
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 503
augugugcgu auguaugugu u                                              21

<210> SEQ ID NO 504
<211> LENGTH: 21
<212> TYPE: RNA
<213> ORGANISM: Artificial Sequence
<220> FEATURE:
<223> OTHER INFORMATION: a synthetic siRNA sequence
```

```
<400> SEQUENCE: 504
cacuugucaa gaagcguuau u                                              21

<210> SEQ ID NO 505
<211> LENGTH: 23
<212> TYPE: DNA
<213> ORGANISM: homo sapiens

<400> SEQUENCE: 505
aacacttgtc aagaagcgtt atg                                            23

<210> SEQ ID NO 506
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 506
uaacgcuucu ugacaagugu u                                              21

<210> SEQ ID NO 507
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 507
cugguuugaa agaugcaguu u                                              21

<210> SEQ ID NO 508
<211> LENGTH: 23
<212> TYPE: DNA
<213> ORGANISM: homo sapiens

<400> SEQUENCE: 508
ttctggtttg aaagatgcag tgg                                            23

<210> SEQ ID NO 509
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 509
acugcaucuu ucaaaccagu u                                              21

<210> SEQ ID NO 510
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 510
gucucugcuu ucuuccucuu u                                              21

<210> SEQ ID NO 511
<211> LENGTH: 23
<212> TYPE: DNA
<213> ORGANISM: homo sapiens
```

```
<400> SEQUENCE: 511
gcgtctctgc tttcttcctc tgc                                          23

<210> SEQ ID NO 512
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 512
agaggaagaa agcagagacu u                                            21

<210> SEQ ID NO 513
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 513
cucaguaaau agcaagucuu u                                            21

<210> SEQ ID NO 514
<211> LENGTH: 23
<212> TYPE: DNA
<213> ORGANISM: homo sapiens

<400> SEQUENCE: 514
tactcagtaa atagcaagtc ttt                                          23

<210> SEQ ID NO 515
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 515
agacuugcua uuuacugagu u                                            21

<210> SEQ ID NO 516
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 516
gaucucaaga ucugugacuu u                                            21

<210> SEQ ID NO 517
<211> LENGTH: 23
<212> TYPE: DNA
<213> ORGANISM: homo sapiens

<400> SEQUENCE: 517
gtgatctcaa gatctgtgac ttt                                          23

<210> SEQ ID NO 518
<211> LENGTH: 21
<212> TYPE: RNA
<213> ORGANISM: Artificial Sequence
<220> FEATURE:
<223> OTHER INFORMATION: a synthetic siRNA sequence
```

```
<400> SEQUENCE: 518
agucacagau cuugagaucu u                                              21

<210> SEQ ID NO 519
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 519
caucacaaga agaccugaau u                                              21

<210> SEQ ID NO 520
<211> LENGTH: 23
<212> TYPE: DNA
<213> ORGANISM: homo sapiens

<400> SEQUENCE: 520
cccatcacaa gaagacctga att                                            23

<210> SEQ ID NO 521
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 521
uucaggucuu cuugugaugu u                                              21

<210> SEQ ID NO 522
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 522
cucgacauuu ggugagagau u                                              21

<210> SEQ ID NO 523
<211> LENGTH: 23
<212> TYPE: DNA
<213> ORGANISM: homo sapiens

<400> SEQUENCE: 523
cactcgacat ttggtgagag aag                                            23

<210> SEQ ID NO 524
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 524
ucucucacca aaugucgagu u                                              21

<210> SEQ ID NO 525
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 525
guagagguaa ccaguagcuu u                                              21

<210> SEQ ID NO 526
<211> LENGTH: 23
<212> TYPE: DNA
<213> ORGANISM: homo sapiens

<400> SEQUENCE: 526
gtgtagaggt aaccagtagc ttt                                            23

<210> SEQ ID NO 527
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 527
agcuacuggu uaccucuacu u                                              21

<210> SEQ ID NO 528
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 528
gauaggauuu cuuggacauu u                                              21

<210> SEQ ID NO 529
<211> LENGTH: 23
<212> TYPE: DNA
<213> ORGANISM: homo sapiens

<400> SEQUENCE: 529
aagataggat ttcttggaca ttt                                            23

<210> SEQ ID NO 530
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 530
auguccaaga aauccuaucu u                                              21

<210> SEQ ID NO 531
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 531
caugaaacca cuaacuucau u                                              21

<210> SEQ ID NO 532
<211> LENGTH: 23
<212> TYPE: DNA
<213> ORGANISM: homo sapiens
```

```
<400> SEQUENCE: 532
ggcatgaaac cactaacttc att                                              23

<210> SEQ ID NO 533
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 533
ugaaguuagu gguuucaugu u                                                21

<210> SEQ ID NO 534
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 534
cauguuccuu uauucacaau u                                                21

<210> SEQ ID NO 535
<211> LENGTH: 23
<212> TYPE: DNA
<213> ORGANISM: homo sapiens

<400> SEQUENCE: 535
gtcatgttcc tttattcaca atc                                              23

<210> SEQ ID NO 536
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 536
uugugaauaa aggaacaugu u                                                21

<210> SEQ ID NO 537
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 537
guuaccggau aacacugauu u                                                21

<210> SEQ ID NO 538
<211> LENGTH: 23
<212> TYPE: DNA
<213> ORGANISM: homo sapiens

<400> SEQUENCE: 538
ctgttaccgg ataacactga tta                                              23

<210> SEQ ID NO 539
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 539
aucaguguua uccgguaacu u                                              21

<210> SEQ ID NO 540
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 540
gcauaguacu ucaaagcaau u                                              21

<210> SEQ ID NO 541
<211> LENGTH: 23
<212> TYPE: DNA
<213> ORGANISM: homo sapiens

<400> SEQUENCE: 541
cagcatagta cttcaaagca agt                                            23

<210> SEQ ID NO 542
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 542
uugcuuugaa guacuaugcu u                                              21

<210> SEQ ID NO 543
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 543
gacauggaau uggaugacuu u                                              21

<210> SEQ ID NO 544
<211> LENGTH: 23
<212> TYPE: DNA
<213> ORGANISM: homo sapiens

<400> SEQUENCE: 544
tcgacatgga attggatgac ttg                                            23

<210> SEQ ID NO 545
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 545
agucauccaa uuccaugucu u                                              21

<210> SEQ ID NO 546
<211> LENGTH: 21
<212> TYPE: RNA
<213> ORGANISM: Artificial Sequence
```

-continued

<220> FEATURE:
<223> OTHER INFORMATION: a synthetic siRNA sequence

<400> SEQUENCE: 546
gaagaauacu guauuguguu u                                              21

<210> SEQ ID NO 547
<211> LENGTH: 23
<212> TYPE: DNA
<213> ORGANISM: homo sapiens

<400> SEQUENCE: 547
tagaagaata ctgtattgtg tgt                                            23

<210> SEQ ID NO 548
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 548
acacaauaca guauucuucu u                                              21

<210> SEQ ID NO 549
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 549
gcuuuaguca cuaauugcuu u                                              21

<210> SEQ ID NO 550
<211> LENGTH: 23
<212> TYPE: DNA
<213> ORGANISM: homo sapiens

<400> SEQUENCE: 550
ttgctttagt cactaattgc ttt                                            23

<210> SEQ ID NO 551
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 551
agcaauuagu gacuaaagcu u                                              21

<210> SEQ ID NO 552
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 552
cacucgacau uuggugagau u                                              21

<210> SEQ ID NO 553
<211> LENGTH: 23
<212> TYPE: DNA

```
<213> ORGANISM: homo sapiens

<400> SEQUENCE: 553
ttcactcgac atttggtgag aga                                              23

<210> SEQ ID NO 554
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 554
ucucaccaaa ugucgagugu u                                                21

<210> SEQ ID NO 555
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 555
ggauuuacau aagaugaguu u                                                21

<210> SEQ ID NO 556
<211> LENGTH: 23
<212> TYPE: DNA
<213> ORGANISM: homo sapiens

<400> SEQUENCE: 556
ttggatttac ataagatgag tta                                              23

<210> SEQ ID NO 557
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 557
acucaucuua uguaaauccu u                                                21

<210> SEQ ID NO 558
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 558
gaagucauaa agauaggauu u                                                21

<210> SEQ ID NO 559
<211> LENGTH: 23
<212> TYPE: DNA
<213> ORGANISM: homo sapiens

<400> SEQUENCE: 559
aagaagtcat aaagatagga ttt                                              23

<210> SEQ ID NO 560
<211> LENGTH: 21
<212> TYPE: RNA
<213> ORGANISM: Artificial Sequence
```

```
<220> FEATURE:
<223> OTHER INFORMATION: a synthetic siRNA sequence

<400> SEQUENCE: 560
auccuaucuu uaugacuucu u                                             21

<210> SEQ ID NO 561
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 561
ggauaacacu gauuagucau u                                             21

<210> SEQ ID NO 562
<211> LENGTH: 23
<212> TYPE: DNA
<213> ORGANISM: homo sapiens

<400> SEQUENCE: 562
ccggataaca ctgattagtc agt                                           23

<210> SEQ ID NO 563
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 563
ugacuaauca guguuauccu u                                             21

<210> SEQ ID NO 564
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 564
guguugcuuu ccucuggauu u                                             21

<210> SEQ ID NO 565
<211> LENGTH: 23
<212> TYPE: DNA
<213> ORGANISM: homo sapiens

<400> SEQUENCE: 565
cagtgttgct ttcctctgga tca                                           23

<210> SEQ ID NO 566
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 566
auccagagga aagcaacacu u                                             21

<210> SEQ ID NO 567
<211> LENGTH: 21
<212> TYPE: RNA
```

```
<213> ORGANISM: Artificial Sequence
<220> FEATURE:
<223> OTHER INFORMATION: a synthetic siRNA sequence

<400> SEQUENCE: 567
cuagauucca gccaggauau u                                              21

<210> SEQ ID NO 568
<211> LENGTH: 23
<212> TYPE: DNA
<213> ORGANISM: homo sapiens

<400> SEQUENCE: 568
tgctagattc cagccaggat aca                                            23

<210> SEQ ID NO 569
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 569
uauccuggcu ggaaucuagu u                                              21

<210> SEQ ID NO 570
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 570
gugaauaugu gguuucucuu u                                              21

<210> SEQ ID NO 571
<211> LENGTH: 23
<212> TYPE: DNA
<213> ORGANISM: homo sapiens

<400> SEQUENCE: 571
cagtgaatat gtggtttctc tta                                            23

<210> SEQ ID NO 572
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 572
agagaaacca cauauucacu u                                              21

<210> SEQ ID NO 573
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 573
gacagaauau guggccacau u                                              21

<210> SEQ ID NO 574
<211> LENGTH: 23
```

```
<212> TYPE: DNA
<213> ORGANISM: homo sapiens

<400> SEQUENCE: 574
ctgacagaat atgtggccac acg                                                23

<210> SEQ ID NO 575
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 575
uguggccaca uauucugucu u                                                  21

<210> SEQ ID NO 576
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 576
gagaaguaca aagguugcau u                                                  21

<210> SEQ ID NO 577
<211> LENGTH: 23
<212> TYPE: DNA
<213> ORGANISM: homo sapiens

<400> SEQUENCE: 577
gagagaagta caaaggttgc agt                                                23

<210> SEQ ID NO 578
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 578
ugcaaccuuu guacuucucu u                                                  21

<210> SEQ ID NO 579
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 579
cagauccaga ccaugaucau u                                                  21

<210> SEQ ID NO 580
<211> LENGTH: 23
<212> TYPE: DNA
<213> ORGANISM: homo sapiens

<400> SEQUENCE: 580
tgcagatcca gaccatgatc aca                                                23

<210> SEQ ID NO 581
<211> LENGTH: 21
<212> TYPE: RNA
```

```
<213> ORGANISM: Artificial Sequence
<220> FEATURE:
<223> OTHER INFORMATION: a synthetic siRNA sequence

<400> SEQUENCE: 581
ugaucauggu cuggaucugu u                                              21

<210> SEQ ID NO 582
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 582
cacguaauau uucagccauu u                                              21

<210> SEQ ID NO 583
<211> LENGTH: 23
<212> TYPE: DNA
<213> ORGANISM: homo sapiens

<400> SEQUENCE: 583
gccacgtaat atttcagcca ttc                                            23

<210> SEQ ID NO 584
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 584
auggcugaaa uauuacgugu u                                              21

<210> SEQ ID NO 585
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 585
gugaucucaa gaucugugau u                                              21

<210> SEQ ID NO 586
<211> LENGTH: 23
<212> TYPE: DNA
<213> ORGANISM: homo sapiens

<400> SEQUENCE: 586
ctgtgatctc aagatctgtg act                                            23

<210> SEQ ID NO 587
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 587
ucacagaucu ugagaucacu u                                              21

<210> SEQ ID NO 588
<211> LENGTH: 21
```

```
<212> TYPE: RNA
<213> ORGANISM: Artificial Sequence
<220> FEATURE:
<223> OTHER INFORMATION: a synthetic siRNA sequence

<400> SEQUENCE: 588
cacacucauu ccuucugcuu u                                              21

<210> SEQ ID NO 589
<211> LENGTH: 23
<212> TYPE: DNA
<213> ORGANISM: homo sapiens

<400> SEQUENCE: 589
tgcacactca ttccttctgc tct                                            23

<210> SEQ ID NO 590
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 590
agcagaagga augagugugu u                                              21

<210> SEQ ID NO 591
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 591
caaagcaagu acucaguaau u                                              21

<210> SEQ ID NO 592
<211> LENGTH: 23
<212> TYPE: DNA
<213> ORGANISM: homo sapiens

<400> SEQUENCE: 592
ttcaaagcaa gtactcagta aat                                            23

<210> SEQ ID NO 593
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 593
uuacugagua cuugcuuugu u                                              21

<210> SEQ ID NO 594
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 594
caucuuucca gggaagcauu u                                              21

<210> SEQ ID NO 595
```

```
<211> LENGTH: 23
<212> TYPE: DNA
<213> ORGANISM: homo sapiens

<400> SEQUENCE: 595
cccatctttc caggaagca tta                                              23

<210> SEQ ID NO 596
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 596
augcuucccu ggaaagaugu u                                               21

<210> SEQ ID NO 597
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 597
gaacacagaa augcucacau u                                               21

<210> SEQ ID NO 598
<211> LENGTH: 23
<212> TYPE: DNA
<213> ORGANISM: homo sapiens

<400> SEQUENCE: 598
ctgaacacag aaatgctcac agg                                             23

<210> SEQ ID NO 599
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 599
ugugagcauu ucuguguucu u                                               21

<210> SEQ ID NO 600
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 600
cuacuaacau cuggagacuu u                                               21

<210> SEQ ID NO 601
<211> LENGTH: 23
<212> TYPE: DNA
<213> ORGANISM: homo sapiens

<400> SEQUENCE: 601
ggctactaac atctggagac tgt                                             23

<210> SEQ ID NO 602
<211> LENGTH: 21
```

```
<212> TYPE: RNA
<213> ORGANISM: Artificial Sequence
<220> FEATURE:
<223> OTHER INFORMATION: a synthetic siRNA sequence

<400> SEQUENCE: 602
agucuccaga uguuaguagu u                                              21

<210> SEQ ID NO 603
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 603
guucaaauaa gcuuucagau u                                              21

<210> SEQ ID NO 604
<211> LENGTH: 23
<212> TYPE: DNA
<213> ORGANISM: homo sapiens

<400> SEQUENCE: 604
atgttcaaat aagctttcag act                                            23

<210> SEQ ID NO 605
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 605
ucugaaagcu uauuugaacu u                                              21

<210> SEQ ID NO 606
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 606
gcaaugacca uaucugcuau u                                              21

<210> SEQ ID NO 607
<211> LENGTH: 23
<212> TYPE: DNA
<213> ORGANISM: homo sapiens

<400> SEQUENCE: 607
cagcaatgac catatctgct att                                            23

<210> SEQ ID NO 608
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 608
uagcagauau ggucauugcu u                                              21

<210> SEQ ID NO 609
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 609
cuuucuaaca ggcccaucuu u                                              21

<210> SEQ ID NO 610
<211> LENGTH: 23
<212> TYPE: DNA
<213> ORGANISM: homo sapiens

<400> SEQUENCE: 610
tgctttctaa caggcccatc ttt                                            23

<210> SEQ ID NO 611
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 611
agaugggccu guuagaaagu u                                              21

<210> SEQ ID NO 612
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 612
gauucagugu ugcuuuccuu u                                              21

<210> SEQ ID NO 613
<211> LENGTH: 23
<212> TYPE: DNA
<213> ORGANISM: homo sapiens

<400> SEQUENCE: 613
aagattcagt gttgctttcc tct                                            23

<210> SEQ ID NO 614
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 614
aggaaagcaa cacugaaucu u                                              21

<210> SEQ ID NO 615
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 615
ggaagcauua ucuugaccau u                                              21
```

```
<210> SEQ ID NO 616
<211> LENGTH: 23
<212> TYPE: DNA
<213> ORGANISM: homo sapiens

<400> SEQUENCE: 616
agggaagcat tatcttgacc agc                                              23

<210> SEQ ID NO 617
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 617
uggucaagau aaugcuuccu u                                                21

<210> SEQ ID NO 618
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 618
guacaaaggu ugcagugcuu u                                                21

<210> SEQ ID NO 619
<211> LENGTH: 23
<212> TYPE: DNA
<213> ORGANISM: homo sapiens

<400> SEQUENCE: 619
aagtacaaag gttgcagtgc tga                                              23

<210> SEQ ID NO 620
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 620
agcacugcaa ccuuuguacu u                                                21

<210> SEQ ID NO 621
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 621
caguauguua auacacacau u                                                21

<210> SEQ ID NO 622
<211> LENGTH: 23
<212> TYPE: DNA
<213> ORGANISM: homo sapiens

<400> SEQUENCE: 622
aacagtatgt taatacacac ata                                              23

<210> SEQ ID NO 623
```

```
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 623
uguguguauu aacauacugu u                                          21

<210> SEQ ID NO 624
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 624
gaaugguccu aaccaagguu u                                          21

<210> SEQ ID NO 625
<211> LENGTH: 23
<212> TYPE: DNA
<213> ORGANISM: homo sapiens

<400> SEQUENCE: 625
gagaatggtc ctaaccaagg tac                                        23

<210> SEQ ID NO 626
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 626
accuugguua ggaccauucu u                                          21

<210> SEQ ID NO 627
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 627
ccauugauau uuggucuguu u                                          21

<210> SEQ ID NO 628
<211> LENGTH: 23
<212> TYPE: DNA
<213> ORGANISM: homo sapiens

<400> SEQUENCE: 628
gtccattgat atttggtctg tag                                        23

<210> SEQ ID NO 629
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 629
acagaccaaa uaucaauggu u                                          21
```

```
<210> SEQ ID NO 630
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 630
ccaauuggcu cuagucacuu u                                             21

<210> SEQ ID NO 631
<211> LENGTH: 23
<212> TYPE: DNA
<213> ORGANISM: homo sapiens

<400> SEQUENCE: 631
ccccaattgg ctctagtcac tgg                                           23

<210> SEQ ID NO 632
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 632
agugacuaga gccaauuggu u                                             21

<210> SEQ ID NO 633
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 633
ccacguaaua uuucagccau u                                             21

<210> SEQ ID NO 634
<211> LENGTH: 23
<212> TYPE: DNA
<213> ORGANISM: homo sapiens

<400> SEQUENCE: 634
tgccacgtaa tatttcagcc att                                           23

<210> SEQ ID NO 635
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 635
uggcugaaau auuacguggu u                                             21

<210> SEQ ID NO 636
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 636
cuuacgucau ccaccuugau u                                             21
```

<210> SEQ ID NO 637
<211> LENGTH: 23
<212> TYPE: DNA
<213> ORGANISM: homo sapiens

<400> SEQUENCE: 637
ctcttacgtc atccaccttg aca                                              23

<210> SEQ ID NO 638
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 638
ucaaggugga ugacguaagu u                                                21

<210> SEQ ID NO 639
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 639
caugagaaca ucauuggaau u                                                21

<210> SEQ ID NO 640
<211> LENGTH: 23
<212> TYPE: DNA
<213> ORGANISM: homo sapiens

<400> SEQUENCE: 640
gacatgagaa catcattgga atc                                              23

<210> SEQ ID NO 641
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 641
uuccaaugau guucucaugu u                                                21

<210> SEQ ID NO 642
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 642
cuguucccaa augcugacuu u                                                21

<210> SEQ ID NO 643
<211> LENGTH: 23
<212> TYPE: DNA
<213> ORGANISM: homo sapiens

<400> SEQUENCE: 643
ggctgttccc aaatgctgac tcc                                              23

```
<210> SEQ ID NO 644
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 644
agucagcauu ugggaacagu u                                              21

<210> SEQ ID NO 645
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 645
caacaaaguu cgaguagcuu u                                              21

<210> SEQ ID NO 646
<211> LENGTH: 23
<212> TYPE: DNA
<213> ORGANISM: homo sapiens

<400> SEQUENCE: 646
gtcaacaaag ttcgagtagc tat                                            23

<210> SEQ ID NO 647
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 647
agcuacucga acuuuguugu u                                              21

<210> SEQ ID NO 648
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 648
gaagcaauau uacuugccuu u                                              21

<210> SEQ ID NO 649
<211> LENGTH: 23
<212> TYPE: DNA
<213> ORGANISM: homo sapiens

<400> SEQUENCE: 649
tggaagcaat attacttgcc ttg                                            23

<210> SEQ ID NO 650
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 650
aggcaaguaa uauugcuucu u                                              21
```

```
<210> SEQ ID NO 651
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 651
guucuucaga ccuucaccuu u                                              21

<210> SEQ ID NO 652
<211> LENGTH: 23
<212> TYPE: DNA
<213> ORGANISM: homo sapiens

<400> SEQUENCE: 652
tggttcttca gaccttcacc tgt                                            23

<210> SEQ ID NO 653
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 653
aggugaaggu cugaagaacu u                                              21

<210> SEQ ID NO 654
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 654
cucacuuuau gauagggaau u                                              21

<210> SEQ ID NO 655
<211> LENGTH: 23
<212> TYPE: DNA
<213> ORGANISM: homo sapiens

<400> SEQUENCE: 655
atctcacttt atgataggga agg                                            23

<210> SEQ ID NO 656
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 656
uucccuauca uaaagugagu u                                              21

<210> SEQ ID NO 657
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 657
guuuggagcu cuauccauau u                                              21
```

-continued

<210> SEQ ID NO 658
<211> LENGTH: 23
<212> TYPE: DNA
<213> ORGANISM: homo sapiens

<400> SEQUENCE: 658
gtgtttggag ctctatccat att                                              23

<210> SEQ ID NO 659
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 659
uauggauaga gcuccaaacu u                                                21

<210> SEQ ID NO 660
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 660
caguagcuuu gagaagcuau u                                                21

<210> SEQ ID NO 661
<211> LENGTH: 23
<212> TYPE: DNA
<213> ORGANISM: homo sapiens

<400> SEQUENCE: 661
accagtagct ttgagaagct aca                                              23

<210> SEQ ID NO 662
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 662
uagcuucuca aagcuacugu u                                                21

<210> SEQ ID NO 663
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 663
gaaguacaaa gguugcaguu u                                                21

<210> SEQ ID NO 664
<211> LENGTH: 23
<212> TYPE: DNA
<213> ORGANISM: homo sapiens

<400> SEQUENCE: 664
gagaagtaca aaggttgcag tgc                                              23

<210> SEQ ID NO 665
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 665
acugcaaccu uuguacuucu u                                              21

<210> SEQ ID NO 666
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 666
cuuccagauu ugcucugcau u                                              21

<210> SEQ ID NO 667
<211> LENGTH: 23
<212> TYPE: DNA
<213> ORGANISM: homo sapiens

<400> SEQUENCE: 667
gtcttccaga tttgctctgc atg                                            23

<210> SEQ ID NO 668
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 668
ugcagagcaa aucuggaagu u                                              21

<210> SEQ ID NO 669
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 669
caauauuacu ugccuuguau u                                              21

<210> SEQ ID NO 670
<211> LENGTH: 23
<212> TYPE: DNA
<213> ORGANISM: homo sapiens

<400> SEQUENCE: 670
agcaatatta cttgccttgt ata                                            23

<210> SEQ ID NO 671
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 671
uacaaggcaa guaauauugu u                                              21

<210> SEQ ID NO 672
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 672
gaaagaugca gugguuccuu u                                              21

<210> SEQ ID NO 673
<211> LENGTH: 23
<212> TYPE: DNA
<213> ORGANISM: homo sapiens

<400> SEQUENCE: 673
ttgaaagatg cagtggttcc tcc                                            23

<210> SEQ ID NO 674
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 674
aggaaccacu gcaucuuucu u                                              21

<210> SEQ ID NO 675
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 675
caaugaccau aucugcuauu u                                              21

<210> SEQ ID NO 676
<211> LENGTH: 23
<212> TYPE: DNA
<213> ORGANISM: homo sapiens

<400> SEQUENCE: 676
agcaatgacc atatctgcta ttt                                            23

<210> SEQ ID NO 677
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 677
auagcagaua uggucauugu u                                              21

<210> SEQ ID NO 678
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 678

-continued

```
gaaauaccuu ggcugauguu u                                              21
```

<210> SEQ ID NO 679
<211> LENGTH: 23
<212> TYPE: DNA
<213> ORGANISM: homo sapiens

<400> SEQUENCE: 679

```
tggaaatacc ttggctgatg ttg                                            23
```

<210> SEQ ID NO 680
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 680

```
acaucagcca agguauuucu u                                              21
```

<210> SEQ ID NO 681
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 681

```
cuugacauga ugggucagau u                                              21
```

<210> SEQ ID NO 682
<211> LENGTH: 23
<212> TYPE: DNA
<213> ORGANISM: homo sapiens

<400> SEQUENCE: 682

```
accttgacat gatgggtcag aaa                                            23
```

<210> SEQ ID NO 683
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 683

```
ucugacccau caugucaagu u                                              21
```

<210> SEQ ID NO 684
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 684

```
cuagaaucau uguagccauu u                                              21
```

<210> SEQ ID NO 685
<211> LENGTH: 23
<212> TYPE: DNA
<213> ORGANISM: homo sapiens

<400> SEQUENCE: 685

```
ttctagaatc attgtagcca taa                                            23
```

<210> SEQ ID NO 686
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 686
auggcuacaa ugauucuagu u                                              21

<210> SEQ ID NO 687
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 687
guaaccagua gcuuugagau u                                              21

<210> SEQ ID NO 688
<211> LENGTH: 23
<212> TYPE: DNA
<213> ORGANISM: homo sapiens

<400> SEQUENCE: 688
aggtaaccag tagctttgag aag                                            23

<210> SEQ ID NO 689
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 689
ucucaaagcu acugguuacu u                                              21

<210> SEQ ID NO 690
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 690
cuacuucaaa ugggguguu u                                               21

<210> SEQ ID NO 691
<211> LENGTH: 23
<212> TYPE: DNA
<213> ORGANISM: homo sapiens

<400> SEQUENCE: 691
agctacttca aatgtgggtg ttt                                            23

<210> SEQ ID NO 692
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 692

-continued acacccacau uugaaguagu u                                    21

<210> SEQ ID NO 693
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 693
cauugauauu uggucuguau u                                    21

<210> SEQ ID NO 694
<211> LENGTH: 23
<212> TYPE: DNA
<213> ORGANISM: homo sapiens

<400> SEQUENCE: 694
tccattgata tttggtctgt agg                                  23

<210> SEQ ID NO 695
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 695
uacagaccaa auaucaaugu u                                    21

<210> SEQ ID NO 696
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 696
guuucucuua cgucauccau u                                    21

<210> SEQ ID NO 697
<211> LENGTH: 23
<212> TYPE: DNA
<213> ORGANISM: homo sapiens

<400> SEQUENCE: 697
tggtttctct tacgtcatcc acc                                  23

<210> SEQ ID NO 698
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 698
uggaugacgu aagagaaacu u                                    21

<210> SEQ ID NO 699
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 699

```
guguuaugga aagagcacau u                                                 21

<210> SEQ ID NO 700
<211> LENGTH: 23
<212> TYPE: DNA
<213> ORGANISM: homo sapiens

<400> SEQUENCE: 700
tggtgttatg gaaagagcac agg                                               23

<210> SEQ ID NO 701
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 701
ugugcucuuu ccauaacacu u                                                 21

<210> SEQ ID NO 702
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 702
gguuauauaa agacugccuu u                                                 21

<210> SEQ ID NO 703
<211> LENGTH: 23
<212> TYPE: DNA
<213> ORGANISM: homo sapiens

<400> SEQUENCE: 703
tgggttatat aaagactgcc tgc                                               23

<210> SEQ ID NO 704
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 704
aggcagucuu uauauaaccu u                                                 21

<210> SEQ ID NO 705
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 705
ggaauuggau gacuugccuu u                                                 21

<210> SEQ ID NO 706
<211> LENGTH: 23
<212> TYPE: DNA
<213> ORGANISM: homo sapiens

<400> SEQUENCE: 706
```

-continued atggaattgg atgacttgcc taa    23

<210> SEQ ID NO 707
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 707
aggcaaguca uccaauuccu u    21

<210> SEQ ID NO 708
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 708
cauucaaguu cgacauggau u    21

<210> SEQ ID NO 709
<211> LENGTH: 23
<212> TYPE: DNA
<213> ORGANISM: homo sapiens

<400> SEQUENCE: 709
accattcaag ttcgacatgg aat    23

<210> SEQ ID NO 710
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 710
uccaugucga acuugaaugu u    21

<210> SEQ ID NO 711
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 711
guuugaaaga ugcagugguu u    21

<210> SEQ ID NO 712
<211> LENGTH: 23
<212> TYPE: DNA
<213> ORGANISM: homo sapiens

<400> SEQUENCE: 712
tggtttgaaa gatgcagtgg ttc    23

<210> SEQ ID NO 713
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 713
accacugcau cuuucaaacu u                                              21

<210> SEQ ID NO 714
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 714
gaauguuuau ggcaccugau u                                              21

<210> SEQ ID NO 715
<211> LENGTH: 23
<212> TYPE: DNA
<213> ORGANISM: homo sapiens

<400> SEQUENCE: 715
ttgaatgttt atggcacctg act                                            23

<210> SEQ ID NO 716
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 716
ucaggugcca uaaacauucu u                                              21

<210> SEQ ID NO 717
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 717
caaauaagcu uucagacuau u                                              21

<210> SEQ ID NO 718
<211> LENGTH: 23
<212> TYPE: DNA
<213> ORGANISM: homo sapiens

<400> SEQUENCE: 718
ttcaaataag ctttcagact aat                                            23

<210> SEQ ID NO 719
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 719
uagucugaaa gcuuauuugu u                                              21

<210> SEQ ID NO 720
<211> LENGTH: 21
<212> TYPE: RNA
<213> ORGANISM: Artificial Sequence
<220> FEATURE:
<223> OTHER INFORMATION: a synthetic siRNA sequence

```
<400> SEQUENCE: 720
cuaaucauga ggacucuguu u                                              21

<210> SEQ ID NO 721
<211> LENGTH: 23
<212> TYPE: DNA
<213> ORGANISM: homo sapiens

<400> SEQUENCE: 721
aactaatcat gaggactctg tcc                                            23

<210> SEQ ID NO 722
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 722
acagaguccu caugauuagu u                                              21

<210> SEQ ID NO 723
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 723
gguaacuugu guuagggcuu u                                              21

<210> SEQ ID NO 724
<211> LENGTH: 23
<212> TYPE: DNA
<213> ORGANISM: homo sapiens

<400> SEQUENCE: 724
gtggtaactt gtgttagggc tgt                                            23

<210> SEQ ID NO 725
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 725
agcccuaaca caaguuaccu u                                              21

<210> SEQ ID NO 726
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 726
cauuucaacu guucagcauu u                                              21

<210> SEQ ID NO 727
<211> LENGTH: 23
<212> TYPE: DNA
<213> ORGANISM: homo sapiens

<400> SEQUENCE: 727
```

```
tacatttcaa ctgttcagca tag                                                    23
```

<210> SEQ ID NO 728
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 728

```
augcugaaca guugaaaugu u                                                      21
```

<210> SEQ ID NO 729
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 729

```
gauugaagua gaacaggcuu u                                                      21
```

<210> SEQ ID NO 730
<211> LENGTH: 23
<212> TYPE: DNA
<213> ORGANISM: homo sapiens

<400> SEQUENCE: 730

```
aggattgaag tagaacaggc tct                                                    23
```

<210> SEQ ID NO 731
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 731

```
agccuguucu acuucaaucu u                                                      21
```

<210> SEQ ID NO 732
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 732

```
cuauuugcuu ucucuuccau u                                                      21
```

<210> SEQ ID NO 733
<211> LENGTH: 23
<212> TYPE: DNA
<213> ORGANISM: homo sapiens

<400> SEQUENCE: 733

```
aactatttgc tttctcttcc aca                                                    23
```

<210> SEQ ID NO 734
<211> LENGTH: 21
<212> TYPE: RNA
<213> ORGANISM: Artificial Sequence
<220> FEATURE:
<223> OTHER INFORMATION: a synthetic siRNA sequence

```
<400> SEQUENCE: 734
uggaagagaa agcaaauagu u                                              21

<210> SEQ ID NO 735
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 735
cugacagaau auguggccau u                                              21

<210> SEQ ID NO 736
<211> LENGTH: 23
<212> TYPE: DNA
<213> ORGANISM: homo sapiens

<400> SEQUENCE: 736
tcctgacaga atatgtggcc aca                                            23

<210> SEQ ID NO 737
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 737
uggccacaua uucugucagu u                                              21

<210> SEQ ID NO 738
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 738
gauuugcucu gcaugugguu u                                              21

<210> SEQ ID NO 739
<211> LENGTH: 23
<212> TYPE: DNA
<213> ORGANISM: homo sapiens

<400> SEQUENCE: 739
cagatttgct ctgcatgtgg taa                                            23

<210> SEQ ID NO 740
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 740
accacaugca gagcaaaucu u                                              21

<210> SEQ ID NO 741
<211> LENGTH: 21
<212> TYPE: RNA
<213> ORGANISM: Artificial Sequence
<220> FEATURE:
<223> OTHER INFORMATION: a synthetic siRNA sequence
```

-continued

<400> SEQUENCE: 741
guuucuggua guuguggcuu u                                              21

<210> SEQ ID NO 742
<211> LENGTH: 23
<212> TYPE: DNA
<213> ORGANISM: homo sapiens

<400> SEQUENCE: 742
cggtttctgg tagttgtggc ttt                                            23

<210> SEQ ID NO 743
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 743
agccacaacu accagaaacu u                                              21

<210> SEQ ID NO 744
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 744
gaaauccaga gcaaguccuu u                                              21

<210> SEQ ID NO 745
<211> LENGTH: 23
<212> TYPE: DNA
<213> ORGANISM: homo sapiens

<400> SEQUENCE: 745
tggaaatcca gagcaagtcc tcc                                            23

<210> SEQ ID NO 746
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 746
aggacuugcu cuggauuucu u                                              21

<210> SEQ ID NO 747
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 747
gauauuuggu cuguaggcuu u                                              21

<210> SEQ ID NO 748
<211> LENGTH: 23
<212> TYPE: DNA
<213> ORGANISM: homo sapiens

```
<400> SEQUENCE: 748
ttgatatttg gtctgtaggc tgc                                             23

<210> SEQ ID NO 749
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 749
agccuacaga ccaaauaucu u                                               21

<210> SEQ ID NO 750
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 750
caaugacauu auucgagcau u                                               21

<210> SEQ ID NO 751
<211> LENGTH: 23
<212> TYPE: DNA
<213> ORGANISM: homo sapiens

<400> SEQUENCE: 751
atcaatgaca ttattcgagc acc                                             23

<210> SEQ ID NO 752
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 752
ugcucgaaua augcauugu u                                                21

<210> SEQ ID NO 753
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 753
cuuauccacu uugacuccuu u                                               21

<210> SEQ ID NO 754
<211> LENGTH: 23
<212> TYPE: DNA
<213> ORGANISM: homo sapiens

<400> SEQUENCE: 754
ggcttatcca ctttgactcc ttt                                             23

<210> SEQ ID NO 755
<211> LENGTH: 21
<212> TYPE: RNA
<213> ORGANISM: Artificial Sequence
<220> FEATURE:
<223> OTHER INFORMATION: a synthetic siRNA sequence
```

```
<400> SEQUENCE: 755
aggagucaaa guggauaagu u                                              21

<210> SEQ ID NO 756
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 756
cauaauguaa cugggcagau u                                              21

<210> SEQ ID NO 757
<211> LENGTH: 23
<212> TYPE: DNA
<213> ORGANISM: homo sapiens

<400> SEQUENCE: 757
aacataatgt aactgggcag aga                                            23

<210> SEQ ID NO 758
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 758
ucugcccagu uacauuaugu u                                              21

<210> SEQ ID NO 759
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 759
caaauggaaa uccagagcau u                                              21

<210> SEQ ID NO 760
<211> LENGTH: 23
<212> TYPE: DNA
<213> ORGANISM: homo sapiens

<400> SEQUENCE: 760
aacaaatgga aatccagagc aag                                            23

<210> SEQ ID NO 761
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 761
ugcucuggau uuccauuugu u                                              21

<210> SEQ ID NO 762
<211> LENGTH: 21
<212> TYPE: RNA
<213> ORGANISM: Artificial Sequence
<220> FEATURE:
```

```
<223> OTHER INFORMATION: a synthetic siRNA sequence

<400> SEQUENCE: 762
cuuuaugaua gggaaggcuu u                                              21

<210> SEQ ID NO 763
<211> LENGTH: 23
<212> TYPE: DNA
<213> ORGANISM: homo sapiens

<400> SEQUENCE: 763
cactttatga tagggaaggc tac                                            23

<210> SEQ ID NO 764
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 764
agccuucccu aucauaaagu u                                              21

<210> SEQ ID NO 765
<211> LENGTH: 19
<212> TYPE: DNA
<213> ORGANISM: mus musculus

<400> SEQUENCE: 765
ggaacaggtt gttcccaaa                                                 19

<210> SEQ ID NO 766
<211> LENGTH: 9
<212> TYPE: DNA
<213> ORGANISM: Artificial Sequence
<220> FEATURE:
<223> OTHER INFORMATION: a synthetic oligonucleotide sequence

<400> SEQUENCE: 766 ttcaagaga                                                             9

<210> SEQ ID NO 767
<211> LENGTH: 19
<212> TYPE: DNA
<213> ORGANISM: mus musculus

<400> SEQUENCE: 767
tttgggaaca acctgttcc                                                 19

<210> SEQ ID NO 768
<211> LENGTH: 47
<212> TYPE: DNA
<213> ORGANISM: Artificial Sequence
<220> FEATURE:
<223> OTHER INFORMATION: a synthetic oligonucleotide sequence

<400> SEQUENCE: 768
ggaacaggtt gttcccaaat tcaagagatt tgggacaac ctgttcc                   47

<210> SEQ ID NO 769
<211> LENGTH: 19
<212> TYPE: DNA
<213> ORGANISM: mus musculus

<400> SEQUENCE: 769
```

-continued

| | |
|---|---|
| ggagcagtat tatgaccca | 19 |

<210> SEQ ID NO 770
<211> LENGTH: 19
<212> TYPE: DNA
<213> ORGANISM: mus musculus

<400> SEQUENCE: 770

| | |
|---|---|
| gactgctaga ttccagcca | 19 |

<210> SEQ ID NO 771
<211> LENGTH: 5099
<212> TYPE: DNA
<213> ORGANISM: mus musculus

<400> SEQUENCE: 771

| | |
|---|---|
| gacgcgaacc cttccctcct cccactcgta gcccgcccgt caggcaggaa ggctggcagt | 60 |
| ggttctaccg gcggttaatt ctctcctctg tgttgtcctc cttcctcgtt cccgatcgcc | 120 |
| ggcgggggcg gctacacggg cggcagcgcg gttcctgcgg gaagcgcagc ataagtcgag | 180 |
| cggcagccgc gaagcgtcga accgaacgcg cggcggcgg cggcggcggc ggctgtgcag | 240 |
| ccaacatggc ggcggcggcg gcggcgggcc cggagatggt ccgcgggcag gtgttcgacg | 300 |
| tagggccgcg ctacaccaac ctctcgtaca tcggagaagg cgcctacggc atggtttgct | 360 |
| ctgcttatga taatctcaac aaagttcgag ttgctatcaa gaaaatcagt ccttttgagc | 420 |
| accagaccta ctgtcaaaga accctaagag agataaaaat cttactgcgc ttcagacatg | 480 |
| agaacatcat tggcatcaat gacatcatcc gggcaccaac cattgagcaa atgaaagatg | 540 |
| tatatatagt acaggacctc atggagacgg acctttacaa gctcttgaag acacagcacc | 600 |
| tcagcaatga ccacatctgc tattttcttt atcagatcct gagagggcta aagtatatcc | 660 |
| attcagctaa cgttctgcac cgtgacctca agccttccaa cctcctgctg aacaccactt | 720 |
| gtgatctcaa gatctgtgac tttggccttg cccgtgttgc agatccagat catgatcaca | 780 |
| cagggttctt gacagagtac gtagccacac gttggtacag agctccagaa attatgttga | 840 |
| attccaaggg ttataccaag tccattgata tttggtctgt gggctgcatc ctggcagaga | 900 |
| tgctatccaa caggcctatc ttcccaggaa agcattacct tgaccagctg aatcacatcc | 960 |
| tgggtattct tggatctcca tcacaggaag atctgaattg tataataaat ttaaaagcta | 1020 |
| gaaactattt gctttctctc ccgcacaaaa ataaggtgcc atggaacagg ttgttcccaa | 1080 |
| atgctgactc caaagctctg gatttactgg ataaaatgtt gacatttaac cctcacaaga | 1140 |
| ggattgaagt tgaacaggct ctggcccacc catacctgga gcagtattat gacccaagtg | 1200 |
| atgagcccat tgctgaagcg ccattcaagt ttgacatgga gttggacgac ttacctaagg | 1260 |
| agaagctcaa agaactcatt tttgaagaga ctgctagatt ccagccagga tacagatctt | 1320 |
| aaattggtca ggacaagggc tcagaggact ggacagagttc agatgtcggt gtccccccag | 1380 |
| ttctttaccc tggtcctgtc ttcagcccgt ctcagcttac ccactcttga ctccttttgag | 1440 |
| cctttcagag gggcagtttc tggtagtagc agctttttata cttttcacgga attccttcag | 1500 |
| tccagagagt tctggcagca ggccgtgcag cagtgtgcac tttcaatgca cttaactgct | 1560 |
| tactgttgtt tagtcacgaa ctgctttctg gtttgaaaga tgcagtggtt cctccctgtt | 1620 |
| ctgaatcctt tctccatatc atgtgctgaa ccatcagcct catcagaggg agagtctttc | 1680 |
| cagacttgtt ccagttactg gcacctcact tcacagtagg gaggctagga cataaggcac | 1740 |

```
cttaagtcag tgacagctcc aaatttgcac ttcatctgtt ggctagtaac tgtctaccta   1800
gacagtagga gcttgtgggt atccctggat ggtattacag gctacagggg caggggcttc   1860
tgttgcagga gtcctttggg gctatttttcc tgtgtatcat gttagtccta aatttaaggt   1920
atgtactatt tgcccagctt tttaaaaatt tgatcattgt ttaaatgaaa taggaaggaa   1980
gcattgcacc agcagtatct gttgttctgc agattttata tggttacttg tatcgtaatg   2040
gaggtggagc tcttgccaaa atgttacatg ctatccttag ccagagagtg aaagtaacag   2100
ctgtgcttgt catttactga aaggtggaca cacacaaagc tgtggaagtt tccagaacag   2160
tagagagcaa gctgacctag atgttcaggg cagagctcca tataaccttg aacagccaca   2220
cagaaggctg tttgcgtaac cacattcact acctagggat ttagctaaaa ggaacactgc   2280
atctttaaat gagaaagtgt acagttcttc tcctgcagca tgtcagcatc tcgagctcac   2340
ttttcagcag tgtaatgact tgtatgtaat aaagccttga tgggctctcc tcatgaagct   2400
ctgctctgtt gccaagttag agatgtttct ggtactgctg agttaatgtc ataaaaggct   2460
agcagtaact gttcgagctc tcttttattt ccttctctcc tatattttgt tcctgcactg   2520
tgtgctgtgg agttgatggt gttatcccag tgcggtgcct ccagaccccc tcactgctct   2580
ctgatgagaa atatgccttg ttcaatactt actgtgctct tgcatgactg ttaaggtttc   2640
tgtgcagaga ccaatgtcca agtgtcacat cctttgattg aacgaaatct gttgtgacct   2700
ctgagttgta ttccatgaag agaatgctac ccagaagata atgtagaaaa gataattata   2760
ttgttaactt ttcatttctc agctgtcctt ttgttttctt ggttttatt ttttattttg   2820 acatcaatgg aaaatgggtt ctataaagac tgcctgctag tatgaacagc aatgcaatgc   2880
acttgtaact catggaaata aatgtacatc tttatcttta cacccatgat aagattcagt   2940
gttgattttc tctggattgg tgtgtcctaa gtaggcactc ataatcaatt tatggcttgt   3000
gcttcagaca aaaatgttca tgggccttac tctacttctc cccactccac cctacccccc   3060
atgcactgcc cctcacagca gtttacgtat atggctggga aagtcctttt tcagctgcac   3120
atggtgccat gcatcgttaa tcccagcatt cagaagtcag aggcaggtgg atctctgaat   3180
ggaagcaggc ctgatttgca tagggaggtc caagacagct ggaactctat aggtcctgtc   3240
tcaaaaaaaa cagagtcctc cccgtctgcc tctcagcagc aaatgaatct gacatgatcc   3300
tctctaaaac aggtctcaag tagtcagatg ttgatgatgg cacccaaaca tgcccaagtt   3360
aggatctggt tccctctgaa aagggccttc ttgcctctgt atcctagagc tgtaggaagg   3420
gctgttcaag atctcatgta cctgctacca agttcaaggt agcacatacc tcacctggct   3480
aaagaatggc tgactcatcc cagaaaccag atctcagttc ttggcctaaa tccctgcttt   3540
tcacttccac acatgaagcc cactggcatt gaaggaatag aggttcagct ttcattgata   3600
cagtagtggt cagttttcct ttttcttttt gtctttttt ttaaagcact gactgttctc   3660
ctacttgttt ctttttcata ttttttaatcc catgagatta atttgcattc ttgtgaataa   3720
ggaaaccata gcctcatctt ctcgaggtct gagctttctg cccttcctgg cactgtggag   3780
aggggttggt gtgagatcac tcacttcatc ctagtcactg tatcacaagt gtggctttca   3840
tgtagccatt gtaaatgaca gctcagagct gtcaggtata gaaacgctca ttattttggt   3900
tctcatgttt ctaaaaatgt ttggataacg tcatctgcat actggtgtca ttgggtgcct   3960
ctactattca tacacataga taagctgtct ggtggatggg cttttgtcc aagtcttaat   4020 atgtgaggga aaaaaaccca aaaacatgaa aacatttagc atgaagaaga tagctatcca   4080
acaatcccag agcgcttgat gataccggca ttcagagctg acactgacct actctgtggt   4140
```

```
gcatttattc tgcccccacc ctcatccctc tcatttgagg acaggcaaca cttgggctgg    4200
gcatgactgt tagttttggg aagctgtgaa ttaacagcag ctatctctga ggaatcacaa    4260
aggtagacac ctacactgca tgccacatag tattcagacc acttagggag acttccattt    4320
gcttaggata atatttacat taatattagt agttaggttt gaacttttgg tgacttctat    4380
actacggtaa cacattcata tatgcatatg ctttgggtcc ttcatactac ttttatattt    4440
gtaaatcagt gttttggagc aattccaagt ttaagggaaa tatttttgta aatgtgatgg    4500
ttttgaaaat ctgagcaatt cttttgctta caagtttttt taaagcattt gtgctttaaa    4560
attgtgctag tgtttggaat atgataccct ataacccaga taagaaacat aagaatggag    4620
taaacgctgt cgcttgtcgt gctatgccca gcttggcgtg ctggatcagc agtgggactc    4680
cggagtccct agggtcacac cagctcacct gcagcttgtt gcctttctgt gccgtccgcc    4740
cgcccttcag agcactccag aaagttctga catggctctg tatctgctct gtactgtgga    4800 tgccttttg tgtgttgtatc ccaaactgca tagattattt aggataatga taagtttaaa    4860
aaattaatgt tgaagaaaga ttttattaag aatttaaatg ttttttcatt atattgttaa    4920
acttgaacat ttatctgtgg cttatgtgat ttggttaata tgtataaaaa ttgtaagagg    4980
tttatatttc atcttaattc ttttgatgtt gtaaacgtgc ttttcaattc attatttgaa    5040
tgtttatggc acctgacttg taaaagaat tacaaaaaaa aaaatcctta gaatcatta     5099

<210> SEQ ID NO 772
<211> LENGTH: 19
<212> TYPE: DNA
<213> ORGANISM: Artificial Sequence
<220> FEATURE:
<223> OTHER INFORMATION: a synthetic oligonucleotide sequence

<400> SEQUENCE: 772
acccagtatt atgacgagg                                                  19

<210> SEQ ID NO 773
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 773
gcaggagcuu guggaaauau u                                               21

<210> SEQ ID NO 774
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 774
gcugcauucu ggcagaaauu u                                               21

<210> SEQ ID NO 775
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 775
```
gugcucugcu uaugauaauu u                                           21

<210> SEQ ID NO 776
<211> LENGTH: 21
<212> TYPE: RNA
<213> ORGANISM: Artificial Sequence
<220> FEATURE:
<223> OTHER INFORMATION: a synthetic siRNA sequence

<400> SEQUENCE: 776
ccucgucaua auacugggu u                                            21

<210> SEQ ID NO 777
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 777
gcaggagctt gtggaaatat t                                           21

<210> SEQ ID NO 778
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 778
aatatttcca caagctcctg c                                           21

<210> SEQ ID NO 779
<211> LENGTH: 51
<212> TYPE: DNA
<213> ORGANISM: Artificial Sequence
<220> FEATURE:
<223> OTHER INFORMATION: a synthetic oligonucleotide sequence

<400> SEQUENCE: 779
gcaggagctt gtggaaatat tttcaagaga aatatttcca caagctcctg c          51

<210> SEQ ID NO 780
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 780
gctgcattct ggcagaaatt t                                           21

<210> SEQ ID NO 781
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 781
aaatttctgc cagaatgcag c                                           21

<210> SEQ ID NO 782
<211> LENGTH: 51
<212> TYPE: DNA
<213> ORGANISM: Artificial Sequence

```
<220> FEATURE:
<223> OTHER INFORMATION: a synthetic oligonucleotide sequence

<400> SEQUENCE: 782
gctgcattct ggcagaaatt tttcaagaga aaatttctgc cagaatgcag c        51

<210> SEQ ID NO 783
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 783
gtgctctgct tatgataatt t                                         21

<210> SEQ ID NO 784
<211> LENGTH: 21
<212> TYPE: DNA
<213> ORGANISM: Artificial Sequence
<220> FEATURE:
<223> OTHER INFORMATION: a synthetic oligonucleotide sequence

<400> SEQUENCE: 784
aaattatcat aagcagagca c                                         21

<210> SEQ ID NO 785
<211> LENGTH: 51
<212> TYPE: DNA
<213> ORGANISM: Artificial Sequence
<220> FEATURE:
<223> OTHER INFORMATION: a synthetic oligonucleotide sequence

<400> SEQUENCE: 785
gtgctctgct tatgataatt tttcaagaga aaattatcat aagcagagca c        51

<210> SEQ ID NO 786
<211> LENGTH: 10
<212> TYPE: DNA
<213> ORGANISM: Artificial Sequence
<220> FEATURE:
<223> OTHER INFORMATION: a synthetic oligonucleotide sequence

<400> SEQUENCE: 786
cttcctgtca                                                      10
```

US 8,951,979 B2

PAIN TREATMENT USING ERK2 INHIBITORS

CROSS-REFERENCE TO RELATED APPLICATIONS

This application is a nationalization under 35 U.S.C. §371 of PCT/US2009/003523, filed Jun. 12, 2009, Published as WO 2009/151620 and published on Dec. 17, 2009, which claims benefit of the filing date of U.S. Provisional Ser. No. 61/061,254, filed Jun. 13, 2008, the contents of which applications are specifically incorporated herein by reference.

This invention was made with government support from the National Institute on Drug Abuse (NIDA) grant numbers DA001457 and DA000198 (CEO, NIDA training grant DA007274 and NIDA center grant DA005130. The U.S. government has certain rights in this invention.

BACKGROUND OF THE INVENTION

A variety of treatments have been proposed and evaluated for the treatment of pain, including medications, acupuncture, local electrical stimulation, brain stimulation, and surgery. Psychotherapy, relaxation therapy, biofeedback, and behavior modification have also been employed in attempts to treat pain. Despite the many proposed therapies, pain remains an important and increasingly common medical complaint. Moreover, the root causes of pain are sometimes difficult to determine, and frequently are difficult to treat and control.

SUMMARY OF THE INVENTION

This application describes compositions and methods for selectively inhibiting extracellular signal-regulated kinase 2 (ERK2) that are useful for treating pain. Experiments described herein demonstrate that inhibition of ERK2 by use of an ERK2 siRNA delivered by a neurotropic adeno-associated viral vector reduces pain sensitivity in adult mice. Mice were injected in their hind paws with Complete Freund's adjuvant (CFA) to induce peripheral inflammation, mechanical allodynia and thermal hyperalgesia that persisted for at least 96 hours. The ERK2 siRNA protected the animals from developing mechanical allodynia and thermal hyperalgesia throughout the 96 hours after CFA. These findings indicate that ERK2 is involved in the development of pain hypersensitivity and that inhibition of ERK2 expression or activity can reduce or inhibit pain and the development of pain.

One aspect of the invention is a method for treating or inhibiting pain in an animal comprising administering to the animal an inhibitor of extracellular signal-regulated kinase 2 (ERK2) to thereby treat or inhibit pain in the animal. The pain that is treated or inhibited can be chronic pain, acute pain, inflammatory pain, somatic pain, visceral pain, neuropathic pain, and combinations thereof. In some embodiments, the pain that is treated is inflammatory pain. In other embodiments, the pain that is treated is somatic pain or visceral pain. In further embodiments, the origin of pain that is treated is unknown or arises from a combination of causes or pain types. The animal treated can be a human, domesticated animal, experimental animal or a zoo animal. In some embodiments, the inhibitor is administered locally. In other embodiments, the inhibitor is administered systemically (e.g., orally or parenterally). The inhibitor can be any ERK2 inhibitor, for example, the inhibitor can be an antibody, a nucleic acid that inhibits the expression of ERK2, a compound (e.g., a small molecule), as well as other types of ERK2 inhibitors and combinations thereof.

Thus, in some embodiments, the inhibitor is an anti-ERK2 antibody that specifically binds to ERK2. Such an anti-ERK2 antibody can be combined with other ERK2 inhibitors and/or pain medications.

In other embodiments, the inhibitor is a nucleic acid that can inhibit the expression of ERK2. Such a nucleic acid can, for example, hybridize to an mRNA encoding a ERK2 polypeptide with SEQ ID NO: 2. In some embodiments, the nucleic acid can hybridize to an ERK2 polynucleotide comprising SEQ ID NO:2 or SEQ ID NO:771. Examples of inhibitory nucleic acids that can be used in the methods and compositions described herein include antisense nucleic acids, small interfering RNA, ribozyme nucleic acids and combinations thereof. Such inhibitory nucleic acids can have a modified backbone or one or more non-natural internucleoside linkages.

Thus, the nucleic acid can, for example, be a small interfering RNA comprising a DNA or RNA sequence with any of SEQ ID NO:3-162, 166-764, or a combination thereof; or a DNA or RNA that can specifically hybridize to any of SEQ ID NO:3-162, 166-764, or a combination thereof. Such a nucleic acid can be a small interfering RNA comprising a DNA or RNA sequence with any of SEQ ID NO:773-775, or a combination thereof; or a DNA or RNA that can specifically hybridize to any of SEQ ID NO:773-775, or a combination thereof. In some embodiments, the nucleic acid is a small interfering RNA comprising a DNA or RNA sequence corresponding to any one SEQ ID NO:779, 782, 785, or a combination thereof; or a DNA or RNA that can specifically hybridize to any one SEQ ID NO:779, 782, 785, or a combination thereof.

The nucleic acid can be encoded within an expression cassette comprising a promoter and a polynucleotide segment comprising a DNA or RNA corresponding to any of SEQ ID NO: SEQ ID NO:3-162, 166-764, 773-775, 779, 782, 785 or a combination thereof. Such an expression cassette can also comprise a promoter and a polynucleotide segment comprising a DNA or RNA that can hybridize to any of SEQ ID NO: SEQ ID NO:3-162, 166-764, 773-775, 779, 782, 785 or a combination thereof.

Thus, for example, the segment can have the sequence X-L-Y, wherein X is a sense sequence, L is a spacer linked to the 3' end of the sense sequence, and Y is an antisense sequence linked to the 3' end of the linker, and wherein the Y antisense sequence is complementary to the X sequence so that upon expression of the polynucleotide segment, a short hairpin RNA (shRNA) is generated.

The expression cassette can be present in an expression vector where such an expression vector can be a viral vector. Examples of viral vectors that can be used in the methods and compositions of the invention include a neurotropic adeno-associated viral vector such as a neurotropic recombinant adeno-associated virus (rAAV).

The nucleic acids that can inhibit the expression of ERK2 can be combined with other types of ERK2 inhibitors and/or other types of pain medications.

In some embodiments, the inhibitor can be a compound of formula I:

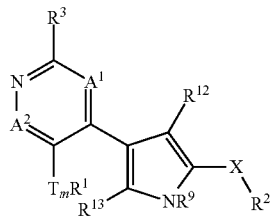

or a pharmaceutically acceptable salt thereof; wherein:
$A^1$ is N or $CR^{10}$;
$A^2$ is N or $CR^{11}$;
T is selected from —C(R$^7$)$_2$—, C(O)—, —C(O)C(O)—, —C(O)NR$^7$—, —C(O)NR$^7$NR$^7$—, —CO$_2$—, —OC(O)—, —NR$^7$CO$_2$—, —O—, —NR$^7$C(O)NR$^7$—, OC(O)NR$^7$—, —NR$^7$NR$^7$—, —NR$^7$C(O)—, —S—, —SO—, —SO$_2$—NR$^7$—, —SO$_2$NR$^7$—, —NR$^7$SO$_2$—, —NR$^7$O$_2$—, or —NR$^7$SO$_2$NR$^7$—;
m is selected from zero or one;
$R^1$ is selected from: (a) hydrogen, CN, halogen, R, N(R$^7$)$_2$, OR, or OH, wherein m is zero; or (b) hydrogen or R, wherein m is one;
X is selected from —C(O)—, —C(O)NR$^7$—, —NR$^7$C(O)—, —NR$^7$SO$_2$—, —SO$_2$NR$^7$—, —S(O)—, or —SO$_2$—;
$R^2$ is selected from —(CH$_2$)$_y$R$^5$, —(CH$_2$)$_y$CH(R$^5$)$_2$, —(CH$_2$)$_y$CH(R$^8$)(R$^5$), —(CH$_2$)$_y$CH(R$^8$)CH(R$^5$)$_2$, —N(R$^4$)$_2$, —NR$^4$(CH$_2$)$_y$N(R$^4$)$_2$, —ON(R$^7$)$_2$, or —NR$^7$OR$^6$;
y is 0-6;
$R^3$ is selected from —R, —OR$^6$, —SR$^6$, —S(O)R$^6$, —SO$_2$R$^6$, —ON(R$^7$)$_2$, —N(R)$_2$, —NRN(R$^7$)$_2$, or —NROR$^6$;
$R^6$ is selected from hydrogen or —R;
each R is independently selected from an optionally substituted group selected from $C_{1-6}$ aliphatic; 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen;
each $R^4$ is independently selected from —R, —R$^7$, —COR$^7$, —CO$_2$R, —CON(R$^7$)$_2$, —SO$_2$R$^7$, —(CH$_2$)$_y$R$^5$, or —(CH$_2$)$_y$CH(R$^5$)$_2$;
each $R^5$ is independently selected from —R, —OR, —CO$_2$R, —(CH$_2$)$_y$N(R$^7$)$_2$, —N(R$^7$)$_2$, —OR$^7$, —SR$^7$, —NR$^7$C(O)R$^7$, —NR$^7$CON(R$^7$)$_2$, —C(O)N(R$^7$)$_2$, —SO$_2$R$^7$, —NR$^7$SO$_2$R$^7$, —C(O)R$^7$, —CN, or —SO$_2$N(R$^7$)$_2$;
each $R^7$ is independently selected from hydrogen or an optionally substituted
$C_{1-6}$ aliphatic group, or two R$^7$ groups bound to the same nitrogen are taken together with the nitrogen to form a 3-7 membered heterocyclic ring having 0-2 heteroatoms in addition to the nitrogen, independently selected from nitrogen, oxygen, or sulfur;
$R^8$ is selected from —R, —(CH$_2$)$_w$OR$^7$, —(CH$_2$)$_w$N(R$^4$)$_2$, or —(CH$_2$)$_w$SR$^7$;
each w is independently selected from 0-4;

$R^9$ is selected from hydrogen, a $C_{1-6}$ aliphatic group, C(O)R$^7$, C(O)OR$^7$, or SO$_2$R$^7$;
$R^{10}$ is selected from R$^7$, halogen, CN, NO$_2$, OR$^7$, SR$^7$, N(R$^7$)$_2$, C(O)R$^7$, or CO$_2$R$^7$; or $R^{10}$ and $R^3$ are taken together to form an optionally substituted 5-7 membered saturated, partially saturated, or aromatic ring having 0-2 heteroatoms independently selected from nitrogen, oxygen, and sulfur;
$R^{11}$ is selected from R$^7$, halogen, CN, NO$_2$, OR$^7$, SR$^7$, N(R$^7$)$_2$, C(O)R$^7$, or CO$_2{}^7$;
$R^{12}$ is selected from R$^7$, CN, NO$_2$, halogen, N(R$^7$)$_2$, SR$^7$, and OR$^7$; and
$R^{13}$ is selected from R$^7$, CN, NO$_2$, halogen, N(R$^7$)$_2$, SR$^7$, and OR$^7$;
provided that only one of $R^{12}$ and $R^{13}$ is a 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen.

In other embodiments, the inhibitor can be one of the following compounds

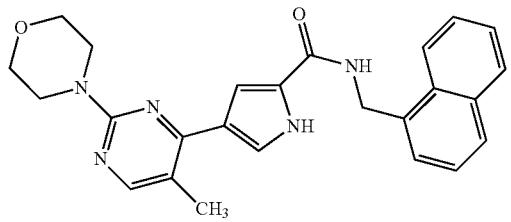

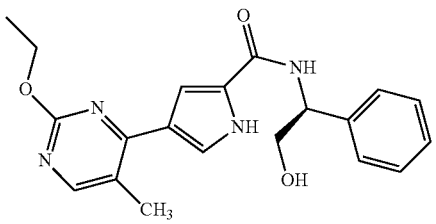

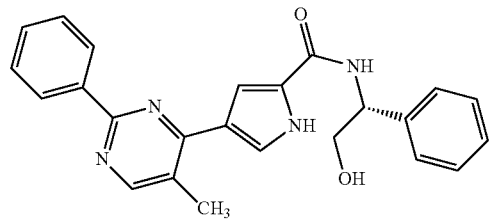

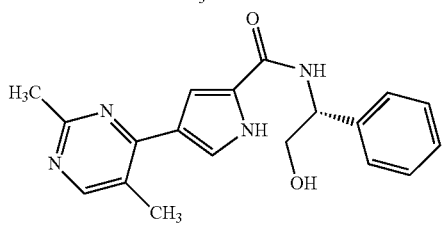

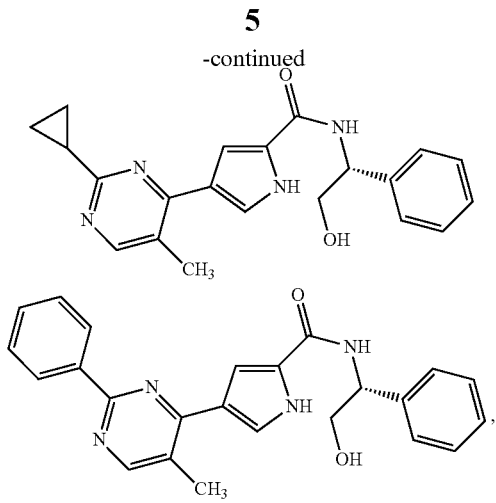

or a combination thereof.

The compounds that inhibit ERK2 can be combined with other ERK2 inhibitors and/or other pain medications.

Another aspect of the invention is an expression cassette comprising a promoter and a polynucleotide segment comprising a DNA or RNA corresponding to any of SEQ ID NO:3-162, 166-764, 773-775, 779, 782, 785, or a combination thereof. The expression cassette can also comprise a promoter and a polynucleotide segment that can hybridize to a DNA or RNA corresponding to any of SEQ ID NO:3-162, 166-764, 773-775, 779, 782, 785, or a combination thereof. The segment in the expression cassette can have the sequence X-L-Y, wherein X is a sense sequence, L is a spacer linked to the 3' end of the sense sequence, and Y is an antisense sequence linked to the 3' end of the linker, and wherein the Y antisense sequence is complementary to the X sequence so that upon expression of the polynucleotide segment, a short hairpin RNA (shRNA) is generated. The sense sequence can be any of the DNA or RNA sense sequences corresponding to SEQ ID NO:3-162, 166-764, 773-775, 779, 782, 785 or a combination thereof. Such an expression cassette can be present in an expression vector. In some embodiments, the expression vector is a viral vector. For example, the viral vector can be a neurotropic adeno-associated viral vector, such as a neurotropic recombinant adeno-associated virus (rAAV).

Another aspect of the invention is a composition comprising a carrier and any of the expression cassettes described herein or any of the expression vectors described herein.

Another aspect of the invention is the use of an ERK2 inhibitor in the preparation of a medicament for the treatment, inhibition and/or prevention of pain.

DESCRIPTION OF THE FIGURES

FIGS. 1A-J illustrate expression of green fluorescent protein (GFP) and the knockdown of ERK2 mRNA in the mouse spinal cord dorsal horn (SCDH) at 3 weeks after the intraparenchymal injection of a neurotropic recombinant adeno-associated virus (rAAV) vector expressing ERK2 siRNA. The expression of GFP was observed in the ipsilateral SCDH following administration of a rAAV vector that expressed a control scrambled ERK2-7 control siRNA (MM, FIG. 1A) or an active ERK2 siRNA, 2-5 (FIG. 1B, sense strand SEQ ID NO:765), 2-7 (FIG. 1C, sense strand SEQ ID NO:769) or 2-8 (FIG. 1D, sense strand, SEQ ID NO:770). Thus, the expression of GFP was not influenced by co-expression of the ERK2 siRNAs. In situ hybridization revealed no change in ERK2 mRNA level in the ipsilateral SCDH compared to the contralateral side in animals treated with vector MM (FIG. 1E). In contrast, each of the three active siRNA vectors induces a significant decrease in ERK2 mRNA in the ipsilateral SCDH (FIG. 1F-1H). Scale bar, 500 µm. In FIG. 1I, ERK2 mRNA expression was quantified from in situ images and plotted in the bar graph as the ratio of the integrated optical density of in situ labeling in the ipsilateral SCDH to that in the contralateral SCDH. Data are the mean±SEM (n=3). Compared to the control vector MM, siRNA vectors 2-5, 2-7 and 2-8 induced a significant decrease (*$p<0.05$) in the ERK2 mRNA expression in the ipsilateral SCDH. There was no significant difference in the ratio among the three active siRNA vectors. FIG. 1J shows that a psiCHECK luciferase assay confirms that shRNA sequences expressed by a rAAV vector are processed to siRNAs that are active against a fusion mRNA of the ERK2 and the humanized *Renilla luciferase* (hRluc) gene. HEK 293 cells were cotransfected with the psiCHECK plasmid (which contains the ERK2-*Renilla luciferase* fusion gene and the firefly luciferase gene) and with a rAAV plasmid expressing a candidate ERK2 shRNA sequence. rAAV plasmids that yield active siRNAs reduce the expression of *Renilla luciferase* relative to firefly luciferase, leading to a reduction of the activity ratio. The assay results are the mean±SEM (n=4). The *Renilla*/firefly signal was normalized to a value of 100% from the results of a concurrent assay containing psiCHECK and a rAAV plasmid that lacked coding for a shRNA sequence (GFP). Significant reductions (*$p<0.05$) in the ratio were observed for each of the three rAAVs plasmids encoding siRNAs (2-5, 2-7 and 2-8). A rAAV plasmid that contained a mismatch (MM) sequence of the active siRNA 2-7 was ineffective in this assay.

FIGS. 2A-G illustrates inhibition of ERK2 expression and phosphorylation in the ipsilateral spinal cord dorsal horn (SCDH) of mice treated with vector 2-7, that expresses an active ERK2 siRNA with sense strand SEQ ID NO:769. An example of a blot is shown in FIG. 2A, the relative protein levels of ERK2 are shown in FIG. 2B, and the relative protein levels of ERK1 are shown in FIG. 2C. FIG. 2A shows Western blot analysis that is graphically summarized in FIG. 2B. As shown in FIG. 2A-B, reduction of ERK2 expression (*$p<0.05$ vs. the control vector MM group) occurs only on the ipsilateral side of the SCDH after vector 2-7 treatment. FIGS. 2A and 2C also show that ERK1 expression was unaffected by vector 2-7. Western blot analysis (FIG. 2D), graphed in FIG. 2E, showed a decrease (*$p<0.05$ vs. the control vector MM group) in phospho-ERK2 (pERK2) and an increase (*$p<0.05$ vs. the control vector MM group) in pERK1 (FIGS. 2D and F) in the ipsilateral SCDH after vector 2-7 treatment. The blot is shown in FIG. 2D, and the relative levels of pERK2 and pERK1 are shown in FIG. 2E and 2F, respectively. FIG. 2G1-G9 show immunolabeling of sections from the spinal cord dorsal horn of mice that did not receive vector (Untreated, FIG. G1-G3)) compared with sections obtained three weeks following administration of vector MM (FIG. G4-G6) or vector 2-7 (FIG. G7-G9). Sections labeled with NeuN (FIG. G1, G4, G7), GFAP (FIG. G2, G5, G8) and OX42 (FIG. G3, G6, G9) show no evidence of neuronal loss or glial activation after vector administration.

FIGS. 3A-G illustrate the cellular localization of pERK1/2 immunolabeling in the ipsilateral spinal cord dorsal horn (SCDH) at 3 weeks after rAAV vector administration. FIG. 3A shows that phosphorylated ERK1/2 (pERK1/2) was detected by immunolabeling in the ipsilateral SCDH after administration of the control vector, MM (red). FIG. 3B shows that NeuN labeling revealed typically distributed neuronal morphologies (green) of the same section. FIG. 3C shows the merged image, illustrating that pERK1/2 was strongly colocalized with NeuN (yellow; arrows). FIG. 3D shows that pERK1/2 immunolabeling was significantly reduced by administration of siRNA vector 2-7 (that expresses an active ERK2 siRNA with sense strand SEQ ID NO:769) compared to control vector MM (FIG. 3A). FIG. 3E shows that the NeuN labeling pattern in siRNA vector 2-7 treated SCDH is similar to that seen with vector MM (FIG. 3B). FIG. 3F shows the merged image illustrating almost no colocalization of pERK1/2 and NeuN labeling after vector 2-7 administration compared to SCDH treated with the control vector MM (FIG. 3C). Scale bar, 100 μm. FIG. 3G1-9 illustrate the cellular localization of GFP immunolabeling in the ipsilateral SCDH 3 weeks after control MM vector administration. FIG. 3H1-9 illustrate the cellular localization of GFP immunolabeling in the ipsilateral SCDH three weeks after administration of vector 2-7, which expresses an active ERK2 siRNA. GFP immunolabeling was colocalized with NeuN (arrows) but not with GFAP or OX42. Scale bar, 100 μM.

FIGS. 4A and B shows Western blot analysis illustrating significant reduction in ERK2 in the ipsilateral SCDH after vector 2-7 administration compared to administration of the control MM vector in the absence of intraplantar treatment (NT) (*$p<0.05$, vs. vector MM/NT). This reduction in ERK2 persists from 1 to 96 hours after CFA administration (*$p<0.05$, vs. vector MM). Note also that at 96 hr after CFA, ERK2 is increased in the ipsilateral SCDH of the vector MM group NT compared to control (MM) ERK2 levels 1 hr after CFA (#$p<0.05$). FIGS. 4A and C show that ERK1 expression is also increased at 96 hr after CFA administration (#$p<0.05$) and this increase is prevented by vector 2-7 treatment. FIGS. 4D and 4E show that pERK2 is reduced after siRNA vector 2-7 administration and that this reduction persists from 1 hour to 96 hours after CFA (*$p<0.05$, vs. vector MM). In animals receiving the control vector (MM), pERK2 was increased at 1 and 96 hr after CFA administration, compared to the no treatment control (#$p<0.05$). FIG. 4C shows that ERK1 was increased at 96 hours after administration of CFA (*$p<0.05$, vs. vector MM/NT). This increase in ERK1 was not observed after CFA in animals administered the ERK2 siRNA vector 2-7. FIG. 4F shows that pERK1 was increased at 1 and 96 hr in the control (vector MM group; #$p<0.05$ vs. vector MM/NT), but that pERK1 levels remained relatively unchanged after administration of CFA and the ERK2 siRNA vector 2-7.

FIG. 5A is an example of the Western blot of ERK1 and 2 as well as pERK1 and 2 proteins. FIG. 5B-5E are bar graphs quantifying the amounts of these proteins and revealing that no change in ERK2 expression (FIG. 5B), ERK1 expression (FIG. 5C), pERK2 (FIG. 5D) or pERK1 (FIG. 5E) occurs upon administration of the control MM vector, which encodes a scrambled siRNA sequence. FIG. 5F illustrates the time course of the increase in pERK2 in the ipsilateral SCDH following intraplantar CFA administration. Tissue was collected from groups (n=3) of control mice (no intraparenchymal injection (IPI) of vector) before and at 1, 24 and 96 hrs after intraplantar CFA. The proteins from these tissues were subjected to Western blot analysis and probed for pERK and actin. FIG. 5F shows the ratios of pERK2/actin normalized to the before CFA administration control. The expression of pERK 2 protein was increased at 1 hr and that increase is sustained through 24 and 96 hrs post CFA. (*$p<0.05$ vs. the before treatment group).

FIGS. 6A-H show that ERK2 siRNA vector 2-7 prevents the increased phosphorylation of ERK1/2 that is induced in the ipsilateral spinal cord dorsal horn (SCDH) by intraplantar administration of Complete Freund's adjuvant (CFA). FIG. 6A shows the basal level expression of pERK1/2 can be seen mainly in lamina I-II neurons in the control mice after administration of control vector MM and in the absence of intraplantar CFA treatment (NT). FIGS. 6B-6C illustrates that pERK1/2 immunolabeling was increased at 1 hour (FIG. 6B) and 96 hours (FIG. 6C) following CFA administration. FIGS. 6D-6F show that pERK1/2 immunolabeling in the SCDH of mice treated with vector 2-7 is reduced compared to the MM control vector, before treatment (NT) and after CFA administration. FIGS. 6G and H show that quantification of pERK1/2 as labeled neuron density (FIG. 6G) or percentage of field (FIG. 6H) in laminas I-II revealed a significant increase in pERK1/2 at 1 hour and 96 hours after CFA administration the MM control mice (#$p<0.05$ vs. vector MM/NT). Vector 2-7 reduced pERK1/2 immunolabeling at each corresponding time point compared to vector MM (FIGS. 6G and 6H, *$p<0.05$, vs. vector MM). CFA induced an increase in pERK1/2 labeling as measured by neuron density or percentage of field at 1 hour and 96 hours in the control vector MM group (FIGS. 6G and 6H, #$p<0.05$). For the vector 2-7 group, CFA produced increases in labeling although less than the corresponding increases in the vector MM group. Scale bar, 500 μm.

FIG. 8A shows that CFA administration resulted in equivalent inflammation as measured by paw size at 24, 48 and 96 hr (*$p<0.05$, vs. baseline, n=10 per treatment group). The control vector MM group showed thermal hyperalgesia as measured as a reduction in the paw withdrawal threshold using a thermal stimulus (FIG. 8B) and mechanical allodynia as measured as a reduction in the mechanical threshold (50% g threshold) using von Frey hairs (FIG. 8C) applied to the paw at 24, 48 and 96 hr after intraplantar CFA compared to the baseline (*$p<0.05$, vs. baseline). The mice that received vector 2-7 were protected from CFA-induced thermal hyperalgesia (FIG. 8B) and mechanical allodynia (FIG. 8C) (n=10 per treatment group). Error bars indicate SEM.

FIG. 9 illustrates immunolabeling of c-fos in the ipsilateral SCDH following intraplantar CFA administration. FIG. 9A shows that in the vector control animals, c-fos immunolabeling is absent from the SCDH when no CFA is administered. FIGS. 9B and 9C show that CFA induced c-fos expression in the ipsilateral SCDH at 1 hour (FIG. 9B) but not at 96 hour (FIG. 9C) after CFA administration. FIG. 9D-F show that CFA induced less c-fos expression at 1 hour (FIG. 9E) in animals that received the ERK2 siRNA vector 2-7. FIG. 9F shows the c-fos expression observed at 96 hours after CFA injection in animals that received the ERK2 siRNA vector 2-7. FIG. 9D shows the basal level of c-fos expression in animals that received the ERK2 siRNA vector 2-7 when no CFA is administered. FIG. 9G graphically illustrates quantification of c-fos labeled neurons in lamina I-II, revealing a significant increase at 1 hour after CFA administration (*$p<0.05$ vs. no treatment (NT)). However, administration of the ERK2 siRNA vector 2-7 reduced the degree to which c-fos expression increased.

FIG. 10A-H illustrate that dynorphin A immunolabeling in the ipsilateral SCDH was not changed by intraplantar CFA administration after 1 hour or even 96 hours. FIGS. 10A-C show Dynorphin A immunolabeling in the absence of CFA (FIG. 10A), at 1 hr (FIG. 10B) or 96 hr (FIG. 10C) after CFA administration in the MM vector control animals. FIGS. 10D-F show Dynorphin A immunolabeling in the absence of CFA (FIG. 10D), at 1 hr (FIG. 10E) or 96 hr (FIG. 10F) after CFA administration of the ERK2 siRNA vector 2-7 to animals. Quantification of dynorphin A labeled neurons (FIG. 10G) or percentage of field labeled with dynorphin A (FIG. 10H) revealed no significant changes following CFA in either group of animals at 1 hr or 96 hr.

FIG. 11A is an image of a Western blot showing that each of the human ERK2 siRNAs #1 (SEQ ID NO:773), #2 (SEQ ID NO:774) and #3 (SEQ ID NO:775) significantly reduced human ERK2 expression without significantly changing ERK1 expression. FIG. 11B graphically illustrates the reduction of human ERK2 expression by each of the human ERK2 siRNAs. As shown, each of human ERK2 siRNAs #1 (SEQ ID NO:773), #2 (SEQ ID NO:774) and #3 (SEQ ID NO:775) reduced human ERK2 expression by about 70-80%.

FIG. 12A is a schematic diagram of the structure of an shRNA cassette, with the non-template strand shown. The sequence is shown in the 5' to 3' direction, where xx represent additional residues (1-5 residues) that are used for cloning (i.e., adaptor sequences to join the cassette to the vector, which are typically partial sequence of a restriction endonuclease site). FIG. 12B shows a structure of a vector that can express the shRNA cassette shown in FIG. 12A.

DETAILED DESCRIPTION OF THE INVENTION

Figure 1I:
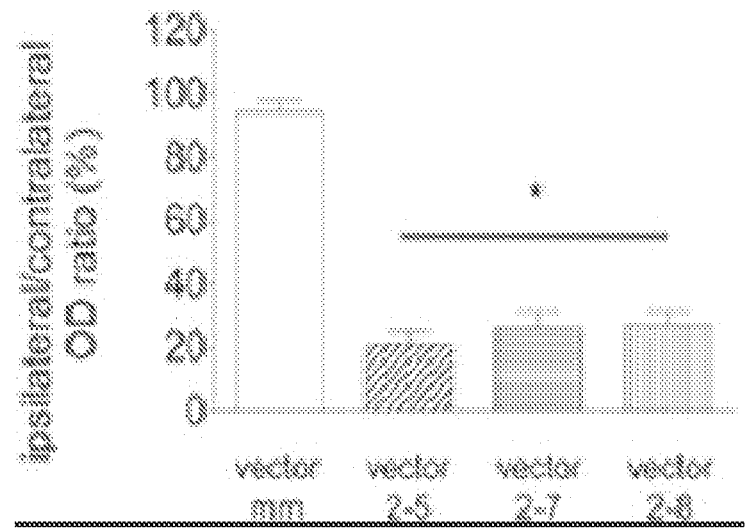

This application describes agents, compositions and methods for reducing and/or inhibiting pain that involve use of ERK2 inhibitors.

Pain

The compositions and methods herein are useful for treating and/or reducing pain. All types of pain can be treated with the compositions and methods, including chronic pain, acute pain (e.g., nociceptive pain), inflammatory pain, somatic pain, visceral pain, neuropathic pain, and combinations thereof.

There are primarily three types of pain: somatic, visceral and neuropathic, all of which can be acute and chronic.

Somatic pain is typically caused by the activation of pain receptors in either the cutaneous or musculoskeletal tissues. In contrast to surface somatic pain which is usually described as sharp and may have a burning or pricking quality, deep somatic pain is usually characterized as a dull, aching but localized sensation. Somatic pain may include fractures in the vertebrae, joint pain (deep somatic pain) and postsurgical pain from a surgical incision (surface pain). Thus, the pain to be treated can be a form of somatic pain.

Visceral pain is caused by activation of pain receptors in internal areas of the body that are enclosed within a cavity. Visceral pain is usually described as pressure-like, poorly localized and deep. Therefore, the pain to be treated can be a form of visceral pain.

Neuropathic pain, caused by neural damage, is usually described as burning, tingling, shooting or stinging but can also manifest itself as sensory loss either as a result of compression, infiltration, chemical or metabolic damage or is idiopathic. Examples of neuropathic pain are heterogenous and include medication-induced neuropathy and nerve compression syndromes such as carpal tunnel, radiculopathy due to vertebral disk herniation, post-amputation syndromes such as stump pain and phantom limb pain, metabolic disease such as diabetic neuropathy, neurotropic viral disease from herpes zoster and human immunodeficiency virus (HIV) disease, tumor infiltration leading to irritation or compression of nervous tissue, radiation neuritis, as after cancer radiotherapy, and autonomic dysfunction from complex regional pain syndrome (CRPS). Thus, the pain to be treated can be a form of neuropathic pain.

Inflammatory pain is related to tissue damage which can occur in the form of penetration wounds, burns, extreme cold, fractures, inflammatory arthropathies as seen in many autoimmune conditions, excessive stretching, infections, vasoconstriction and cancer. The pain to be treated can therefore be a form of inflammatory pain.

The chronic pain can be due to problems such as arthritis, cancer, injuries, HIV, and the like. According to the invention, the compositions and methods can treat chronic pain.

Acute pain, termed nociception, is the instantaneous onset of a painful sensation in response to a noxious stimulus. It is considered to be adaptive because it can prevent an organism from damaging itself. For example, removing a hand from a hot stove as soon as pain is felt can prevent serious burns. The second type of pain is persistent pain. Unlike acute pain, it usually has a delayed onset but can last for hours to days. It is predominately considered adaptive because the occurrence of persistent pain following injury can prevent further damage to the tissue. For example, the pain associated with a sprained ankle will prevent the patient from using the foot, thereby preventing further trauma and aiding healing. A third category of pain is chronic pain. It has a delayed onset and can last for months to years. In contrast to acute and persistent pain, chronic pain is considered maladaptive and is associated with conditions such as arthritis, nerve injury, AIDS and diabetes. Yet another type of pain can be termed breakthrough pain. This is a brief flare-up of severe pain lasting from minutes to hours that can occur in the presence or absence of a preceding or precipitating factor even while the patient is regularly taking pain medication. Many patients experience a number of episodes of breakthrough pain each day. The pain to be treated with the compositions and methods described herein can be acute pain.

According to the invention, pain can be treated or inhibited in an animal. As used herein an animal is a mammal or a bird. Thus, animals that can be treated using the compositions and/or methods of the invention include humans, domesticated animals, experimental animals and zoo animals. For example, animals that can be treated using the compositions and/or methods of the invention include humans, dogs, cats, horses, pigs, cattle, goats, mice, rats, rabbits, and the like.

ERK2

Extracellular signal-regulated kinases ERK1 and ERK2 (Boulton et al., 1991) are also referred to as p44 and p42 mitogen-activated protein kinase (MAPK). ERK1 and ERK2 belong to a group of evolutionarily conserved serine/threonine protein kinases that play critical roles in cell proliferation, differentiation and survival. They are activated by dual phosphorylation on their regulatory tyrosine and threonine residues by an upstream kinase, MEK. In the central nervous system, ERK1 and ERK2 have been linked to signal transduction cascades that regulate neuronal activity and plasticity.

The high structural resemblance between ERK1 and ERK2 has limited studies of their individual contributions to physiological processes. ERK1 and ERK2 also have similar sensitivities to activation by MEK (Zheng and Guan, 1993) and are often functionally redundant in vitro (Robbins et al., 1993). However, studies in knockout mice indicate that ERK1 and ERK2 can play different roles in vivo. For example, ERK1 knockout mice are viable, fertile and of normal size (Pages et al., 1999), but ERK2 knockout mice die before embryonic day 8.5 due to defects in trophoblast and placental development and in mesoderm differentiation (Hatano et al., 2003; Saba-El-Leil et al., 2003; Yao et al., 2003). These studies suggest that ERK1 is dispensable as long as ERK2 can compensate for its loss. However, the converse is not true—ERK2 is an essential protein. Other studies indicate that ERK1 and ERK2 respond differently to growth factors and may regulate cell proliferation differently (Li and Johnson, 2006)(Fremin et al., 2007)(Zeng et al., 2005). Furthermore, ERK2 (but not ERK1) is involved in the modulation of hippocampal long term potentiation (English and Sweatt, 1996).

As shown in the Examples of this application, small interfering RNAs (siRNA) that hybridize to ERK2 mRNA selectively knock down the expression of ERK2 in spinal cord dorsal horn neurons. The siRNA was delivered by a neurotropic recombinant adeno-associated virus (rAAV), which limited the knockdown of ERK2 to neurons, and permitted examination of the specific role of the neuronal spinal cord dorsal horn ERK2 in the development of injury-induced pain hypersensitivity in vivo. Such reduction of ERK2 expression protected animals from developing mechanical allodynia (a painful response to what usually would be a non-painful stimulus) and thermal hyperalgesia (increased sensation to painful stimuli that accompany thermal injury) throughout the 96 hr after CFA.

Sequences for ERK2 proteins are readily available, for example, from the website provided by the National Center for Biotechnology Information (NCBI) at www.ncbi.nlm.nih.gov. One example of a human ERK2 sequence is provided below as SEQ ID NO:1 (NCBI accession number NP_002736 (gi:66932916)).

```
  1 MAAAAAAGAG PEMVRGQVFD VGPRYTNLSY IGEGAYGMVC
 41 SAYDNVNKVR VAIKKISPFE HQTYCQRTLR EIKILLRFRH
 81 ENIIGINDII RAPTIEQMKD VYIVQDLMET DLYKLLKTQH
121 LSNDHICYFL YQILRGLKYI HSANVLHRDL KPSNLLLNTT
161 CDLKICDFGL ARVADPDHDH TGFLTEYVAT RWYRAPEIML
201 NSKGYTKSID IWSVGCILAE MLSNRPIFPG KHYLDQLNHI
241 LGILGSPSQE DLNCIINLKA RNYLLSLPHK NKVPWNRLFP
281 NADSKALDLL DKMLTFNPHK RIEVEQALAH PYLEQYYDPS
321 DEPIAEAPFK FDMELDDLPK EKLKELIFEE TARFQPGYRS
```

One example of a nucleotide sequence for the SEQ ID NO:1 ERK2 protein is provided below as SEQ ID NO:2 (NCBI accession number NM_138957, gi:75709179).

```
   1 GCCCCTCCCT CCGCCCGCCC GCCGGCCCGC CCGTCAGTCT
  41 GGCAGGCAGG CAGGCAATCG GTCCGAGTGG CTGTCGGCTC
  81 TTCAGCTCTC CCGCTCGGCG TCTTCCTTCC TCCTCCCGGT
 121 CAGCGTCGGC GGCTGCACCG GCGGCGGCGC AGTCCCTGCG
 161 GGAGGGGCGA CAAGAGCTGA GCGGCGGCCG CCGAGCGTCG
 201 AGCTCAGCGC GGCGGAGGCG GCGGCGGCCC GGCAGCCAAC
 241 ATGGCGGCGG CGGCGGCGGC GGGCGCGGGC CCGGAGATGG
 281 TCCGCGGGCA GGTGTTCGAC GTGGGGCCGC GCTACACCAA
 321 CCTCTCGTAC ATCGGCGAGG GCGCCTACGG CATGGTGTGC
 361 TCTGCTTATG ATAATGTCAA CAAAGTTCGA GTAGCTATCA
 401 AGAAAATCAG CCCCTTTGAG CACCAGACCT ACTGCCAGAG
 441 AACCCTGAGG GAGATAAAAA TCTTACTGCG CTTCAGACAT
 481 GAGAACATCA TTGGAATCAA TGACATTATT CGAGCACCAA
 521 CCATCGAGCA AATGAAAGAT GTATATATAG TACAGGACCT
 561 CATGGAAACA GATCTTTACA AGCTCTTGAA GACACAACAC
 601 CTCAGCAATG ACCATATCTG CTATTTTCTC TACCAGATCC
 641 TCAGAGGGTT AAAATATATC CATTCAGCTA ACGTTCTGCA
 681 CCGTGACCTC AAGCCTTCCA ACCTGCTGCT CAACACCACC
 721 TGTGATCTCA AGATCTGTGA CTTTGGCCTG GCCCGTGTTG
 761 CAGATCCAGA CCATGATCAC ACAGGGTTCC TGACAGAATA
 801 TGTGGCCACA CGTTGGTACA GGGCTCCAGA AATTATGTTG
 841 AATTCCAAGG GCTACACCAA GTCCATTGAT ATTTGGTCTG
 881 TAGGCTGCAT TCTGGCAGAA ATGCTTTCTA ACAGGCCCAT
 921 CTTTCCAGGG AAGCATTATC TTGACCAGCT GAACCACATT
 961 TTGGGTATTC TTGGATCCCC ATCACAAGAA GACCTGAATT
1001 GTATAATAAA TTTAAAAGCT AGGAACTATT TGCTTTCTCT
1041 TCCACACAAA AATAAGGTGC CATGGAACAG GCTGTTCCCA
1081 AATGCTGACT CCAAAGCTCT GGACTTATTG GACAAAATGT
1121 TGACATTCAA CCCACACAAG AGGATTGAAG TAGAACAGGC
1161 TCTGGCCCAC CCATATCTGG AGCAGTATTA CGACCCGAGT
1201 GACGAGCCCA TCGCCGAAGC ACCATTCAAG TTCGACATGG
1241 AATTGGATGA CTTGCCTAAG GAAAAGCTCA AGGAACTAAT
1281 TTTTGAAGAG ACTGCTAGAT TCCAGCCAGG ATACAGATCT
1321 TAAATTTGTC AGGTACCTGG AGTTTAATAC AGTGAGCTCT
1361 AGCAAGGGAG GCGCTGCCTT TTGTTTCTAG AATATTATGT
1401 TCCTCAAGGT CCATTATTTT GTATTCTTTT CCAAGCTCCT
1441 TATTGGAAGG TATTTTTTTA AATTTAGAAT TAAAAATTAT
1481 TTAGAAAGTT ACATATAAA
```

Inhibitors of ERK2

According to the invention, any ERK2 inhibitor can be used to treat or reduce pain in an animal (e.g., in a human). Such ERK2 inhibitors can be nucleic acids that inhibit the expression of ERK2 protein, small molecule ERK2 inhibitors, anti-ERK2 antibodies and combinations thereof. These types of ERK2 inhibitors are described in more detail below.

The ERK2 inhibitor(s) employed in the compositions and methods described herein can partially or completely inhibit ERK2. Thus, the ERK2 inhibitor(s) can inhibit about 99% ERK2 activity or expression, or about 95% ERK2 activity or expression, or about 90% ERK2 activity or expression, or about 80% ERK2 activity or expression, or about ERK2 60% activity or expression, or about 50% ERK2 activity or expression, or about 35% ERK2 activity or expression, or any level if inhibition greater than about 30% ERK2 inhibition. Moreover, administered locally, the percent ERK2 inhibition may in some embodiments be greater than would be desirable when ERK2 is administered systemically. Thus, for example, when administered locally (e.g., to the site of pain or to the spinal fluid or column), the ERK2 inhibition can be more than 95% ERK2 inhibition, or more than 90% ERK2 inhibition, or more than 85% ERK2 inhibition, or more than 80% ERK2 inhibition, or more than 75% ERK2 inhibition, or more than 70% ERK2 inhibition, or more than 65% ERK2 inhibition, or more than 60% ERK2 inhibition, or more than 50% ERK2 inhibition. However, in other embodiments when ERK2 inhibitors are administered systemically, a lesser percent ERK2 inhibition may be desirable. For example, when administered systemically, the ERK2 inhibition can be less than 60% ERK2 inhibition, or less than 55% ERK2 inhibition, or less than 50% ERK2 inhibition, or less than 40% ERK2 inhibition, or less than 30% ERK2 inhibition.

While the focus of the methods is upon inhibiting ERK2, some inhibition of ERK1 may occur when using some of these ERK2 inhibitors because ERK1 and ERK2 are so closely related. Some inhibition of ERK1 is acceptable. For example, while ERK2 knockout mice die before embryonic day 8.5, mutations that lead to complete loss of ERK1 function do not affect the viability, fertility and or growth of animals. Thus, in some embodiments, ERK1 is inhibited to about the same extent as, or to an even a greater extent than, ERK2 by a selected ERK2 inhibitor or combination of inhibitors. In other embodiments, ERK1 is inhibited less than ERK2 by a selected ERK2 inhibitor or combination of inhibitors. For example, administration of an ERK2 inhibitor can in some embodiments give rise to less than 70% ERK1 inhibition, or less than 60% ERK1 inhibition, or less than 50% ERK1 inhibition, or less than 40% ERK1 inhibition, or less than 30% ERK1 inhibition, or less than 20% ERK1 inhibition, or less than 10% ERK1 inhibition.

Nucleic Acid Inhibitors

In some embodiments, the ERK2 inhibitors used in the compositions and methods described herein are nucleic acids that can inhibit the expression of an ERK2 protein. Nucleic acids that can inhibit the expression of an ERK2 protein include small interfering RNAs (siRNAs), ribozymes, antisense nucleic acids, and the like. For example, small interfering RNAs (siRNA) targeted against ERK2 transcripts were used to specifically reduce ERK2 expression by about 75% to 80% (see Example 2).

In some embodiments, an inhibitory nucleic acid of the invention can hybridize to an ERK2 nucleic acid (e.g., any of SEQ ID NOs: 2 or SEQ ID NO:771) under intracellular conditions. In other embodiments, the inhibitory nucleic acids can hybridize to an ERK2 nucleic acid under stringent hybridization conditions. In general, the term "hybridize" is used to indicate that a nucleic acid specifically hybridizes to a complementary nucleic acid.

The inhibitory nucleic acids of the invention are sufficiently complementary to endogenous ERK2 nucleic acids to inhibit expression of an ERK2 nucleic acid under either intracellular conditions or under string hybridization conditions. In many embodiments it is desirable for ERK2 inhibitory nucleic acids to hybridize to ERK2 mRNA (e.g., the mRNA encoded by SEQ ID NO:2 or SEQ ID NO:771). However, the ERK2 inhibitory nucleic acid need not be 100% complementary to an endogenous ERK2 mRNA. Instead the ERK2 inhibitory nucleic acid can be less than 100% complementary to an endogenous ERK2 mRNA. For example, the ERK2 inhibitory nucleic acid can have one, two, three, four, or five mismatches or nucleotides that are not complementary to an endogenous ERK2 mRNA.

Intracellular conditions refer to conditions such as temperature, pH and salt concentrations typically found inside a cell, e.g. a mammalian cell. One example of such a mammalian cell is a neuron.

Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein.

In some embodiments, an ERK2 inhibitory nucleic acid has a stretch of 10, 11, 12, 13, 14, 15, 16, 17, or 18 contiguous nucleotides that are complementary to an ERK2 DNA or RNA. However, inhibitory nucleic acids that comprise, for example, 2, 3, 4, or 5 or more stretches of contiguous nucleotides that are precisely complementary to an ERK2 coding sequence, each separated by a stretch of contiguous nucleotides that are not complementary to adjacent coding sequences, may also inhibit the function of a ERK2 nucleic acid. In general, each stretch of contiguous, complementary nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to an ERK2 nucleic acid to estimate the degree of mismatching that will be tolerated for inhibiting expression of ERK2. Inhibitory nucleic acids of the invention include, for example, a small interfering RNA, a ribozyme or an antisense nucleic acid molecule.

An antisense nucleic acid molecule may be single or double stranded (e.g. a small interfering RNA (siRNA)), and may function in an enzyme-dependent manner or by steric blocking.

Small interfering RNA (siRNA) molecules are also called short interfering RNA or silencing RNA. These siRNA molecules are double-stranded and are generally about 20-25 nucleotides in length, with a two to three nucleotide overhang on one or both ends. Typically, siRNA interfere with gene expression by binding to mRNA, which leads to degradation of the mRNA by nucleases. Thus, siRNAs interfere with gene expression. By selecting a sequence for the siRNA that is complementary to the mRNA transcribed by a gene of interest, the siRNA can specifically interfere with the expression from that gene. Accordingly, one aspect of the invention is an siRNA that binds to an ERK2 mRNA and interferes with (inhibits) the expression of the ERK2 protein.

siRNAs can be exogenously introduced into cells by various methods. While siRNAs can be introduced by parenteral injection, the siRNA can also be encoded within and expressed by an appropriate expression vector. This can be done by introducing a loop between the two strands of the siRNA, so that a single long transcript is expressed that naturally folds into a short hairpin RNA (shRNA). This shRNA is naturally processed into a functional siRNA within a cell. Further information on delivery of siRNAs, ribozymes, antisense RNA and the like is provided below.

The nucleotide sequence of siRNAs may be designed using a siRNA design computer program. For example, siRNA sequences may be designed using the siRNA design program (http://jura.wi.mit.edu/siRNAext/) from the Whitehead Institute for Biomedical Research (MIT)(see, Yuan et al., Nuc. Acids Res. 32:W130-134 (2004)). Alternatively, siRNA sequences can be designed using a program available from the Ambion website ambion.com/techlib/misc/siRNA_finder.html).

In general, these programs generate siRNA sequences from an input DNA sequence or an input accession number (e.g., an ERK2 nucleic acid such as SEQ ID NO:2 or an NCBI accession number NM_138957) using siRNA generation rules developed as described, for example, Yuan et al., Nuc. Acids Res. 32:W130-134 (2004).

Thus, the inventors have identified the following siRNAs that bind ERK2 and can be used to inhibit, treat or reduce pain, where the targeted ERK2 mRNA sequence is identified as "mRNA," the sense strand of the siRNA is identified as the "S" strand and where the antisense strand of the siRNA is identified as the "AS" strand. Note that thymidine (T) is used in the mRNA sequences shown below—for actual mRNA sequences, each thymidine would be a uridine (U).

```
S 5':       GCAGGAGCUUGUGGAAAUA UU(SEQ ID NO: 3)
mRNA:    GA GCAGGAGCTTGTGGAAATA CC(SEQ ID NO: 4)
AS 3':   UU CGUCCUCGAACACCUUUAU    (SEQ ID NO: 5)

S 5':       GCUGCAUUCUGGCAGAAAU UU(SEQ ID NO: 6)
mRNA:    AG GCTGCATTCTGGCAGAAAT GC(SEQ ID NO: 7)
AS 3':   UU CGACGUAAGACCGUCUUUA    (SEQ ID NO: 8)

S 5':       GUGCUCUGCUUAUGAUAAU UU(SEQ ID NO: 9)
mRNA:    GT GTGCTCTGCTTATGATAAT GT(SEQ ID NO: 10)
AS 3':   UU CACGAGACGAAUACUAUUA    (SEQ ID NO: 11)

S 5':       CGUGCAUGUAUAGUUUAAU UU(SEQ ID NO: 12)
mRNA:    AC CGTGCATGTATAGTTTAAT TG(SEQ ID NO: 13)
AS 3':   UU GCACGUACAUAUCAAAUUA    (SEQ ID NO: 14)

S 5':       GUCCUCAAGUACUCAAAUA UU(SEQ ID NO: 15)
mRNA:    CT GTCCTCAAGTACTCAAATA TT(SEQ ID NO: 16)
AS 3':   UU CAGGAGUUCAUGAGUUUAU    (SEQ ID NO: 17)

S 5':       CCGUGCAUGUAUAGUUUAA UU(SEQ ID NO: 18)
mRNA:    CA CCGTGCATGTATAGTTTAA TT(SEQ ID NO: 19)
AS 3':   UU GGCACGUACAUAUCAAAUU    (SEQ ID NO: 20)

S 5':       GGUGCCUUCUUGGUAUUGU UU(SEQ ID NO: 21)
mRNA:    TT GGTGCCTTCTTGGTATTGT AC(SEQ ID NO: 22)
AS 3':   UU CCACGGAAGAACCAUAACA    (SEQ ID NO: 23)

S 5':       GAGGAACACUGCGUCUUUA UU(SEQ ID NO: 24)
mRNA:    GA GAGGAACACTGCGTCTTTA AA(SEQ ID NO: 25)
AS 3':   UU CUCCUUGUGACGCAGAAAU    (SEQ ID NO: 26)

S 5':       GUGGUCACUUGUACCAUAU UU(SEQ ID NO: 27)
mRNA:    CT GTGGTCACTTGTACCATAT AG(SEQ ID NO: 28)
AS 3':   UU CACCAGUGAACAUGGUAUA    (SEQ ID NO: 29)

S 5':       CCCAAGUUUAAGGGAAAUA UU(SEQ ID NO: 30)
mRNA:    AT CCCAAGTTTAAGGGAAATA TT(SEQ ID NO: 31)
AS 3':   UU GGGUUCAAAUUCCCUUUAU    (SEQ ID NO: 32)

S 5':       CAGCCAUUCAGAGGAAACU UU(SEQ ID NO: 33)
mRNA:    TT CAGCCATTCAGAGGAAACT GT(SEQ ID NO: 34)
AS 3':   UU GUCGGUAAGUCUCCUUUGA    (SEQ ID NO: 35)

S 5':       GUGGGAUGGAAUUGAAAGA UU(SEQ ID NO: 36)
mRNA:    CA GTGGGATGGAATTGAAAGA AC(SEQ ID NO: 37)
AS 3':   UU CACCCUACCUUAACUUUCU    (SEQ ID NO: 38)

S 5':       GGCUCUUCUUACAUUUGUA UU(SEQ ID NO: 39)
mRNA:    TT GGCTCTTCTTACATTTGTA AA(SEQ ID NO: 40)
AS 3':   UU CCGAGAAGAAUGUAAACAU    (SEQ ID NO: 41)

S 5':       CCGGAUAACACUGAUUAGU UU(SEQ ID NO: 42)
mRNA:    TA CCGGATAACACTGATTAGT CA(SEQ ID NO: 43)
AS 3':   UU GGCCUAUUGUGACUAAUCA    (SEQ ID NO: 44)

S 5':       CACCAACCAUCGAGCAAAU UU(SEQ ID NO: 45)
mRNA:    AG CACCAACCATCGAGCAAAT GA(SEQ ID NO: 46)
AS 3':   UU GUGGUUGGUAGCUCGUUUA    (SEQ ID NO: 47)

S 5':       GGUAGUCACUAACAUAUAU UU(SEQ ID NO: 48)
mRNA:    AT GGTAGTCACTAACATATAT AA(SEQ ID NO: 49)
AS 3':   UU CCAUCAGUGAUUGUAUAUA    (SEQ ID NO: 50)

S 5':       GUGCCUUCUUGGUAUUGUA UU(SEQ ID NO: 51)
mRNA:    TG GTGCCTTCTTGGTATTGTA CC(SEQ ID NO: 52)
AS 3':   UU CACGGAAGAACCAUAACAU    (SEQ ID NO: 53)

S 5':       CAGGGUUCCUGACAGAAUA UU(SEQ ID NO: 54)
mRNA:    CA CAGGGTTCCTGACAGAATA TG(SEQ ID NO: 55)
AS 3':   UU GUCCCAAGGACUGUCUUAU    (SEQ ID NO: 56)

S 5':       CCACCUGUGAUCUCAAGAU UU(SEQ ID NO: 57)
mRNA:    CA CCACCTGTGATCTCAAGAT CT(SEQ ID NO: 58)
AS 3':   UU GGUGGACACUAGAGUUCUA    (SEQ ID NO: 59)

S 5':       CCCUUGAGCUACUUCAAAU UU(SEQ ID NO: 60)
mRNA:    CG CCCTTGAGCTACTTCAAAT GT(SEQ ID NO: 61)
AS 3':   UU GGGAACUCGAUGAAGUUUA    (SEQ ID NO: 62)

S 5':       GUGCAGAUGAGAAGCUAUA UU(SEQ ID NO: 63)
mRNA:    TG GTGCAGATGAGAAGCTATA AC(SEQ ID NO: 64)
AS 3':   UU CACGUCUACUCUUCGAUAU    (SEQ ID NO: 65)

S 5':       GCUCUGCUUAUGAUAAUGU UU(SEQ ID NO: 66)
mRNA:    GT GCTCTGCTTATGATAATGT CA(SEQ ID NO: 67)
AS 3':   UU CGAGACGAAUACUAUUACA    (SEQ ID NO: 68)

S 5':       GUCAGAAACAAAUGGAAAU UU(SEQ ID NO: 69)
mRNA:    GG GTCAGAAACAAATGGAAAT CC(SEQ ID NO: 70)
AS 3':   UU CAGUCUUUGUUUACCUUUA    (SEQ ID NO: 71)

S 5':       GCCUACGAUUGAAAUGAAA UU(SEQ ID NO: 72)
mRNA:    AT GCCTACGATTGAAATGAAA AC(SEQ ID NO: 73)
AS 3':   UU CGGAUGCUAACUUUACUUU    (SEQ ID NO: 74)

S 5':       CCCUGGUUCUCUCUAAAGA UU(SEQ ID NO: 75)
mRNA:    TT CCCTGGTTCTCTCTAAAGA GG(SEQ ID NO: 76)
AS 3':   UU GGGACCAAGAGAGAUUUCU    (SEQ ID NO: 77)

S 5':       GGGUAGAAGAAUACUGUAU UU(SEQ ID NO: 78)
mRNA:    CT GGGTAGAAGAATACTGTAT TG(SEQ ID NO: 79)
AS 3':   UU CCCAUCUUCUUAUGACAUA    (SEQ ID NO: 80)

S 5':       CCAAGUUUAAGGGAAAUAU UU(SEQ ID NO: 81)
mRNA:    TC CCAAGTTTAAGGGAAATAT TT(SEQ ID NO: 82)
AS 3':   UU GGUUCAAAUUCCCUUUAUA    (SEQ ID NO: 83)

S 5':       GGUGUGCUCUGCUUAUGAU UU(SEQ ID NO: 84)
mRNA:    AT GGTGTGCTCTGCTTATGAT AA(SEQ ID NO: 85)
AS 3':   UU CCACACGAGACGAAUACUA    (SEQ ID NO: 86)

S 5':       GAGCAAAUGAAAGAUGUAU UU(SEQ ID NO: 87)
mRNA:    TC GAGCAAATGAAAGATGTAT AT(SEQ ID NO: 88)
AS 3':   UU CUCGUUUACUUUCUACAUA    (SEQ ID NO: 89)

S 5':       CAGAGCAAGAAGUCAUAAA UU(SEQ ID NO: 90)
mRNA:    TT CAGAGCAAGAAGTCATAAA GA(SEQ ID NO: 91)
AS 3':   UU GUCUCGUUCUUCAGUAUUU    (SEQ ID NO: 92)
```

```
S 5':    GUCCUCUUCUAAAUAGAAA UU(SEQ ID NO: 93)         S 5':    GCUUCAGACAUGAGAACAU UU(SEQ ID NO: 153)
mRNA:    GA GTCCTCTTCTAAATAGAAA AC(SEQ ID NO: 94)      mRNA:    GC GCTTCAGACATGAGAACAT CA(SEQ ID NO: 154)
AS 3':   UU CAGGAGAAGAUUUAUCUUU    (SEQ ID NO: 95)     AS 3':   UU CGAAGUCUGUACUCUUGUA    (SEQ ID NO: 155)

S 5':    CUGGCAGAAAUGCUUUCUA UU(SEQ ID NO: 96)         S 5':    GUUCCUUUAUUCACAAUCU UU(SEQ ID NO: 156)
mRNA:    TT CTGGCAGAAATGCTTTCTA AC(SEQ ID NO: 97)      mRNA:    AT GTTCCTTTATTCACAATCT TA(SEQ ID NO: 157)
AS 3':   UU GACCGUCUUUACGAAAGAU    (SEQ ID NO: 98)     AS 3':   UU CAAGGAAAUAAGUGUUAGA    (SEQ ID NO: 158)

S 5':    GCCUUGUUCAAUAAUUACU UU(SEQ ID NO: 99)         S 5':    GUGUCACUCUGUAGUUACU UU(SEQ ID NO: 159)
mRNA:    TT GCCTTGTTCAATAATTACT GT(SEQ ID NO: 100)     mRNA:    CA GTGTCACTCTGTAGTTACT GT(SEQ ID NO: 160)
AS 3':   UU CGGAACAAGUUAUUAAUGA    (SEQ ID NO: 101)    AS 3':   UU CACAGUGAGACAUCAAUGA    (SEQ ID NO: 161)

S 5':    GCUCCAGAAAUUAUGUUGA UU(SEQ ID NO: 102)        S 5':    GCUGUAAAGUGGAAGCAAU UU(SEQ ID NO: 162)
mRNA:    GG CTCCAGAAATTATGTTGA AT(SEQ ID NO: 103)      mRNA:    CA GCTGTAAAGTGGAAGCAAT AT(SEQ ID NO: 166)
AS 3':   UU CGAGGUCUUUAAUACAACU    (SEQ ID NO: 104)    AS 3':   UU CGACAUUUCACCUUCGUUA    (SEQ ID NO: 167)

S 5':    CCCAGCACUUGGAUUUACA UU(SEQ ID NO: 105)        S 5':    CCACAUGCCUACGAUUGAA UU(SEQ ID NO: 168)
mRNA:    GG CCCAGCACTTGGATTTACA TA(SEQ ID NO: 106)     mRNA:    TG CCACATGCCTACGATTGAA AT(SEQ ID NO: 169)
AS 3':   UU GGGUCGUGAACCUAAAUGU    (SEQ ID NO: 107)    AS 3':   UU GGGUGUACGGAUGCUAACUU   (SEQ ID NO: 170)

S 5':    GCCUUGUAUAUGGUAAAGA UU(SEQ ID NO: 108)        S 5':    GUCAGCAUCUCAAGUUCAU UU(SEQ ID NO: 171)
mRNA:    TT GCCTTGTATATGGTAAAGA TT(SEQ ID NO: 109)     mRNA:    AT GTCAGCATCTCAAGTTCAT TT(SEQ ID NO: 172)
AS 3':   UU CGGAACAUAUACCAUUUCU    (SEQ ID NO: 110)    AS 3':   UU CAGUCGUAGAGUUCAAGUA    (SEQ ID NO: 173)

S 5':    GCGCUAGCUAUCAUGUGUA UU(SEQ ID NO: 111)        S 5':    GGGACACAGAAAUGUGACU UU(SEQ ID NO: 174)
mRNA:    AA GCGCTAGCTATCATGTGTA GT(SEQ ID NO: 112)     mRNA:    AC GGGACACAGAAATGTGACT GT(SEQ ID NO: 175)
AS 3':   UU CGCGAUCGAUAGUACACAU    (SEQ ID NO: 113)    AS 3':   UU CCCUGUGUCUUUACACUGA    (SEQ ID NO: 176)

S 5':    GGAGUCAGAUUGGCAUGAA UU(SEQ ID NO: 114)        S 5':    CCAGUGGGAUGGAAUUGAA UU(SEQ ID NO: 177)
mRNA:    GT GGAGTCAGATTGGCATGAA AC(SEQ ID NO: 115)     mRNA:    AG CCAGTGGGATGGAATTGAA AG(SEQ ID NO: 178)
AS 3':   UU CCUCAGUCUAACCGUACUU    (SEQ ID NO: 116)    AS 3':   UU GGUCACCCUACCUUAACUU    (SEQ ID NO: 179)

S 5':    GCAUCUGGGUAGAAGAAUA UU(SEQ ID NO: 117)        S 5':    CCUGCUAAUAUGAACAGAA UU(SEQ ID NO: 180)
mRNA:    TG GCATCTGGGTAGAAGAATA CT(SEQ ID NO: 118)     mRNA:    TG CCTGCTAATATGAACAGAA AT(SEQ ID NO: 181)
AS 3':   UU CGUAGACCCAUCUUCUUAU    (SEQ ID NO: 119)    AS 3':   UU GGACGAUUAUACUUGUCUU    (SEQ ID NO: 182)

S 5':    GGCAUUAUGUAAUGACUUA UU(SEQ ID NO: 120)        S 5':    CUGCUAAUAUGAACAGAAA UU(SEQ ID NO: 183)
mRNA:    TG GGCATTATGTAATGACTTA TT(SEQ ID NO: 121)     mRNA:    GC CTGCTAATATGAACAGAAA TG(SEQ ID NO: 184)
AS 3':   UU CCGUAAUACAUUACUGAAU    (SEQ ID NO: 122)    AS 3':   UU GACGAUUAUACUUGUCUUU    (SEQ ID NO: 185)

S 5':    GCUCUUCUUACAUUUGUAA UU(SEQ ID NO: 123)        S 5':    GAGUCAGAUUGGCAUGAAA UU(SEQ ID NO: 186)
mRNA:    TG GCTCTTCTTACATTTGTAA AA(SEQ ID NO: 124)     mRNA:    TG GAGTCAGATTGGCATGAAA CC(SEQ ID NO: 187)
AS 3':   UU CGAGAAGAAUGUAAACAUU    (SEQ ID NO: 125)    AS 3':   UU CUCAGUCUAACCGUACUUU    (SEQ ID NO: 188)

S 5':    GCUGGUGUUUGAAACAUGA UU(SEQ ID NO: 126)        S 5':    CUGCCUGCUAAUAUGAACA UU(SEQ ID NO: 189)
mRNA:    AT GCTGGTGTTTGAAACATGA TA(SEQ ID NO: 127)     mRNA:    GA CTGCCTGCTAATATGAACA GA(SEQ ID NO: 190)
AS 3':   UU CGACCACAAACUUUGUACU    (SEQ ID NO: 128)    AS 3':   UU GACGGACGAUUAUACUUGU    (SEQ ID NO: 191)

S 5':    GGGCACUUUAAGUCAGUGA UU(SEQ ID NO: 129)        S 5':    CGUCUUUAAAUGAGAAAGU UU(SEQ ID NO: 192)
mRNA:    TA GGGCACTTTAAGTCAGTGA CA(SEQ ID NO: 130)     mRNA:    TG CGTCTTTAAATGAGAAAGT AT(SEQ ID NO: 193)
AS 3':   UU CCCGUGAAAUUCAGUCACU    (SEQ ID NO: 131)    AS 3':   UU GCAGAAAUUUACUCUUUCA    (SEQ ID NO: 194)

S 5':    GCAGUACUUAAUGUUUGUA UU(SEQ ID NO: 132)        S 5':    GCUACACCAAGUCCAUUGA UU(SEQ ID NO: 195)
mRNA:    GT GCAGTACTTAATGTTTGTA AG(SEQ ID NO: 133)     mRNA:    GG GCTACACCAAGTCCATTGA TA(SEQ ID NO: 196)
AS 3':   UU CGUCAUGAAUUACAAACAU    (SEQ ID NO: 134)    AS 3':   UU CGAUGUGGUUCAGGUAACU    (SEQ ID NO: 197)

S 5':    CAGAUUAGGUCAUCUUAAU UU(SEQ ID NO: 135)        S 5':    CAGGGAAGCAUUAUCUUGA UU(SEQ ID NO: 198)
mRNA:    TA CAGATTAGGTCATCTTAAT TC(SEQ ID NO: 136)     mRNA:    TC CAGGGAAGCATTATCTTGA CC(SEQ ID NO: 199)
AS 3':   UU GUCUAAUCCAGUAGAAUUA    (SEQ ID NO: 137)    AS 3':   UU GUCCCUUCGUAAUAGAACU    (SEQ ID NO: 200)

S 5':    GGUGAGAAAUUUGCCUUGU UU(SEQ ID NO: 138)        S 5':    CUCCAAAGCUCUGGACUUA UU(SEQ ID NO: 201)
mRNA:    GT GGTGAGAAATTTGCCTTGT TC(SEQ ID NO: 139)     mRNA:    GA CTCCAAAGCTCTGGACTTA TT(SEQ ID NO: 202)
AS 3':   UU CCACUCUUUAAACGGAACA    (SEQ ID NO: 140)    AS 3':   UU GAGGUUUCGAGACCUGAAU    (SEQ ID NO: 203)

S 5':    GAAGCUAUAACAGUGAAUA UU(SEQ ID NO: 141)        S 5':    GCAAUGGAGAAUGGGUUAU UU(SEQ ID NO: 204)
mRNA:    GA GAAGCTATAACAGTGAATA TG(SEQ ID NO: 142)     mRNA:    CA GCAATGGAGAATGGGTTAT AT(SEQ ID NO: 205)
AS 3':   UU CUUCGAUAUUGUCACUUAU    (SEQ ID NO: 143)    AS 3':   UU CGUUACCUCUUACCCAAUA    (SEQ ID NO: 206)

S 5':    GAAGACCUGAAUUGUAUAA UU(SEQ ID NO: 144)        S 5':    GGGUCAGAAACAAAUGGAA UU(SEQ ID NO: 207)
mRNA:    AA GAAGACCTGAATTGTATAA TA(SEQ ID NO: 145)     mRNA:    AT GGGTCAGAAACAAATGGAA AT(SEQ ID NO: 208)
AS 3':   UU CUUCUGGACUUAACAUAUU    (SEQ ID NO: 146)    AS 3':   UU CCCAGUCUUUGUUUACCUU    (SEQ ID NO: 209)

S 5':    GAGCACUCAAGAAAGUUCU UU(SEQ ID NO: 147)        S 5':    GUACCAUAUAGAGGUGUAA UU(SEQ ID NO: 210)
mRNA:    TA GAGCACTCAAGAAAGTTCT GA(SEQ ID NO: 148)     mRNA:    TT GTACCATATAGAGGTGTAA CA(SEQ ID NO: 211)
AS 3':   UU CUCGUGAGUUCUUUCAAGA    (SEQ ID NO: 149)    AS 3':   UU CAUGGUAUAUCUCCACAUU    (SEQ ID NO: 212)

S 5':    CUCCAGAAAUUAUGUUGAA UU(SEQ ID NO: 150)        S 5':    GUGGGUGUUUCAGUAACCA UU(SEQ ID NO: 213)
mRNA:    GG CTCCAGAAATTATGTTGAA TT(SEQ ID NO: 151)     mRNA:    AT GTGGGTGTTTCAGTAACCA CG(SEQ ID NO: 214)
AS 3':   UU GAGGUCUUUAAUACAACUU    (SEQ ID NO: 152)    AS 3':   UU CACCCACAAAGUCAUUGGU    (SEQ ID NO: 215)
```

```
S 5':      GUAGAGCACUCAAGAAAGU UU(SEQ ID NO: 216)      S 5':      GUCUAGUCCUUCGUUAUGU UU(SEQ ID NO: 276)
mRNA:   GT GTAGAGCACTCAAGAAAGT TC(SEQ ID NO: 217)      mRNA:   TT GTCTAGTCCTTCGTTATGT TC(SEQ ID NO: 277)
AS 3':  UU CAUCUCGUGAGUUCUUUCA    (SEQ ID NO: 218)     AS 3':  UU CAGAUCAGGAAGCAAUACA    (SEQ ID NO: 278)

S 5':      CCAGUCCUUUCAUUUAGUA UU(SEQ ID NO: 219)      S 5':      GUGUCCCUGUAUUACCAAA UU(SEQ ID NO: 279)
mRNA:   TT CCAGTCCTTTCATTTAGTA TA(SEQ ID NO: 220)      mRNA:   TT GTGTCCCTGTATTACCAAA AT(SEQ ID NO: 280)
AS 3':  UU GGUCAGGAAAGUAAAUCAU    (SEQ ID NO: 221)     AS 3':  UU CACAGGGACAUAAUGGUUU    (SEQ ID NO: 281)

S 5':      GCCUGCUAAUAUGAACAGA UU(SEQ ID NO: 222)      S 5':      CAGCAUGUCAGCAUCUCAA UU(SEQ ID NO: 282)
mRNA:   CT GCCTGCTAATATGAACAGA AA(SEQ ID NO: 223)      mRNA:   TA CAGCATGTCAGCATCTCAA GT(SEQ ID NO: 283)
AS 3':  UU CGGACGAUUAUACUUGUCU    (SEQ ID NO: 224)     AS 3':  UU GUCGUACAGUCGUAGAGUU    (SEQ ID NO: 284)

S 5':      CAGUGAAUAUGUGGUUUCU UU(SEQ ID NO: 225)      S 5':      GUGUAACACUUGUCAAGAA UU(SEQ ID NO: 285)
mRNA:   AA CAGTGAATATGTGGTTTCT CT(SEQ ID NO: 226)      mRNA:   AG GTGTAACACTTGTCAAGAA GC(SEQ ID NO: 286)
AS 3':  UU GUCACUUAUACACCAAAGA    (SEQ ID NO: 227)     AS 3':  UU CACAUUGUGAACAGUUCUU    (SEQ ID NO: 287)

S 5':      GAGUCCUCUUCUAAAUAGA UU(SEQ ID NO: 228)      S 5':      GUGUAGAGCACUCAAGAAA UU(SEQ ID NO: 288)
mRNA:   TG GAGTCCTCTTCTAAATAGA AA(SEQ ID NO: 229)      mRNA:   GC GTGTAGAGCACTCAAGAAA GT(SEQ ID NO: 289)
AS 3':  UU CUCAGGAGAAGAUUUAUCU    (SEQ ID NO: 230)     AS 3':  UU CACAUCUCGUGAGUUCUUU    (SEQ ID NO: 290)

S 5':      GUCACUUGUACCAUAUAGA UU(SEQ ID NO: 231)      S 5':      CAGCAGAUCAUUUAGGAAA UU(SEQ ID NO: 291)
mRNA:   TG GTCACTTGTACCATATAGA GG(SEQ ID NO: 232)      mRNA:   TC CAGCAGATCATTTAGGAAA AA(SEQ ID NO: 292)
AS 3':  UU CAGUGAACAUGGUAUAUCU    (SEQ ID NO: 233)     AS 3':  UU GUCGUCUAGUAAAUCCUUU    (SEQ ID NO: 293)

S 5':      CUAUCCAGCAGAUCAUUUA UU(SEQ ID NO: 234)      S 5':      CAGAUCCUCAGAGGGUUAA UU(SEQ ID NO: 294)
mRNA:   TG CTATCCAGCAGATCATTTA GG(SEQ ID NO: 235)      mRNA:   AC CAGATCCTCAGAGGGTTAA AA(SEQ ID NO: 295)
AS 3':  UU GAUAGGUCGUCUAGUAAAU    (SEQ ID NO: 236)     AS 3':  UU GUCUAGGAGUCUCCCAAUU    (SEQ ID NO: 296)

S 5':      CUGGGUAGAAGAAUACUGU UU(SEQ ID NO: 237)      S 5':      GAACAUCAUUGGAAUCAAU UU(SEQ ID NO: 297)
mRNA:   AT CTGGGTAGAAGAATACTGT AT(SEQ ID NO: 238)      mRNA:   GA GAACATCATTGGAATCAAT GA(SEQ ID NO: 298)
AS 3':  UU GACCCAUCUUCUUAUGACA    (SEQ ID NO: 239)     AS 3':  UU CUUGUAGUAACCUUAGUUA    (SEQ ID NO: 299)

S 5':      CCAUCGAGCAAAUGAAAGA UU(SEQ ID NO: 240)      S 5':      GCUAUCAUGUGUAGUAGAU UU(SEQ ID NO: 300)
mRNA:   AA CCATCGAGCAAATGAAAGA TG(SEQ ID NO: 241)      mRNA:   TA GCTATCATGTGTAGTAGAT GC(SEQ ID NO: 301)
AS 3':  UU GGUAGCUCGUUUACUUUCU    (SEQ ID NO: 242)     AS 3':  UU CGAUAGUACACAUCAUCUA    (SEQ ID NO: 302)

S 5':      CUGUCCUCAAGUACUCAAA UU(SEQ ID NO: 243)      S 5':      CUGCUUAUGAUAAUGUCAA UU(SEQ ID NO: 303)
mRNA:   TT CTGTCCTCAAGTACTCAAA TA(SEQ ID NO: 244)      mRNA:   CT CTGCTTATGATAATGTCAA CA(SEQ ID NO: 304)
AS 3':  UU GACAGGAGUUCAUGAGUUU    (SEQ ID NO: 245)     AS 3':  UU GACGAAUACUAUUACAGUU    (SEQ ID NO: 305)

S 5':      GCACCAUUCAAGUUCGACA UU(SEQ ID NO: 246)      S 5':      CUUGGCUUAUCCACUUUGA UU(SEQ ID NO: 306)
mRNA:   AA GCACCATTCAAGTTCGACA TG(SEQ ID NO: 247)      mRNA:   GT CTTGGCTTATCCACTTTGA CT(SEQ ID NO: 307)
AS 3':  UU CGUGGUAAGUUCAAGCUGU    (SEQ ID NO: 248)     AS 3':  UU GAACCGAAUAGGUGAAACU    (SEQ ID NO: 308)

S 5':      CCUCAAAGCUAGCAGAGAU UU(SEQ ID NO: 249)      S 5':      GUCUCAAAUAUUCUGUCAA UU(SEQ ID NO: 309)
mRNA:   GT CCTCAAAGCTAGCAGAGAT AC(SEQ ID NO: 250)      mRNA:   AG GTCTCAAATATTCTGTCAA AC(SEQ ID NO: 310)
AS 3':  UU GGAGUUUCGAUCGUCUCUA    (SEQ ID NO: 251)     AS 3':  UU CAGAGUUUAUAAGACAGUU    (SEQ ID NO: 311)

S 5':      CAUGCCACGUAAUAUUUCA UU(SEQ ID NO: 252)      S 5':      GCUUUCUGGUUUGAAAGAU UU(SEQ ID NO: 312)
mRNA:   CA CATGCCACGTAATATTTCA GC(SEQ ID NO: 253)      mRNA:   TT GCTTTCTGGTTTGAAAGAT GC(SEQ ID NO: 313)
AS 3':  UU GUACGGUGCAUUAUAAAGU    (SEQ ID NO: 254)     AS 3':  UU CGAAAGACCAAACUUUCUA    (SEQ ID NO: 314)

S 5':      CACCAUUCAAGUUCGACAU UU(SEQ ID NO: 255)      S 5':      CAACCAUCGAGCAAAUGAA UU(SEQ ID NO: 315)
mRNA:   AG CACCATTCAAGTTCGACAT GG(SEQ ID NO: 256)      mRNA:   AC CAACCATCGAGCAAATGAA AG(SEQ ID NO: 316)
AS 3':  UU GUGGUAAGUUCAAGCUGUA    (SEQ ID NO: 257)     AS 3':  UU GUUGGUAGCUCGUUUACUU    (SEQ ID NO: 317)

S 5':      GUUAUGUGCAGUACUUAAU UU(SEQ ID NO: 258)      S 5':      CAUCGAGCAAAUGAAAGAU UU(SEQ ID NO: 318)
mRNA:   GC GTTATGTGCAGTACTTAAT GT(SEQ ID NO: 259)      mRNA:   AC CATCGAGCAAATGAAAGAT GT(SEQ ID NO: 319)
AS 3':  UU CAAUACACGUCAUGAAUUA    (SEQ ID NO: 260)     AS 3':  UU GUAGCUCGUUUACUUUCUA    (SEQ ID NO: 320)

S 5':      CCUUGUAUAUGGUAAAGAU UU(SEQ ID NO: 261)      S 5':      GUUCAGCAUAGUACUUCAA UU(SEQ ID NO: 321)
mRNA:   TG CCTTGTATATGGTAAAGAT TA(SEQ ID NO: 262)      mRNA:   CT GTTCAGCATAGTACTTCAA AG(SEQ ID NO: 322)
AS 3':  UU GGAACAUAUACCAUUUCUA    (SEQ ID NO: 263)     AS 3':  UU CAAGUCGUAUCAUGAAGUU    (SEQ ID NO: 323)

S 5':      CCCAAAUGCUGACUCCAAA UU(SEQ ID NO: 264)      S 5':      CCACUAACUUCAUUCUAGA UU(SEQ ID NO: 324)
mRNA:   TT CCCAAATGCTGACTCCAAA GC(SEQ ID NO: 265)      mRNA:   AA CCACTAACTTCATTCTAGA AT(SEQ ID NO: 325)
AS 3':  UU GGGUUUACGACUGAGGUUU    (SEQ ID NO: 266)     AS 3':  UU GGUGAUUGAAGUAAGAUCU    (SEQ ID NO: 326)

S 5':      GGAUGGAAUUGAAAGAACU UU(SEQ ID NO: 267)      S 5':      CACCUCAGCAAUGACCAUA UU(SEQ ID NO: 327)
mRNA:   TG GGATGGAATTGAAAGAACT AA(SEQ ID NO: 268)      mRNA:   AA CACCTCAGCAATGACCATA TC(SEQ ID NO: 328)
AS 3':  UU CCUACCUUAACUUUCUUGA    (SEQ ID NO: 269)     AS 3':  UU GUGGAGUCGUUACUGGUAU    (SEQ ID NO: 329)

S 5':      CUGCGUCUUUAAAUGAGAA UU(SEQ ID NO: 270)      S 5':      CAGUGUCACUCUGUAGUUA UU(SEQ ID NO: 330)
mRNA:   CA CTGCGTCTTTAAATGAGAA AG(SEQ ID NO: 271)      mRNA:   AG CAGTGTCACTCTGTAGTTA CT(SEQ ID NO: 331)
AS 3':  UU GACGCAGAAAUUUACUCUU    (SEQ ID NO: 272)     AS 3':  UU GUCACAGUGAGACAUCAAU    (SEQ ID NO: 332)

S 5':      GCCAUUCAGAGGAAACUGU UU(SEQ ID NO: 273)      S 5':      CUAGCUAUCAUGUGUAGUA UU(SEQ ID NO: 333)
mRNA:   CA GCCATTCAGAGGAAACTGT TT(SEQ ID NO: 274)      mRNA:   CG CTAGCTATCATGTGTAGTA GA(SEQ ID NO: 334)
AS 3':  UU CGGUAAGUCUCCUUUGACA    (SEQ ID NO: 275)     AS 3':  UU GAUCGAUAGUACACAUCAU    (SEQ ID NO: 335)
```

```
S 5':       GUAGCUUUGAGAAGCUACA UU(SEQ ID NO: 336)        S 5':       GAGUUAGAAAGGUACUUCU UU(SEQ ID NO: 396)
mRNA:    CA GUAGCUUUGAGAAGCUACA TG(SEQ ID NO: 337)        mRNA:    AT GAGTTAGAAAGGTACTTCT GT(SEQ ID NO: 397)
AS 3':   UU CAUCGAAACUCUUCGAUGU    (SEQ ID NO: 338)       AS 3':   UU CUCAAUCUUUCCAUGAAGA   (SEQ ID NO: 398)

S 5':       GUCAAACCCUAACAAAGAA UU(SEQ ID NO: 339)        S 5':       GUCACUCUGUAGUUACUGU UU(SEQ ID NO: 399)
mRNA:    CT GTCAAACCCTAACAAAGAA GC(SEQ ID NO: 340)        mRNA:    GT GTCACTCTGTAGTTACTGT GG(SEQ ID NO: 400)
AS 3':   UU CAGUUUGGGAUUGUUUCUU    (SEQ ID NO: 341)       AS 3':   UU CAGUGAGACAUCAAUGACA   (SEQ ID NO: 401)

S 5':       GACAUUUGGUUCUUAUCAA UU(SEQ ID NO: 342)        S 5':       CACUCAAGAAAGUUCUGAA UU(SEQ ID NO: 402)
mRNA:    TG GACATTTGGTTCTTATCAA TA(SEQ ID NO: 343)        mRNA:    AG CACTCAAGAAAGTTCTGAA AC(SEQ ID NO: 403)
AS 3':   UU CUGUAAACCAAGAAUAGUU    (SEQ ID NO: 344)       AS 3':   UU GUGAGUUCUUUCAAGACUU   (SEQ ID NO: 404)

S 5':       GUGUUUGAAACAUGAUACU UU(SEQ ID NO: 345)        S 5':       GACACAGAAAUGUGACUGU UU(SEQ ID NO: 405)
mRNA:    TG GTGTTTGAAACATGATACT CC(SEQ ID NO: 346)        mRNA:    GG GACACAGAAATGTGACTGT TA(SEQ ID NO: 406)
AS 3':   UU CACAAACUUUGUACUAUGA    (SEQ ID NO: 347)       AS 3':   UU CUGUGUCUUUACACUGACA   (SEQ ID NO: 407)

S 5':       GAGAACAUCAUUGGAAUCA UU(SEQ ID NO: 348)        S 5':       CACAUGCCUACGAUUGAAA UU(SEQ ID NO: 408)
mRNA:    AT GAGAACATCATTGGAATCA AT(SEQ ID NO: 349)        mRNA:    GC CACATGCCTACGATTGAAA TG(SEQ ID NO: 409)
AS 3':   UU CUCUUGUAGUAACCUUAGU    (SEQ ID NO: 350)       AS 3':   UU GUGUACGGAUGCUAACUUU   (SEQ ID NO: 410)

S 5':       GUUGUGCUGAACACAGAAA UU(SEQ ID NO: 351)        S 5':       GACAUUUGGUGAGAGAAGU UU(SEQ ID NO: 411)
mRNA:    AG GTTGTGCTGAACACAGAAA TG(SEQ ID NO: 352)        mRNA:    TC GACATTTGGTGAGAAGT AC(SEQ ID NO: 412)
AS 3':   UU CAACACGACUUGUGUCUUU    (SEQ ID NO: 353)       AS 3':   UU CUGUAAACCACUCUCUUCA   (SEQ ID NO: 413)

S 5':       GCUUUCUCUUCCACACAAA UU(SEQ ID NO: 354)        S 5':       GUCCAUUGAUAUUUGGUCU UU(SEQ ID NO: 414)
mRNA:    TT GCTTTCTCTTCCACACAAA AA(SEQ ID NO: 355)        mRNA:    AA GTCCATTGATATTTGGTCT GT(SEQ ID NO: 415)
AS 3':   UU CGAAAGAGAAGGUGUGUUU    (SEQ ID NO: 356)       AS 3':   UU CAGGUAACUAUAAACCAGA   (SEQ ID NO: 416)

S 5':       GUUGGUGCCUUCUUGGUAU UU(SEQ ID NO: 357)        S 5':       CCAUAUCCUUGGCUACUAA UU(SEQ ID NO: 417)
mRNA:    CT GTTGGTGCCTTCTTGGTAT TG(SEQ ID NO: 358)        mRNA:    AA CCATATCCTTGGCTACTAA CA(SEQ ID NO: 418)
AS 3':   UU CAACCACGGAAGAACCAUA    (SEQ ID NO: 359)       AS 3':   UU GGUAUAGGAACCGAUGAUU   (SEQ ID NO: 419)

S 5':       CUUGGACAUUUGGUUCUUA UU(SEQ ID NO: 360)        S 5':       CAGCUGUAAAGUGGAAGCA UU(SEQ ID NO: 420)
mRNA:    TT CTTGGACATTTGGTTCTTA TC(SEQ ID NO: 361)        mRNA:    GT CAGCTGTAAAGTGGAAGCA AT(SEQ ID NO: 421)
AS 3':   UU GAACCUGUAAACCAAGAAU    (SEQ ID NO: 362)       AS 3':   UU GUCGACAUUUCACCUUCGU   (SEQ ID NO: 422)

S 5':       CCUGCUGAAACAUUCCAGU UU(SEQ ID NO: 363)        S 5':       GCUGAAACAUUCCAGUCCU UU(SEQ ID NO: 423)
mRNA:    TT CCTGCTGAAACATTCCAGT CC(SEQ ID NO: 364)        mRNA:    CT GCTGAAACATTCCAGTCCT TT(SEQ ID NO: 424)
AS 3':   UU GGACGACUUUGUAAGGUCA    (SEQ ID NO: 365)       AS 3':   UU CGACUUUGUAAGGUCAGGA   (SEQ ID NO: 425)

S 5':       CCAGUAGCUUUGAGAAGCU UU(SEQ ID NO: 366)        S 5':       CACAAUCUUAGGUCUCAAA UU(SEQ ID NO: 426)
mRNA:    AA CCAGTAGCTTTGAGAAGCT AC(SEQ ID NO: 367)        mRNA:    TT CACAATCTTAGGTCTCAAA TA(SEQ ID NO: 427)
AS 3':   UU GGUCAUCGAAACUCUUCGA    (SEQ ID NO: 368)       AS 3':   UU GUGUUAGAAUCCAGAGUUU   (SEQ ID NO: 428)

S 5':       GGUCUCAAAUAUUCUGUCA UU(SEQ ID NO: 369)        S 5':       CUGAGUCAGACUGUCAGAA UU(SEQ ID NO: 429)
mRNA:    TA GGTCTCAAATATTCTGTCA AA(SEQ ID NO: 370)        mRNA:    TG CTGAGTCAGACTGTCAGAA AA(SEQ ID NO: 430)
AS 3':   UU CCAGAGUUUAUAAGACAGU    (SEQ ID NO: 371)       AS 3':   UU GACUCAGUCUGACAGUCUU   (SEQ ID NO: 431)

S 5':       GAACAGAAAUGCAUUUGUA UU(SEQ ID NO: 372)        S 5':       GACUGUUACAGCUUUCUGU UU(SEQ ID NO: 432)
mRNA:    AT GAACAGAAATGCATTTGTA AT(SEQ ID NO: 373)        mRNA:    AT GACTGTTACAGCTTTCTGT GC(SEQ ID NO: 433)
AS 3':   UU CUUGUCUUUACGUAAACAU    (SEQ ID NO: 374)       AS 3':   UU CUGACAAUGUCGAAAGACA   (SEQ ID NO: 434)

S 5':       GUCCUAACCAAGGUACCUA UU(SEQ ID NO: 375)        S 5':       GUACUUCAAAGCAAGUACU UU(SEQ ID NO: 435)
mRNA:    TG GTCCTAACCAAGGTACCTA TG(SEQ ID NO: 376)        mRNA:    TA GTACTTCAAAGCAAGTACT CA(SEQ ID NO: 436)
AS 3':   UU CAGGAUUGGUUCCAUGGAU    (SEQ ID NO: 377)       AS 3':   UU CAUGAAGUUUCGUUCAUGA   (SEQ ID NO: 437)

S 5':       GCACUCAAGAAAGUUCUGA UU(SEQ ID NO: 378)        S 5':       CAUGUGGUAACUUGUGUUA UU(SEQ ID NO: 438)
mRNA:    GA GCACTCAAGAAAGTTCTGA AA(SEQ ID NO: 379)        mRNA:    TG CATGTGGTAACTTGTGTTA GG(SEQ ID NO: 439)
AS 3':   UU CGUGAGUUCUUUCAAGACU    (SEQ ID NO: 380)       AS 3':   UU GUACACCAUUGAACACAAU   (SEQ ID NO: 440)

S 5':       CAUGAUGGGUCAGAAACAA UU(SEQ ID NO: 381)        S 5':       GGAACUAUUUGCUUUCUCU UU(SEQ ID NO: 441)
mRNA:    GA CATGATGGGTCAGAAACAA AT(SEQ ID NO: 382)        mRNA:    TA GGAACTATTTGCTTTCTCT TC(SEQ ID NO: 442)
AS 3':   UU GUACUACCCAGUCUUUGUU    (SEQ ID NO: 383)       AS 3':   UU CCUUGAUAAACGAAAGAGA   (SEQ ID NO: 443)

S 5':       CAAUGGAGAAUGGGUUAUA UU(SEQ ID NO: 384)        S 5':       GAUCUUUACAAGCUCUUGA UU(SEQ ID NO: 444)
mRNA:    AG CAATGGAGAATGGGTTATA TA(SEQ ID NO: 385)        mRNA:    CA GATCTTTACAAGCTCTTGA AG(SEQ ID NO: 445)
AS 3':   UU GUUACCUCUUACCCAAUAU    (SEQ ID NO: 386)       AS 3':   UU CUAGAAAUGUUCGAGAACU   (SEQ ID NO: 446)

S 5':       CUCUAUUCUUGCCCUGAAA UU(SEQ ID NO: 387)        S 5':       CAGAUGAGAAGCUAUAACA UU(SEQ ID NO: 447)
mRNA:    AT CTCTATTCTTGCCCTGAAA TA(SEQ ID NO: 388)        mRNA:    TG CAGATGAGAAGCTATAACA GT(SEQ ID NO: 448)
AS 3':   UU GAGAUAAGAACGGGACUUU    (SEQ ID NO: 389)       AS 3':   UU GUCUACUCUUCGAUAUUGU   (SEQ ID NO: 449)

S 5':       CUUCUAUCUUCACAUUCAU UU(SEQ ID NO: 390)        S 5':       CUCUGGACUUAUUGGACAA UU(SEQ ID NO: 450)
mRNA:    AT CTTCTATCTTCACATTCAT GT(SEQ ID NO: 391)        mRNA:    AG CTCTGGACTTATTGGACAA AA(SEQ ID NO: 451)
AS 3':   UU GAAGAUAGAAGUGUAAGUA    (SEQ ID NO: 392)       AS 3':   UU GAGACCUGAAUAACCUGUU   (SEQ ID NO: 452)

S 5':       GUACUUCAGUGCACCUACU UU(SEQ ID NO: 393)        S 5':       GCUUAUGAUAAUGUCAACA UU(SEQ ID NO: 453)
mRNA:    AT GTACTTCAGTGCACCTACT GC(SEQ ID NO: 394)        mRNA:    CT GCTTATGATAATGTCAACA AA(SEQ ID NO: 454)
AS 3':   UU CAUGAAGUCACGUGGAUGA    (SEQ ID NO: 395)       AS 3':   UU CGAAUACUAUUACAGUUGU   (SEQ ID NO: 455)
```

```
S    5':       GCUUUGAGAAGCUACAUGU UU(SEQ ID NO: 456)
mRNA:       TA GCTTTGAGAAGCTACATGT AG(SEQ ID NO: 457)
AS   3':    UU CGAAACUCUUCGAUGUACA    (SEQ ID NO: 458)

S    5':       CCUACUGCUUACUGUUGCU UU(SEQ ID NO: 459)
mRNA:       CA CCTACTGCTTACTGTTGCT TT(SEQ ID NO: 460)
AS   3':    UU GGAUGACGAAUGACAACGA    (SEQ ID NO: 461)

S    5':       CCUGAGGAUUUAGCAGAGA UU(SEQ ID NO: 462)
mRNA:       TG CCTGAGGATTTAGCAGAGA GG(SEQ ID NO: 463)
AS   3':    UU GGACUCCUAAAUCGUCUCU    (SEQ ID NO: 464)

S    5':       CAUAUCUGGAGCAGUAUUA UU(SEQ ID NO: 465)
mRNA:       CC CATATCTGGAGCAGTATTA CG(SEQ ID NO: 466)
AS   3':    UU GUAUAGACCUCGUCAUAAU    (SEQ ID NO: 467)

S    5':       CACAACACCUCAGCAAUGA UU(SEQ ID NO: 468)
mRNA:       GA CACAACACCTCAGCAATGA CC(SEQ ID NO: 469)
AS   3':    UU GUGUUGUGGAGUCGUUACU    (SEQ ID NO: 470)

S    5':       CUGUUGCUUUAGUCACUAA UU(SEQ ID NO: 471)
mRNA:       TA CTGTTGCTTTAGTCACTAA TT(SEQ ID NO: 472)
AS   3':    UU GACAACGAAAUCAGUGAUU    (SEQ ID NO: 473)

S    5':       CAAGAGGAUUGAAGUAGAA UU(SEQ ID NO: 474)
mRNA:       CA CAAGAGGATTGAAGTAGAA CA(SEQ ID NO: 475)
AS   3':    UU GUUCUCCUAACUUCAUCUU    (SEQ ID NO: 476)

S    5':       GAGUUGUGUUCCACGGAAA UU(SEQ ID NO: 477)
mRNA:       CT GAGTTGTGTTCCACGGAAA AT(SEQ ID NO: 478)
AS   3':    UU CUCAACACAAGGUGCCUUU    (SEQ ID NO: 479)

S    5':       CACUUGGAUUUACAUAAGA UU(SEQ ID NO: 480)
mRNA:       AG CACTTGGATTTACATAAGA TG(SEQ ID NO: 481)
AS   3':    UU GUGAACCUAAAUGUAUUCU    (SEQ ID NO: 482)

S    5':       GUGUCUGAAUGGACAGUCA UU(SEQ ID NO: 483)
mRNA:       GC GTGTCTGAATGGACAGTCA GG(SEQ ID NO: 484)
AS   3':    UU CACAGACUUACCUGUCAGU    (SEQ ID NO: 485)

S    5':       CUUGCCUUGUAUAUGGUAA UU(SEQ ID NO: 486)
mRNA:       TA CTTGCCTTGTATATGGTAA AG(SEQ ID NO: 487)
AS   3':    UU GAACGGAACAUAUACCAUU    (SEQ ID NO: 488)

S    5':       GAGAAGCUAUAACAGUGAA UU(SEQ ID NO: 489)
mRNA:       AT GAGAAGCTATAACAGTGAA TA(SEQ ID NO: 490)
AS   3':    UU CUCUUCGAUAUUGUCACUU    (SEQ ID NO: 491)

S    5':       CUCAAAGCUAGCAGAGAUA UU(SEQ ID NO: 492)
mRNA:       TC CTCAAAGCTAGCAGAGATA CG(SEQ ID NO: 493)
AS   3':    UU GAGUUUCGAUCGUCUCUAU    (SEQ ID NO: 494)

S    5':       GUGAUUUGGUUAAUCUGUA UU(SEQ ID NO: 495)
mRNA:       TT GTGATTTGGTTAATCTGTA TA(SEQ ID NO: 496)
AS   3':    UU CACUAAACCAAUUAGACAU    (SEQ ID NO: 497)

S    5':       GCUCUGGACUUAUUGGACA UU(SEQ ID NO: 498)
mRNA:       AA GCTCTGGACTTATTGGACA AA(SEQ ID NO: 499)
AS   3':    UU CGAGACCUGAAUAACCUGU    (SEQ ID NO: 500)

S    5':       CACAUACAUACGCACACAU UU(SEQ ID NO: 501)
mRNA:       CA CACATACATACGCACACAT GC(SEQ ID NO: 502)
AS   3':    UU GUGUAUGUAUGCGUGUGUA    (SEQ ID NO: 503)

S    5':       CACUUGUCAAGAAGCGUUA UU(SEQ ID NO: 504)
mRNA:       AA CACTTGTCAAGAAGCGTTA TG(SEQ ID NO: 505)
AS   3':    UU GUGAACAGUUCUUCGCAAU    (SEQ ID NO: 506)

S    5':       CUGGUUUGAAAGAUGCAGU UU(SEQ ID NO: 507)
mRNA:       TT CTGGTTTGAAAGATGCAGT GG(SEQ ID NO: 508)
AS   3':    UU GACCAAACUUUCUACGUCA    (SEQ ID NO: 509)

S    5':       GUCUCUGCUUUCUUCCUCU UU(SEQ ID NO: 510)
mRNA:       GC GTCTCTGCTTTCTTCCTCT GC(SEQ ID NO: 511)
AS   3':    UU CAGAGACGAAAGAAGGAGA    (SEQ ID NO: 512)

S    5':       CUCAGUAAAUAGCAAGUCU UU(SEQ ID NO: 513)
mRNA:       TA CTCAGTAAATAGCAAGTCT TT(SEQ ID NO: 514)
AS   3':    UU GAGUCAUUUAUCGUUCAGA    (SEQ ID NO: 515)

S    5':       GAUCUCAAGAUCUGUGACU UU(SEQ ID NO: 516)
mRNA:       GT GATCTCAAGATCTGTGACT TT(SEQ ID NO: 517)
AS   3':    UU CUAGAGUUCUAGACACUGA    (SEQ ID NO: 518)

S    5':       CAUCACAAGAAGACCUGAA UU(SEQ ID NO: 519)
mRNA:       CC CATCACAAGAAGACCTGAA TT(SEQ ID NO: 520)
AS   3':    UU GUAGUGUUCUUCUGGACUU    (SEQ ID NO: 521)

S    5':       CUCGACAUUUGGUGAGAGA UU(SEQ ID NO: 522)
mRNA:       CA CTCGACATTTGGTGAGAGA AG(SEQ ID NO: 523)
AS   3':    UU GAGCUGUAAACCACUCUCU    (SEQ ID NO: 524)

S    5':       GUAGAGGUAACCAGUAGCU UU(SEQ ID NO: 525)
mRNA:       GT GTAGAGGTAACCAGTAGCT TT(SEQ ID NO: 526)
AS   3':    UU CAUCUCCAUUGGUCAUCGA    (SEQ ID NO: 527)

S    5':       GAUAGGAUUUCUUGGACAU UU(SEQ ID NO: 528)
mRNA:       AA GATAGGATTTCTTGGACAT TT(SEQ ID NO: 529)
AS   3':    UU CUAUCCUAAAGAACCUGUA    (SEQ ID NO: 530)

S    5':       CAUGAAACCACUAACUUCA UU(SEQ ID NO: 531)
mRNA:       GG CATGAAACCACTAACTTCA TT(SEQ ID NO: 532)
AS   3':    UU GUACUUUGGUGAUUGAAGU    (SEQ ID NO: 533)

S    5':       CAUGUUCCUUUAUUCACAA UU(SEQ ID NO: 534)
mRNA:       GT CATGTTCCTTTATTCACAA TC(SEQ ID NO: 535)
AS   3':    UU GUACAAGGAAAUAAGUGUU    (SEQ ID NO: 536)

S    5':       GUUACCGGAUAACACUGAU UU(SEQ ID NO: 537)
mRNA:       CT GTTACCGGATAACACTGAT TA(SEQ ID NO: 538)
AS   3':    UU CAAUGGCCUAUUGUGACUA    (SEQ ID NO: 539)

S    5':       GCAUAGUACUUCAAAGCAA UU(SEQ ID NO: 540)
mRNA:       CA GCATAGTACTTCAAAGCAA GT(SEQ ID NO: 541)
AS   3':    UU CGUAUCAUGAAGUUUCGUU    (SEQ ID NO: 542)

S    5':       GACAUGGAAUUGGAUGACU UU(SEQ ID NO: 543)
mRNA:       TC GACATGGAATTGGATGACT TG(SEQ ID NO: 544)
AS   3':    UU CUGUACCUUAACCUACUGA    (SEQ ID NO: 545)

S    5':       GAAGAAUACUGUAUUGUGU UU(SEQ ID NO: 546)
mRNA:       TA GAAGAATACTGTATTGTGT GT(SEQ ID NO: 547)
AS   3':    UU CUUCUUAUGACAUAACACA    (SEQ ID NO: 548)

S    5':       GCUUUAGUCACUAAUUGCU UU(SEQ ID NO: 549)
mRNA:       TT GCTTTAGTCACTAATTGCT TT(SEQ ID NO: 550)
AS   3':    UU CGAAAUCAGUGAUUAACGA    (SEQ ID NO: 551)

S    5':       CACUCGACAUUUGGUGAGA UU(SEQ ID NO: 552)
mRNA:       TT CACTCGACATTTGGTGAGA GA(SEQ ID NO: 553)
AS   3':    UU GUGAGCUGUAAACCACUCU    (SEQ ID NO: 554)

S    5':       GGAUUUACAUAAGAUGAGU UU(SEQ ID NO: 555)
mRNA:       TT GGATTTACATAAGATGAGT TA(SEQ ID NO: 556)
AS   3':    UU CCUAAAUGUAUUCUACUCA    (SEQ ID NO: 557)

S    5':       GAAGUCAUAAAGAUAGGAU UU(SEQ ID NO: 558)
mRNA:       AA GAAGTCATAAAGATAGGAT TT(SEQ ID NO: 559)
AS   3':    UU CUUCAGUAUUUCUAUCCUA    (SEQ ID NO: 560)

S    5':       GGAUAACACUGAUUAGUCA UU(SEQ ID NO: 561)
mRNA:       CC GGATAACACTGATTAGTCA GT(SEQ ID NO: 562)
AS   3':    UU CCUAUUGUGACUAAUCAGU    (SEQ ID NO: 563)

S    5':       GUGUUGCUUUCCUCUGGAU UU(SEQ ID NO: 564)
mRNA:       CA GTGTTGCTTTCCTCTGGAT CA(SEQ ID NO: 565)
AS   3':    UU CACAACGAAAGGAGACCUA    (SEQ ID NO: 566)

S    5':       CUAGAUUCCAGCCAGGAUA UU(SEQ ID NO: 567)
mRNA:       TG CTAGATTCCAGCCAGGATA CA(SEQ ID NO: 568)
AS   3':    UU GAUCUAAGGUCGGUCCUAU    (SEQ ID NO: 569)

S    5':       GUGAAUAUGUGGUUUCUCU UU(SEQ ID NO: 570)
mRNA:       CA GTGAATATGTGGTTTCTCT TA(SEQ ID NO: 571)
AS   3':    UU CACUUAUACACCAAAGAGA    (SEQ ID NO: 572)

S    5':       GACAGAAUAUGUGGCCACA UU(SEQ ID NO: 573)
mRNA:       CT GACAGAATATGTGGCCACA CG(SEQ ID NO: 574)
AS   3':    UU CUGUCUUAUACACCGGUGU    (SEQ ID NO: 575)
```

```
S 5':       GAGAAGUACAAAGGUUGCA UU(SEQ ID NO: 576)
mRNA:    GA GAGAAGTACAAAGGTTGCA GT(SEQ ID NO: 577)
AS 3':   UU CUCUUCAUGUUUCCAACGU    (SEQ ID NO: 578)

S 5':       CAGAUCCAGACCAUGAUCA UU(SEQ ID NO: 579)
mRNA:    TG CAGATCCAGACCATGATCA CA(SEQ ID NO: 580)
AS 3':   UU GUCUAGGUCUGGUACUAGU    (SEQ ID NO: 581)

S 5':       CACGUAAUAUUUCAGCCAU UU(SEQ ID NO: 582)
mRNA:    GC CACGTAATATTTCAGCCAT TC(SEQ ID NO: 583)
AS 3':   UU GUGCAUUAUAAAGUCGGUA    (SEQ ID NO: 584)

S 5':       GUGAUCUCAAGAUCUGUGA UU(SEQ ID NO: 585)
mRNA:    CT GTGATCTCAAGATCTGTGA CT(SEQ ID NO: 586)
AS 3':   UU CACUAGAGUUCUAGACACU    (SEQ ID NO: 587)

S 5':       CACACUCAUUCCUUCUGCU UU(SEQ ID NO: 588)
mRNA:    TG CACACTCATTCCTTCTGCT CT(SEQ ID NO: 589)
AS 3':   UU GUGUGAGUAAGGAAGACGA    (SEQ ID NO: 590)

S 5':       CAAAGCAAGUACUCAGUAA UU(SEQ ID NO: 591)
mRNA:    TT CAAAGCAAGTACTCAGTAA AT(SEQ ID NO: 592)
AS 3':   UU GUUUCGUUCAUGAGUCAUU    (SEQ ID NO: 593)

S 5':       CAUCUUUCCAGGGAAGCAU UU(SEQ ID NO: 594)
mRNA:    CC CATCTTTCCAGGGAAGCAT TA(SEQ ID NO: 595)
AS 3':   UU GUAGAAAGGUCCCUUCGUA    (SEQ ID NO: 596)

S 5':       GAACACAGAAAUGCUCACA UU(SEQ ID NO: 597)
mRNA:    CT GAACACAGAAATGCTCACA GG(SEQ ID NO: 598)
AS 3':   UU CUUGUGUCUUUACGAGUGU    (SEQ ID NO: 599)

S 5':       CUACUAACAUCUGGAGACU UU(SEQ ID NO: 600)
mRNA:    GG CTACTAACATCTGGAGACT GT(SEQ ID NO: 601)
AS 3':   UU GAUGAUUGUAGACCUCUGA    (SEQ ID NO: 602)

S 5':       GUUCAAAUAAGCUUUCAGA UU(SEQ ID NO: 603)
mRNA:    AT GTTCAAATAAGCTTTCAGA CT(SEQ ID NO: 604)
AS 3':   UU CAAGUUUAUUCGAAAGUCU    (SEQ ID NO: 605)

S 5':       GCAAUGACCAUAUCUGCUA UU(SEQ ID NO: 606)
mRNA:    CA GCAATGACCATATCTGCTA TT(SEQ ID NO: 607)
AS 3':   UU CGUUACUGGUAUAGACGAU    (SEQ ID NO: 608)

S 5':       CUUUCUAACAGGCCCAUCU UU(SEQ ID NO: 609)
mRNA:    TG CTTTCTAACAGGCCCATCT TT(SEQ ID NO: 610)
AS 3':   UU GAAAGAUUGUCCGGGUAGA    (SEQ ID NO: 611)

S 5':       GAUUCAGUGUUGCUUUCCU UU(SEQ ID NO: 612)
mRNA:    AA GATTCAGTGTTGCTTTCCT CT(SEQ ID NO: 613)
AS 3':   UU CUAAGUCACAACGAAAGGA    (SEQ ID NO: 614)

S 5':       GGAAGCAUUAUCUUGACCA UU(SEQ ID NO: 615)
mRNA:    AG GGAAGCATTATCTTGACCA GC(SEQ ID NO: 616)
AS 3':   UU CCUUCGUAAUAGAACUGGU    (SEQ ID NO: 617)

S 5':       GUACAAAGGUUGCAGUGCU UU(SEQ ID NO: 618)
mRNA:    AA GTACAAAGGTTGCAGTGCT GA(SEQ ID NO: 619)
AS 3':   UU CAUGUUUCCAACGUCACGA    (SEQ ID NO: 620)

S 5':       CAGUAUGUUAAUACACACA UU(SEQ ID NO: 621)
mRNA:    AA CAGTATGTTAATACACACA TA(SEQ ID NO: 622)
AS 3':   UU GUCAUACAAUUAUGUGUGU    (SEQ ID NO: 623)

S 5':       GAAUGGUCCUAACCAAGGU UU(SEQ ID NO: 624)
mRNA:    GA GAATGGTCCTAACCAAGGT AC(SEQ ID NO: 625)
AS 3':   UU CUUACCAGGAUUGGUUCCA    (SEQ ID NO: 626)

S 5':       CCAUUGAUAUUUGGUCUGU UU(SEQ ID NO: 627)
mRNA:    GT CCATTGATATTTGGTCTGT AG(SEQ ID NO: 628)
AS 3':   UU GGUAACUAUAAACCAGACA    (SEQ ID NO: 629)

S 5':       CCAAUGGCUCUAGUCACU UU(SEQ ID NO: 630)
mRNA:    CC CCAATTGGCTCTAGTCACT GG(SEQ ID NO: 631)
AS 3':   UU GGUUAACCGAGAUCAGUGA    (SEQ ID NO: 632)

S 5':       CCACGUAAUAUUUCAGCCA UU(SEQ ID NO: 633)
mRNA:    TG CCACGTAATATTTCAGCCA TT(SEQ ID NO: 634)
AS 3':   UU GGUGCAUUAUAAAGUCGGU    (SEQ ID NO: 635)

S 5':       CUUACGUCAUCCACCUUGA UU(SEQ ID NO: 636)
mRNA:    CT CTTACGTCATCCACCTTGA CA(SEQ ID NO: 637)
AS 3':   UU GAAUGCAGUAGGUGGAACU    (SEQ ID NO: 638)

S 5':       CAUGAGAACAUCAUUGGAA UU(SEQ ID NO: 639)
mRNA:    GA CATGAGAACATCATTGGAA TC(SEQ ID NO: 640)
AS 3':   UU GUACUCUUGUAGUAACCUU    (SEQ ID NO: 641)

S 5':       CUGUUCCCAAAUGCUGACU UU(SEQ ID NO: 642)
mRNA:    GG CTGTTCCCAAATGCTGACT CC(SEQ ID NO: 643)
AS 3':   UU GACAAGGGUUUACGACUGA    (SEQ ID NO: 644)

S 5':       CAACAAAGUUCGAGUAGCU UU(SEQ ID NO: 645)
mRNA:    GT CAACAAAGTTCGAGTAGCT AT(SEQ ID NO: 646)
AS 3':   UU GUUGUUUCAAGCUCAUCGA    (SEQ ID NO: 647)

S 5':       GAAGCAAUAUUACUUGCCU UU(SEQ ID NO: 648)
mRNA:    TG GAAGCAATATTACTTGCCT TG(SEQ ID NO: 649)
AS 3':   UU CUUCGUUAUAAUGAACGGA    (SEQ ID NO: 650)

S 5':       GUUCUUCAGACCUUCACCU UU(SEQ ID NO: 651)
mRNA:    TG GTTCTTCAGACCTTCACCT GT(SEQ ID NO: 652)
AS 3':   UU CAAGAAGUCUGGAAGUGGA    (SEQ ID NO: 653)

S 5':       CUCACUUUAUGAUAGGGAA UU(SEQ ID NO: 654)
mRNA:    AT CTCACTTTATGATAGGGAA GG(SEQ ID NO: 655)
AS 3':   UU GAGUGAAAUACUAUCCCUU    (SEQ ID NO: 656)

S 5':       GUUUGGAGCUCUAUCCAUA UU(SEQ ID NO: 657)
mRNA:    GT GTTTGGAGCTCTATCCATA TT(SEQ ID NO: 658)
AS 3':   UU CAAACCUCGAGAUAGGUAU    (SEQ ID NO: 659)

S 5':       CAGUAGCUUUGAGAAGCUA UU(SEQ ID NO: 660)
mRNA:    AC CAGTAGCTTTGAGAAGCTA CA(SEQ ID NO: 661)
AS 3':   UU GUCAUCGAAACUCUUCGAU    (SEQ ID NO: 662)

S 5':       GAAGUACAAAGGUUGCAGU UU(SEQ ID NO: 663)
mRNA:    GA GAAGTACAAAGGTTGCAGT GC(SEQ ID NO: 664)
AS 3':   UU CUUCAUGUUUCCAACGUCA    (SEQ ID NO: 665)

S 5':       CUUCCAGAUUUGCUCUGCA UU(SEQ ID NO: 666)
mRNA:    GT CTTCCAGATTTGCTCTGCA TG(SEQ ID NO: 667)
AS 3':   UU GAAGGUCUAAACGAGACGU    (SEQ ID NO: 668)

S 5':       CAAUAUUACUUGCCUUGUA UU(SEQ ID NO: 669)
mRNA:    AG CAATATTACTTGCCTTGTA TA(SEQ ID NO: 670)
AS 3':   UU GUUAUAAUGAACGGAACAU    (SEQ ID NO: 671)

S 5':       GAAAGAUGCAGUGGUUCCU UU(SEQ ID NO: 672)
mRNA:    TT GAAAGATGCAGTGGTTCCT CC(SEQ ID NO: 673)
AS 3':   UU CUUUCUACGUCACCAAGGA    (SEQ ID NO: 674)

S 5':       CAAUGACCAUAUCUGCUAU UU(SEQ ID NO: 675)
mRNA:    AG CAATGACCATATCTGCTAT TT(SEQ ID NO: 676)
AS 3':   UU GUUACUGGUAUAGACGAUA    (SEQ ID NO: 677)

S 5':       GAAAUACCUUGGCUGAUGU UU(SEQ ID NO: 678)
mRNA:    TG GAAATACCTTGGCTGATGT TG(SEQ ID NO: 679)
AS 3':   UU CUUUAUGGAACCGACUACA    (SEQ ID NO: 680)

S 5':       CUUGACAUGAUGGGUCAGA UU(SEQ ID NO: 681)
mRNA:    AC CTTGACATGATGGGTCAGA AA(SEQ ID NO: 682)
AS 3':   UU GAACUGUACUACCCAGUCU    (SEQ ID NO: 683)

S 5':       CUAGAAUCAUUGUAGCCAU UU(SEQ ID NO: 684)
mRNA:    TT CTAGAATCATTGTAGCCAT AA(SEQ ID NO: 685)
AS 3':   UU GAUCUUAGUAACAUCGGUA    (SEQ ID NO: 686)

S 5':       GUAACCAGUAGCUUUGAGA UU(SEQ ID NO: 687)
mRNA:    AG GTAACCAGTAGCTTTGAGA AG(SEQ ID NO: 688)
AS 3':   UU CAUUGGUCAUCGAAACUCU    (SEQ ID NO: 689)

S 5':       CUACUUCAAAUGUGGGUGU UU(SEQ ID NO: 690)
mRNA:    AG CTACTTCAAATGTGGGTGT TT(SEQ ID NO: 691)
AS 3':   UU GAUGAAGUUUACACCCACA    (SEQ ID NO: 692)

S 5':       CAUUGAUAUUUGGUCUGUA UU(SEQ ID NO: 693)
mRNA:    TC CATTGATATTTGGTCTGTA GG(SEQ ID NO: 694)
AS 3':   UU GUAACUAUAAACCAGACAU    (SEQ ID NO: 695)
```

```
S 5':      GUUUCUCUUACGUCAUCCA UU(SEQ ID NO: 696)
mRNA:   TG GTTTCTCTTACGTCATCCA CC(SEQ ID NO: 697)
AS 3':  UU CAAAGAGAAUGCAGUAGGU    (SEQ ID NO: 698)

S 5':      GUGUUAUGGAAAGAGCACA UU(SEQ ID NO: 699)
mRNA:   TG GTGTTATGGAAAGAGCACA GG(SEQ ID NO: 700)
AS 3':  UU CACAAUACCUUUCUCGUGU    (SEQ ID NO: 701)

S 5':      GGUUAUAUAAAGACUGCCU UU(SEQ ID NO: 702)
mRNA:   TG GGTTATATAAAGACTGCCT GC(SEQ ID NO: 703)
AS 3':  UU CCAAUAUAUUUCUGACGGA    (SEQ ID NO: 704)

S 5':      GGAAUUGGAUGACUUGCCU UU(SEQ ID NO: 705)
mRNA:   AT GGAATTGGATGACTTGCCT AA(SEQ ID NO: 706)
AS 3':  UU CCUUAACCUACUGAACGGA    (SEQ ID NO: 707)

S 5':      CAUUCAAGUUCGACAUGGA UU(SEQ ID NO: 708)
mRNA:   AC CATTCAAGTTCGACATGGA AT(SEQ ID NO: 709)
AS 3':  UU GUAAGUUCAAGCUGUACCU    (SEQ ID NO: 710)

S 5':      GUUUGAAAGAUGCAGUGGU UU(SEQ ID NO: 711)
mRNA:   TG GTTTGAAAGATGCAGTGGT TC(SEQ ID NO: 712)
AS 3':  UU CAAACUUUCUACGUCACCA    (SEQ ID NO: 713)

S 5':      GAAUGUUUAUGGCACCUGA UU(SEQ ID NO: 714)
mRNA:   TT GAATGTTTATGGCACCTGA CT(SEQ ID NO: 715)
AS 3':  UU CUUACAAAUACCGUGGACU    (SEQ ID NO: 716)

S 5':      CAAAUAAGCUUUCAGACUA UU(SEQ ID NO: 717)
mRNA:   TT CAAATAAGCTTTCAGACTA AT(SEQ ID NO: 718)
AS 3':  UU GUUUAUUCGAAAGUCUGAU    (SEQ ID NO: 719)

S 5':      CUAAUCAUGAGGACUCUGU UU(SEQ ID NO: 720)
mRNA:   AA CTAATCATGAGGACTCTGT CC(SEQ ID NO: 721)
AS 3':  UU GAUUAGUACUCCUGAGACA    (SEQ ID NO: 722)

S 5':      GGUAACUUGUGUUAGGGCU UU(SEQ ID NO: 723)
mRNA:   GT GGTAACTTGTGTTAGGGCT GT(SEQ ID NO: 724)
AS 3':  UU CCAUUGAACACAAUCCCGA    (SEQ ID NO: 725)

S 5':      CAUUUCAACUGUUCAGCAU UU(SEQ ID NO: 726)
mRNA:   TA CATTTCAACTGTTCAGCAT AG(SEQ ID NO: 727)
AS 3':  UU GUAAAGUUGACAAGUCGUA    (SEQ ID NO: 728)

S 5':      GAUUGAAGUAGAACAGGCU UU(SEQ ID NO: 729)
mRNA:   AG GATTGAAGTAGAACAGGCT CT(SEQ ID NO: 730)
AS 3':  UU CUAACUUCAUCUUGUCCGA    (SEQ ID NO: 731)

S 5':      CUAUUUGCUUUCUCUUCCA UU(SEQ ID NO: 732)
mRNA:   AA CTATTTGCTTTCTCTTCCA CA(SEQ ID NO: 733)
AS 3':  UU GAUAAACGAAAGAGAAGGU    (SEQ ID NO: 734)

S 5':      CUGACAGAAUAUGUGGCCA UU(SEQ ID NO: 735)
mRNA:   TC CTGACAGAATATGTGGCCA CA(SEQ ID NO: 736)
AS 3':  UU GACUGUCUUAUACACCGGU    (SEQ ID NO: 737)

S 5':      GAUUUGCUCUGCAUGUGGU UU(SEQ ID NO: 738)
mRNA:   CA GATTTGCTCTGCATGTGGT AA(SEQ ID NO: 739)
AS 3':  UU CUAAACGAGACGUACACCA    (SEQ ID NO: 740)

S 5':      GUUUCUGGUAGUUGUGGCU UU(SEQ ID NO: 741)
mRNA:   CG GTTTCTGGTAGTTGTGGCT TT(SEQ ID NO: 742)
AS 3':  UU CAAAGACCAUCAACACCGA    (SEQ ID NO: 743)

S 5':      GAAAUCCAGAGCAAGUCCU UU(SEQ ID NO: 744)
mRNA:   TG GAAATCCAGAGCAAGTCCT CC(SEQ ID NO: 745)
AS 3':  UU CUUUAGGUCUCGUUCAGGA    (SEQ ID NO: 746)

S 5':      GAUAUUUGGUCUGUAGGCU UU(SEQ ID NO: 747)
mRNA:   TT GATATTTGGTCTGTAGGCT GC(SEQ ID NO: 748)
AS 3':  UU CUAUAAACCAGACAUCCGA    (SEQ ID NO: 749)

S 5':      CAAUGACAUUAUUCGAGCA UU(SEQ ID NO: 750)
mRNA:   AT CAATGACATTATTCGAGCA CC(SEQ ID NO: 751)
AS 3':  UU GUUACUGUAAUAAGCUCGU    (SEQ ID NO: 752)

S 5':      CUUAUCCACUUUGACUCCU UU(SEQ ID NO: 753)
mRNA:   GG CTTATCCACTTTGACTCCT TT(SEQ ID NO: 754)
AS 3':  UU GAAUAGGUGAAACUGAGGA    (SEQ ID NO: 755)

S 5':      CAUAAUGUAACUGGGCAGA UU(SEQ ID NO: 756)
mRNA:   AA CATAATGTAACTGGGCAGA GA(SEQ ID NO: 757)
AS 3':  UU GUAUUACAUUGACCCGUCU    (SEQ ID NO: 758)

S 5':      CAAAUGGAAAUCCAGAGCA UU(SEQ ID NO: 759)
mRNA:   AA CAAATGGAAATCCAGAGCA AG(SEQ ID NO: 760)
AS 3':  UU GUUUACCUUUAGGUCUCGU    (SEQ ID NO: 761)

S 5':      CUUUAUGAUAGGGAAGGCU UU(SEQ ID NO: 762)
mRNA:   CA CTTTATGATAGGGAAGGCT AC(SEQ ID NO: 763)
AS 3':  UU GAAAUACUAUCCCUUCCGA    (SEQ ID NO: 764)
```

The inhibitory nucleic acids used in the compositions and methods described herein can have any of the SEQ ID NO:3-162, 166-764 sequences, or any combination thereof. Moreover, the inhibitory nucleic acids used in the compositions and methods described herein can be complementary to any of the SEQ ID NO:3-162, 166-764 sequences, or any combination thereof. In some embodiments, the inhibitory nucleic acids used in the compositions and methods described herein include one or more of the SEQ ID NO:3-162, 166-764 sequences with one or more sequences that are complementary to any of SEQ ID NO:3-162, 166-764. For example, the inhibitory nucleic acids used in the compositions and methods described herein can include both a sense sequence selected from any of SEQ ID NO:3-162, 166-764 and the corresponding antisense sequence selected from any of SEQ ID NO:3-162, 166-764. Combinations of such nucleic acid inhibitors can also be employed in the methods and compositions described herein.

As described in more detail below the siRNAs can be expressed from an expression cassette and/or expression vector. Such an expression cassette or expression vector includes, among other things, a sequence contiguously encoding the sense and antisense siRNA sequences.

Thus, for example, when using an siRNA with the sense strand GGAACAGGTTGTTCCCAAA (SEQ ID NO:765), an expression cassette can be used that includes the SEQ ID NO:765 sequence linked to a spacer derived from an miRNA (e.g., TTCAAGAGA; SEQ ID NO:766) at the 3' end linked to the corresponding antisense sequence (TTTGGGAACAACCTGTTCC (SEQ ID NO:767)). Thus, the non-template strand sequence used in the expression cassette for the GGAACAGGTTGTTCCCAAA (SEQ ID NO:765) siRNA will have the following sequence (SEQ ID NO:768)): GGAACAGGTTGTTCCCAAA-TTCAAGAGA-TTTGGGAACAACCTGTTCC.

This sequence should be placed downstream of an RNA polymerase (RNA pol) promoter in the vector.

In some of the experiments described herein an RNA pol III promoter was used. It is known that consecutive dA residues in the template strand are required to stop transcription by RNA pol III (dTs in the non-template strand). Therefore, the vector contains six consecutive dTs in the non-template strand following the shRNA cassette. If the shRNA cassette is driven by an RNA pol II promoter, other strategies could be used to stop the transcription. Expression cassettes and/or expression vectors encoding shRNAs for all the siRNAs identified herein can be made by similar procedures.

A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave an ERK2 mRNA transcript and thereby inhibit translation of the mRNA. See, for example, Haseloff et al., U.S. Pat. No. 5,641,673.

Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a specific nucleotide sequence. Longer complementary sequences may be used to increase the affinity of the hybridization sequence for the target.

The hybridizing and cleavage regions of the ribozyme can be integrally related; thus, upon hybridizing to the target RNA through the complementary regions, the catalytic region of the ribozyme can cleave the target. Thus, an existing ribozyme may be modified to target an ERK2 nucleic acid of the invention by modifying the hybridization region of the ribozyme to include a sequence that is complementary to the target ERK2 nucleic acid. Alternatively, an mRNA encoding a ERK2 may be used to select a catalytic RNA having a specific ribonuclease activity from a pool of RNA molecules. See, for example, Bartel & Szostak, Science 261:1411-1418 (1993).

The inhibitory nucleic acids of the invention may include modified nucleotides, as well as natural nucleotides such as combinations of ribose and deoxyribose nucleotides, and an antisense inhibitory nucleic acid of the invention may be of any length discussed above and that is complementary to an ERK2 mRNA.

For example the inhibitory nucleic acids can include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Other modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other inhibitory nucleic acids can have modifications in both the sugar and the internucleoside linkage, for example, where the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Inhibitory nucleic acid agents used in the compositions and methods described herein may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2.degree. C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

In some embodiments, expression cassettes are employed to facilitate delivery of nucleic acids that inhibit the expression of ERK2. Expression cassettes can be of any suitable construction, and can be included in any appropriate delivery vector. Such delivery vectors include plasmid DNA, viral DNA, and the like. The means by which the expression cassette in its delivery or expression vector is introduced into target cells or target organism can be transfection, reverse transfection, virus induced transfection, electroporation, direct introduction by biolystics (e.g., using a "gene gun;" BioRad, Inc., Emeryville, Calif.), and the like. Other methods that can be employed include methods widely known in the art as the methods of gene therapy. Once delivered into a target cell, or target organism the expression cassette may be maintained on an autonomously replicating piece of DNA (e.g., an expression vector), or may be integrated into the genome of the target cell or target organism.

Typically, to assemble the expression cassettes and vectors of the present invention a nucleic acid, preferably a DNA, encoding an siRNA is incorporated into a unique restriction endonuclease cleavage site, or a multiple cloning site, within a pre-existing "empty" expression cassette to form a complete recombinant expression cassette that is capable of directing the production of the siRNA transcripts of the present invention. Frequently such complete recombinant expression cassettes reside within, or inserted into, expression vectors designed for the expression of such siRNA transcripts. Methods for the construction of an expression vector for purposes of this invention should be apparent to skilled artisans apprised of the present invention. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast Saccharomyces, Eds. Strathern et al., Cold Spring Harbor Press, Vols. I and II, 1982; and Sambrook et al., Molecular Cloning: A Laboratory Manual, Cold Spring Harbor Press, 1989.)

Generally, the expression cassettes inserted or assembled within the expression vectors have a promoter operably linked to a DNA encoding the siRNA that is to be employed. The promoter can be a native promoter, i.e., a promoter that is responsible for the expression of that particular gene product in cells, or it can be any other suitable promoter. Alternatively, the expression cassette can be a chimera, i.e., having a heterologous promoter that is not the native promoter responsible for the expression of the siRNA. Such heterologous promoters can even be from a different species than the target cell or organism.

The expression vector may further include an origin of DNA replication for the replication of the vectors in target cells. Preferably, the expression vectors also include a replication origin for the amplification of the vectors in, e.g., *E. coli*, and selection marker(s) for selecting and maintaining only those target cells harboring the expression vectors. Additionally, in some embodiments the expression vectors also contain inducible or derepressible promoters, which function to control the transcription of the siRNA transcript from the DNA that encodes it. Other regulatory sequences such as transcriptional enhancer sequences and translation regulation sequences (e.g., Shine-Dalgarno sequence) can also be operably included in the expression vectors. Transcription termination sequences, and polyadenylation signal sequences, such as those from bovine growth hormone, SV40, lacZ and AcMNPV polyhedral protein genes, may also be present.

The expression vectors of the present invention can be introduced into the target cells by any techniques known in the art, e.g., by direct DNA transformation, microinjection, electroporation, viral infection, lipofection, biolystics, and the like. The expression of the siRNA can be transient or stable, inducible or derepressible. The expression vectors can be maintained in target cells in an extrachromosomal state, i.e., as self-replicating plasmids or viruses. Alternatively, the expression vectors, or portions thereof, can be integrated into chromosomes of the target cells by conventional techniques such as site-specific recombination or selection of stable cell lines. In stable cell lines, at least the expression cassette portion of the expression vector is integrated into a chromosome of the target cells.

The vector construct can be designed to be suitable for expression in various target cells, including but not limited to bacteria, yeast cells, plant cells, nematode cells, insect cells, and mammalian and human cells. Methods for preparing expression vectors designed for expression of gene products in different target cells are well known in the art.

In some embodiments, the vector is a neurotropic adeno-associated viral vector. For example, the vector can be a neurotropic recombinant adeno-associated virus (rAAV). Adeno-associated viruses (AAV) have a linear single-stranded DNA (ssDNA) genome of approximately 4.7-kilobases (kb), with two 145 nucleotide-long inverted terminal repeats (ITR) at the termini. The virus does not encode a polymerase and therefore relies on cellular polymerases for genome replication. The ITRs flank the two viral genes—rep (replication) and cap (capsid), encoding non-structural and structural proteins, respectively.

One type of AAV vector that can be used to facilitate delivery of siRNAs into neurons and/or the brain or spinal cord is a serotype-2 rAAV vector (Musatov et al., 2002). This vector is available from Vector Biolabs (Philadelphia, Pa.). The rAAV vector-based siRNA approach presents a potent and facile tool to produce a spatial and temporal knockdown of the expression of a gene of interest (Garraway et al., 2007). Several factors indicate that the choice of a rAAV vector for the delivery of the ERK2 siRNA is a good one. First, the serotype-2 rAAV vector selectively transduces neurons in vivo (Kaspar et al., 2002). Second, rAAV is able to mediate long-term siRNA expression and gene knockdown in the transduced cells. As shown in the Examples, GFP and ERK expression was examined for 6 weeks, however, previous studies by the inventors have demonstrated that a single administration of a rAAV vector resulted in the knockdown of NR1 gene expression that persisted for at least 6 months (Garraway et al., 2007). Third, rAAV is safe and therefore convenient to use in behavioral experiments requiring repeated measurements. Fourth, rAAV mediated gene knockdown can be controlled both temporally and spatially. This conditional approach avoids embryonic lethality associated with a constitutive knock-out of ERK2 (Hatano et al., 2003; Saba-El-Leil et al., 2003; Yao et al., 2003).

Consistent with the observations described herein, several reports (Kaspar et al., 2002; South et al., 2003; Garraway et al., 2007) have provided evidence at the ultrastructural and light microscope levels as well as direct behavioral threshold evidence that the injection of AAV into the brain or spinal cord dorsal horn does not result in significant immune or glial activation or behavioral sensitization. It has been suggested that a high dose of a siRNA might induce nonspecific and off-target effects (Bridge et al., 2003; Sledz et al., 2003). However, previous studies by the inventors indicated that neither an NR1 siRNA nor a control siRNA delivered by the rAAV vector induced detectable cellular toxicity (Garraway et al., 2007). Transduced neurons exhibited unaltered expression of NeuN compared with the contralateral side. In addition, no signs of gliosis or neuronal damage were observed in experiments described herein (FIG. 2G).

Moreover, the specificity of the rAAV vectors employed herein not only for neuronal tissues but also for ERK2 is clearly demonstrated in the Examples. The vectors expressed different siRNAs but induced a similar degree of marker GFP expression and knockdown of the ERK2 mRNA in the spinal cord dorsal horn. Thus, this knockdown is specific to the targeted tissues. Moreover, the knockdown by the siRNAs described herein (Examples 1-3) clearly targets the ERK2mRNA and protein as revealed by in situ hybridization and Western blot. However, the closely related ERK1 was unaffected at the protein level. Thus, the utility of the siRNAs for specifically reducing ERK2 expression in neuronal tissues is demonstrated.

ERK2 Compound Inhibitors

In some embodiments, the ERK2 inhibitor is a compound or small molecule. Such compounds are readily available, for example, are described in U.S. Pat. Nos. 7,345,054, 7,304, 061, 7,253,187 and 6,743,791, which are specifically incorporated herein by reference in their entireties.

Compounds that can be used in the compositions and methods described herein include, for example, compounds of formula I:

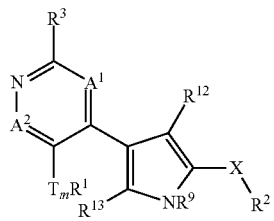

or a pharmaceutically acceptable salt thereof, wherein:

$A^1$ is N or $CR^{10}$;
$A^2$ is N or $CR^{11}$;
T is selected from —C($R^7$)$_2$—, C(O)—, —C(O)C(O)—, —C(O)N$R^7$—, —C(O)N$R^7$N$R^7$—, —CO$_2$—, —OC(O)—, —N$R^7$CO$_2$—, —N$R^7$C(O)N$R^7$—, OC(O)N$R^7$—, —N$R^7$N$R^7$—, —N$R^7$C(O)—, —SO$_2$—N$R^7$—, —SO$_2$N$R^7$—, —N$R^7$SO$_2$—, —N$R^7$O$_2$—, or —N$R^7$SO$_2$N$R^7$—;
m is selected from zero or one;
$R^1$ is selected from: (a) hydrogen, CN, halogen, R, N($R^7$)$_2$, OR, or OH, wherein m is zero; or (b) hydrogen or R, wherein m is one;
X is selected from —C(O)—, —C(O)N$R^7$—, —N$R^7$C(O)—, —N$R^7$SO$_2$—, —SO$_2$N$R^7$—, —S(O)—, or —SO$_2$—;
$R^2$ is selected from —(CH$_2$)$_y$R$^5$, —(CH$_2$)$_y$CH(R$^5$)$_2$, —(CH$_2$)$_y$CH(R$^8$)(R$^5$), —(CH$_2$)$_y$CH(R$^8$)CH(R$^5$)$_2$, —N(R$^4$)$_2$, —NR$^4$(CH$_2$)$_y$N(R$^4$)$_2$, —ON(R$^7$)$_2$, or —NR$^7$OR$^6$;
y is 0-6;
$R^3$ is selected from —R, —OR$^6$, —SR$^6$, —S(O)R$^6$, —SO$_2$R$^6$, —ON(R$^7$)$_2$, —N(R)$_2$, —NRN(R$^7$)$_2$, or —NROR$^6$;
$R^6$ is selected from hydrogen or —R;
each R is independently selected from an optionally substituted group selected from $C_{1-6}$ aliphatic; 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen;

each $R^4$ is independently selected from —R, —R$^7$, —COR$^7$, —CO$_2$R, —CON(R$^7$)$_2$, —SO$_2$R$^7$, —(CH$_2$)$_y$R$^5$, or —(CH$_2$)$_y$CH(R$^5$)$_2$;
each $R^5$ is independently selected from —R, —OR, —CO$_2$R, —(CH$_2$)$_y$N(R)$_2$, —N(R$^7$)$_2$, —OR$^7$, —SR$^7$, —NR$^7$C(O)R$^7$, —NR$^7$CON(R$^7$)$_2$, —C(O)N(R$^7$)$_2$, —SO$_2$R$^7$, —NR$^7$SO$_2$R$^7$, —C(O)R$^7$, —CN, or —SO$_2$N(R$^7$)$_2$;
each $R^7$ is independently selected from hydrogen or an optionally substituted $C_{1-6}$ aliphatic group, or two R$^7$ groups bound to the same nitrogen are taken together with the nitrogen to form a 3-7 membered heterocyclic ring having 0-2 heteroatoms in addition to the nitrogen, independently selected from nitrogen, oxygen, or sulfur;
$R^8$ is selected from —R, —(CH$_2$)$_w$OR$^7$, —(CH$_2$)$_w$N(R$^4$)$_2$, or —(CH$_2$)$_w$SR$^7$;
each w is independently selected from 0-4;
$R^9$ is selected from hydrogen, a $C_{1-6}$ aliphatic group, C(O)R$^7$, C(O)OR$^7$, or SO$_2$R$^7$;
$R^{10}$ is selected from R$^7$, halogen, CN, NO$_2$, OR$^7$, SR$^7$, N(R$^7$)$_2$, C(O)R$^7$, or CO$_2$R$^7$; or R$^{10}$ and R$^3$ are taken together to form an optionally substituted 5-7 membered saturated, partially saturated, or aromatic ring having 0-2 heteroatoms independently selected from nitrogen, oxygen, and sulfur;
$R^{11}$ is selected from R$^7$, halogen, CN, NO$_2$, OR$^7$, SR$^7$, N(R$^7$)$_2$, C(O)R$^7$, or CO$_2$R$^7$;
$R^{12}$ is selected from R$^7$, CN, NO$_2$, halogen, N(R$^7$)$_2$, SR$^7$, and OR$^7$; and
$R^{13}$ is selected from R$^7$, CN, NO$_2$, halogen, N(R$^7$)$_2$, SR$^7$, and OR$^7$;
provided that only one of R$^{12}$ and R$^{13}$ is a 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy", "hydroxyalkyl," "alkoxyalkyl" and "alkoxycarbonyl," used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," haloalkenyl and "haloalkoxy" means alkyl, alkenyl or alkoxy, as the case may be, substituted with one or more halogen atoms. The term "halo" or "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR⁺ (as in N-substituted pyrrolidinyl).

The term "aryl" used alone or as part of a larger moiety as in "aralkyl," "aralkoxy" or "aryloxyalkyl," refers to monocyclic, bicyclic and tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring."

The term "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or as part of a larger moiety as in "heteroaralkyl" or "heteroarylalkoxy" refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic."

An aryl (including aralkyl, aralkoxy, aryloxyalkyl and the like) or heteroaryl (including heteroaralkyl, heteroarylalkoxy and the like) group may contain one or more substituents. Substituents on the unsaturated carbon atom of an aryl, heteroaryl, aralkyl, or heteroaralkyl group are selected from halogen; haloalkyl; —CF₃; —R°; —OR°; —SR°; 1,2-methylene-dioxy; 1,2-ethylenedioxy; dimethyleneoxy; protected OH (such as acyloxy); phenyl (Ph); Ph substituted with R.sup.o; —O(Ph); —O-(Ph) substituted with R°; —CH₂(Ph); —CH₂(Ph) substituted with R°; —CH₂CH₂(Ph); —CH₂CH₂(Ph) substituted with R°; —NO₂; —CN; —N(R°)₂; —NR°C(O)R°; —NR°C(O)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(O)N(R°)₂; —OC(O)N(R°)₂; —S(O)₂R°; —SO₂N(R°)₂; —S(O)R°; —NR°SO₂N(R°)₂; —NR°SO₂R°; —C(=S)N(R°)₂; —C(=NH)—N(R°)₂; —(CH₂)ᵧNHC(O)R°; —(CH₂)ᵧR°; —(CH₂)ᵧNHC(O)NHR°; —(CH₂)ᵧNHC(O)OR°; —(CH₂)ᵧNHS(O)R°; —(CH₂)ᵧNHSO₂R°; or —(CH₂)ᵧNHC(O)CH(V_z—R° (R°, wherein each R° is independently selected from hydrogen, optionally substituted C₁₋₆ aliphatic, an unsubstituted 5-6 membered heteroaryl or heterocyclic ring, phenyl (Ph), —O(Ph), or —CH₂(Ph)-CH₂(Ph), wherein y is 0-6; z is 0-1; and V is a linker group.

When R° is C₁₋₆ aliphatic, it is optionally substituted with one or more substituents selected from —NH₂, —NH(C₁₋₄ aliphatic), —N(C₁₋₄ aliphatic)₂, —S(O)(C₁₋₄ aliphatic), —SO₂(C₁₋₄ aliphatic), halogen, —(C₁₋₄ aliphatic), —OH, —O—(C₁₋₄ aliphatic), —NO₂, —CN, —CO₂H, —CO₂(C₁₋₄ aliphatic), —O(halo C₁₋₄ aliphatic), or -halo(C₁₋₄ aliphatic); wherein each C₁₋₄ aliphatic is unsubstituted.

An aliphatic group or a non-aromatic heterocyclic ring may contain one or more substituents. Substituents on the saturated carbon of an aliphatic group or of a non-aromatic heterocyclic ring are selected from those listed above for the unsaturated carbon of an aryl or heteroaryl group and the following: =O, =S, =NN(R*)₂, =NNHC(O)R*, =NNHCO₂(alkyl), =NNHSO₂(alkyl), or =NR*, where each R* is independently selected from hydrogen or an optionally substituted C₁₋₆ aliphatic. When R* is C₁₋₆ aliphatic, it is optionally substituted with one or more substituents selected from —NH₂, —NH(C₁₋₄ aliphatic), —N(C₁₋₄ aliphatic)₂, halogen, —OH, —O—(C₁₋₄ aliphatic), —NO₂, —CN, —CO₂H, —CO₂(C₁₋₄ aliphatic), —O(halo C₁₋₄ aliphatic), or —halo(C₁₋₄ aliphatic); wherein each C₁₋₄ aliphatic is unsubstituted.

Substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein each R⁺ is independently selected from hydrogen, an optionally substituted C₁₋₆ aliphatic, optionally substituted phenyl (Ph), optionally substituted —O(Ph), optionally substituted —CH₂(Ph), optionally substituted —CH₂CH₂(Ph), or an unsubstituted 5-6 membered heteroaryl or heterocyclic ring. When R⁺ is a C₁₋₆ aliphatic group or a phenyl ring, it is optionally substituted with one or more substituents selected from —NH₂, —NH(C₁₋₄ aliphatic), —N(C₁₋₄ aliphatic)₂, halogen, —(C₁₋₄ aliphatic), —OH, —O—(C₁₋₄ aliphatic), —NO₂, —CN, —CO₂H, —CO₂(C₁₋₄ aliphatic), —O(halo C₁₋₄ aliphatic), or -halo (C₁₋₄ aliphatic); wherein each C₁₋₄ aliphatic is unsubstituted.

The V linker group refers to an organic moiety that connects two parts of a compound. For example, V linkers are comprised of —O—, —S—, —NR*—, —C(O)—, or an alkylidene chain. The alkylidene chain is a saturated or unsaturated, straight or branched, C₁₋₆ carbon chain which is optionally substituted, and wherein up to two non-adjacent saturated carbons of the chain are optionally replaced by —C(O)—, —C(O)C(O)—, —C(O)NR*—, —C(O)NR*NR*—, —CO₂—, —OC(O)—, —NR*CO₂—, —O—, —NR*C(O)NR*—, —OC(O)NR*—, —NR*NR*—, —NR*C(O)—, —S—, —SO—, —SO₂—, —NR*—, —SO₂NR*—, or —NR*SO₂—; wherein R* is selected from hydrogen or C₁₋₄ aliphatic. Optional substituents on the alkylidene chain are as described above for an aliphatic group.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a ¹³C— or ¹⁴C— enriched carbon are within the scope of this invention.

Compounds of this invention may exist in alternative tautomeric forms. Unless otherwise indicated, the representation of either tautomer is meant to include the other.

Examples of useful ERK2 inhibitor compounds include the following:

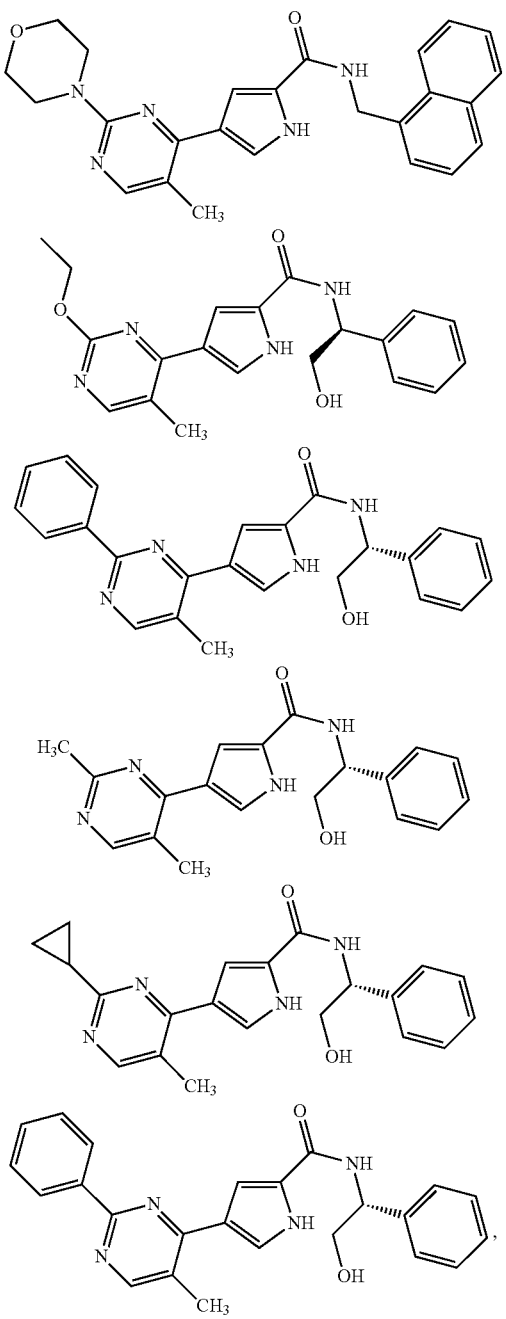

Antibodies

Another agent that can be used to inhibit ERK2 is an antibody preparation. Such anti-ERK2 antibodies can be used in the compositions and methods described herein. The term "antibody," as used herein, refers to a full-length immunoglobulin molecule or an immunologically-active fragment of an immunoglobulin molecule such as the Fab or F(ab')$_2$ fragment generated by, for example, cleavage of the antibody with an enzyme such as pepsin or co-expression of an antibody light chain and an antibody heavy chain in bacteria, yeast, insect cell or mammalian cell. The antibody can also be an IgG, IgD, IgA, IgE or IgM antibody.

As used herein, the term "binds specifically" or "specifically binds," in reference to an antibody/antigen interaction, means that the antibody binds with a particular antigen (e.g., ERK2) without substantially binding to other unrelated antigens. For example, in some embodiments, the anti-ERK2 antibodies bind with greater affinity to ERK2 than to ERK1. Thus, the anti-ERK2 antibodies can have at least 50% or greater affinity, or greater affinity, to ERK2 than to ERK1. In addition, the anti-ERK2 antibodies can have about 75% or greater affinity, and more preferably, about 90% or greater affinity, to ERK2 than to other unrelated polypeptides.

An antibody directed against ERK2 can be a polyclonal or monoclonal antibody. Polyclonal antibodies can be obtained by immunizing a mammal with a mutant polypeptide of the invention, and then isolating antibodies from the blood of the mammal using standard techniques. The antibodies can be evaluated for affinity to ERK2 using standard procedures including, for example, enzyme linked immunosorbent assay (ELISA) to determine antibody titer and protein A chromatography to obtain the antibody-containing an IgG fraction.

The anti-ERK2 antibodies can be monoclonal or polyclonal antibodies. A monoclonal antibody is a population of molecules having a common antigen binding site that binds specifically with a particular antigenic epitope. A monoclonal antibody can be obtained by selecting an antibody-producing cell from a mammal that has been immunized with ERK2, and fusing the antibody-producing cell, e.g. a B cell, with a myeloma to generate an antibody-producing hybridoma. A monoclonal antibody can also be obtained by screening a recombinant combinatorial library such as an ant—A LABORATORY MANUAL, Barbas, et al., eds. Cold Spring Harbor Laboratory Press, Cold Spring Harbor, ibody phage display library. See, for example, PHAGE DISPLAY N.Y., 2001; and Kontermann & Dübel, ANTIBODY ENGINEERING, Heidelberg: Springer-Verlag. Berlin, 2001.

An anti-ERK2 antibody can also be a murine, chimeric, humanized or fully human antibody. A murine antibody is an antibody derived entirely from a murine source, for example, an antibody derived from a murine hybridoma generated from the fusion of a mouse myeloma cell and a mouse B-lymphocyte cell. A chimeric antibody is an antibody that has variable regions derived from a non-human source, e.g. murine or primate, and constant regions derived from a human source. A humanized antibody has antigen-binding regions, e.g. complementarity-determining regions, derived from a mouse source, and the remaining variable regions and constant regions derived from a human source. A fully human antibody is antibody from human cells or derived from transgenic mice carrying human antibody genes.

Methods to generate antibodies are well known in the art. For example, a polyclonal antibody of the invention can be prepared by immunizing a suitable animal with ERK2. The animal can be, for example, a rabbit, goat, sheep, rabbit, hamster, chicken, cow, or mouse. At the appropriate time after immunization, antibody molecules can be isolated from the animal, e.g. from the blood or other fluid of the animal, and further purified using standard techniques that include, without limitation, precipitation using ammonium sulfate, gel filtration chromatography, ion exchange chromatography or affinity chromatography using protein A. In addition, an antibody-producing cell of the mammal can be isolated and used to prepare a hybridoma cell that secretes a monoclonal antibody of the invention. Techniques for preparing monoclonal antibody-secreting hybridoma cells are available in the art. See, for example, Kohler and Milstein, Nature 256:495-97 (1975) and Kozbor et al. Immunol Today 4: 72 (1983). A monoclonal antibody against ERK2 can also be prepared using other methods available in the art, such as, for example, expression from a recombinant DNA molecule, or screening of a recombinant combinatorial immunoglobulin library using a mutant polypeptide of the invention.

Methods to generate chimeric and humanized monoclonal antibodies are also readily available in the art and include, for example, methods involving recombinant DNA technology. A chimeric antibody can be produced by expression from a nucleic acid that encodes a non-human variable region and a human constant region of an antibody molecule. See, for example, Morrison et al., *Proc. Nat. Acad. Sci. U.S.A.* 86: 6851 (1984). A humanized antibody can be produced by expression from a nucleic acid that encodes non-human antigen-binding regions (complementarity-determining regions) and a human variable region (without antigen-binding regions) and human constant regions. See, for example, Jones et al., *Nature* 321:522-24 (1986); and Verhoeven et al., *Science* 239:1534-36 (1988). Completely human antibodies can be produced by immunizing engineered transgenic mice that express only human heavy and light chain genes. In this case, therapeutically useful monoclonal antibodies can then be obtained using conventional hybridoma technology. See, for example, Lonberg & Huszar, *Int. Rev. Immunol.* 13:65-93 (1995). Nucleic acids and techniques involved in design and production of antibodies are well known in the art. See, for example, Batra et al., *Hybridoma* 13:87-97 (1994); Berdoz et al., *PCR Methods Appl.* 4: 256-64 (1995); Boulianne et al. *Nature* 312:643-46 (1984); Carson et al., *Adv. Immunol.* 38:274-311 (1986); Chiang et al., *Biotechniques* 7:360-66 (1989); Cole et al., *Mol. Cell. Biochem.* 62:109-20 (1984); Jones et al., *Nature* 321: 522-25 (1986); Larrick et al., *Biochem Biophys. Res. Commun.* 160:1250-56 (1989); Morrison, *Annu. Rev. Immunol.* 10:239-65 (1992); Morrison et al., *Proc. Nat'l Acad. Sci. USA* 81: 6851-55 (1984); Orlandi et al., *Pro. Nat'l Acad. Sci. U.S.A.* 86:3833-37 (1989); Sandhu, *Crit. Rev. Biotechnol.* 12:437-62 (1992); Gavilondo & Larrick, *Biotechniques* 29: 128-32 (2000); Huston & George, *Hum. Antibodies.* 10:127-42 (2001); Kipriyanov & Le Gall, *Mol. Biotechnol.* 26: 39-60 (2004).

Another method for generating antibodies involves a Selected Lymphocyte Antibody Method (SLAM). The SLAM technology permits the generation, isolation and manipulation of monoclonal antibodies without needing to generate a hybridoma. The methodology principally involves the growth of antibody forming cells, the physical selection of specifically selected antibody forming cells, the isolation of the genes encoding the antibody and the subsequent cloning and expression of those genes.

The nucleic acids encoding the antibodies can be mutated to optimize the affinity, selectivity, binding strength or other desirable property of an antibody. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

The antibodies can be isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by at least one purification step.

If desired, the anti-ERK2 antibodies can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art are cognizant of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: METHODS IN MOLECULAR BIOLOGY, Vol. 10, pages 79-104 (Humana Press (1992).

In some embodiments, the antibody will be purified as measurable by at least three different methods: 1) to greater than 95% by weight of antibody as determined by the Lowry method, and preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomassie blue or, preferably, silver stain.

The antibodies described herein include immunologically-active fragments of antibodies. Methods of making antibody fragments are also known in the art (see for example, Harlow and Lane, ANTIBODIES: A LABORATORY MANUAL, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab monovalent fragments. Alternatively, an enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., *Science* 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991). The antibodies described herein can be any CDR-containing polypeptides.

Compositions

The invention also relates to compositions containing a nucleic acid that inhibits expression of ERK2 protein with SEQ ID NO:1 (or an expression cassette or vector that encodes such a nucleic acid), a compound that can inhibit ERK2 activity or an anti-ERK2 antibody can bind with specificity to a polypeptide having SEQ ID NO:1. The compositions can also contain a carrier, for example, a pharmaceutically acceptable carrier.

By "pharmaceutically acceptable" it is meant a carrier, diluent, excipient, and/or salt that is compatible with the other ingredients of the formulation, and not deleterious to the recipient thereof.

In some embodiments, the therapeutic agents of the invention (e.g., a nucleic acid that inhibits ERK2 expression, a vector encoding such a nucleic acid, a compound that inhibits ERK2 activity and/or an anti-ERK2 antibody), are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease that involves acute or chronic pain.

To achieve the desired effect(s), the nucleic acid that inhibits ERK2 expression, the vector encoding such a nucleic acid, the compound that inhibits ERK2 activity, the anti-ERK2 antibody and combinations thereof, may be administered as single or divided dosages. For example, nucleic acids, vectors, compounds and/or antibodies can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the nucleic acid, vector, compound or antibody chosen for administration, the disease, the weight, the physical condition, the health, the age of the mammal, and if the nucleic acid, vector, compound or antibody is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents and compositions of the invention may be essentially continuous over a preselected period of time or may be in a series of spaced doses. Both local and systemic administration is contemplated.

To prepare the composition, nucleic acids, vectors, compounds, antibodies and other agents are synthesized or otherwise obtained, purified as necessary or desired and then lyophilized and stabilized. These agents can then be adjusted to the appropriate concentration, and optionally combined with other agents. The absolute weight of a given nucleic acid, vector, compound, antibody and/or other agent included in a unit dose can vary widely. For example, about 0.01 to about 2 g, or about 0.1 to about 500 mg, of at least one nucleic acid, vector, compound or antibody of the invention, or a plurality or combination of nucleic acids, vectors, compounds and/or antibodies can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the therapeutic agents of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the nucleic acids, vectors, compounds and/or anti-ERK2 antibodies can be administered by a variety of routes including parenteral (including subcutaneous, intravenous, intramuscular and intraperitoneal), oral, rectal, dermal, transdermal, intrathoracic, intrapulmonary and intranasal (respiratory) routes. The nucleic acids, vectors, compounds and/or antibodies may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

The compositions of the invention may be prepared in many forms that include aqueous solutions, suspensions, tablets, hard or soft gelatin capsules, and liposomes and other slow-release formulations, such as shaped polymeric gels. However, administration of compounds, nucleic acids, vectors and/or antibodies often involves parenteral or local administration of the nucleic acids, vectors, compounds and/or antibodies in an aqueous solution or sustained release vehicle.

Thus while the nucleic acids, vectors, compounds and/or antibodies may sometimes be administered in an oral dosage form, that oral dosage form is typically formulated such that the protein, nucleic acid or antibody is released into the intestine after passing through the stomach. Such formulations are described in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives.

A protein, nucleic acid, compound or antibody can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Suitable carriers include saline solution and other materials commonly used in the art.

The compositions can also contain other ingredients such as other analgesics (e.g., acetaminophen, ibuprofen, salicylic acid), vitamins, anti-microbial agents, or preservatives. It will be appreciated that the amount of an nucleic acid, vector, compound or antibody required for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

The following non-limiting Examples illustrate certain aspects of the invention.

EXAMPLE 1

Materials and Methods

This Example illustrates some of the materials and methods used to determine that ERK2 inhibitors reduce pain in animals.

Experimental animals and drugs. Adult male C57BL/6 mice (Jackson Labs) weighing 20-30 grams were used for this study. Experiments were performed in accordance with National Institute of Health Guidelines for the Care and Use of Laboratory Animals. The experimental protocol (#0508-392A) was approved by the Institutional Animal Care and Use Committee at Weill Cornell Medical College. Animals were housed under 12 hour light/dark cycles in a pathogen-free room with free access to water and food.

Design and screening of siRNAs and viral vector production. The approaches used to design and screen for siRNAs targeting the expression of a single gene were described previously (Garraway et al., 2007). Candidate siRNAs were selected by the siRNA selection program from the Whitehead Institute for Biomedical Research (MIT) (Yuan et al., 2004). The sense and antisense sequence of the siRNA were joined by a spacer (TTCAAGAGA; SEQ ID NO:766) (Brummelkamp et al., 2002) to create a "stem-loop" sequence. Synthetic DNA oligomers with the corresponding sequences were ordered (Sigma-Genosys, St. Louis, Mo.), cloned into a serotype-2 recombinant adeno-associated virus (rAAV) plasmid and subject to the psiCHECK Dual Luciferase Reporter Assay (Promega, Madison, Wis.). Three plasmids expressing the most active siRNAs identified in the psiCHECK assay and one plasmid expressing a scrambled control siRNA were packaged into serotype-2 rAAV vectors (Musatov et al., 2002) and used in the in vivo studies.

The three active sequences (sense strand) identified by the psiCHECK assay were

ERK2-5,5'-GGAACAGGTTGTTCCCAAA (SEQ ID NO:765),

ERK2-7,5'-GGAGCAGTATTATGACCCA (SEQ ID NO:769), and

ERK2-8,5'-GACTGCTAGATTCCAGCCA (SEQ ID NO:770), targeting regions spanning 1063-1081, 1178-1196 and 1289-1307 on the mouse ERK2 cDNA (GenBank accession number NM_011949) respectively. The sequence of this mouse ERK2 cDNA is reproduced below for easy reference (SEQ ID NO:771).

```
   1 GACGCGAACC CTTCCCTCCT CCCACTCGTA GCCCGCCCGT
  41 CAGGCAGGAA GGCTGGCAGT GGTTCTACCG GCGGTTAATT
  81 CTCTCCTCTG TGTTGTCCTC CTTCCTCGTT CCCGATCGCC
 121 GGCGGGGCG GCTACACGGG CGGCAGCGCG GTTCCTGCGG
 161 GAAGCGCAGC ATAAGTCGAG CGGCAGCCGC GAAGCGTCGA
 201 ACCGAACGCG GCGGCGGCGG CGGCGGCGGC GGCTGTGCAG
 241 CCAACATGGC GGCGGCGGCG GCGGCGGGCC CGGAGATGGT
 281 CCGCGGGCAG GTGTTCGACG TAGGGCCGCG CTACACCAAC
 321 CTCTCGTACA TCGGAGAAGG CGCCTACGGC ATGGTTTGCT
 361 CTGCTTATGA TAATCTCAAC AAAGTTCGAG TTGCTATCAA
 401 GAAAATCAGT CCTTTTGAGC ACCAGACCTA CTGTCAAAGA
 441 ACCCTAAGAG AGATAAAAAT CTTACTGCGC TTCAGACATG
 481 AGAACATCAT TGGCATCAAT GACATCATCC GGGCACCAAC
 521 CATTGAGCAA ATGAAAGATG TATATATAGT ACAGGACCTC
 561 ATGGAGACGG ACCTTTACAA GCTCTTGAAG ACACAGCACC
 601 TCAGCAATGA CCACATCTGC TATTTTCTTT ATCAGATCCT
 641 GAGAGGGCTA AAGTATATCC ATTCAGCTAA CGTTCTGCAC
 681 CGTGACCTCA AGCCTTCCAA CCTCCTGCTG AACACCACTT
 721 GTGATCTCAA GATCTGTGAC TTTGGCCTTG CCCGTGTTGC
 761 AGATCCAGAT CATGATCACA CAGGGTTCTT GACAGAGTAC
 801 GTAGCCACAC GTTGGTACAG AGCTCCAGAA ATTATGTTGA
 841 ATTCCAAGGG TTATACCAAG TCCATTGATA TTTGGTCTGT
 881 GGGCTGCATC CTGGCAGAGA TGCTATCCAA CAGGCCTATC
 921 TTCCCAGGAA AGCATTACCT TGACCAGCTG AATCACATCC
 961 TGGGTATTCT TGGATCTCCA TCACAGGAAG ATCTGAATTG
1001 TATAATAAAT TTAAAGCTA GAAACTATTT GCTTTCTCTC
1041 CCGCACAAAA ATAAGGTGCC ATGGAACAGG TTGTTCCCAA
1081 ATGCTGACTC CAAAGCTCTG GATTTACTGG ATAAAATGTT
1121 GACATTTAAC CCTCACAAGA GGATTGAAGT TGAACAGGCT
1161 CTGGCCCACC CATACCTGGA GCAGTATTAT GACCCAAGTG
1201 ATGAGCCCAT TGCTGAAGCG CCATTCAAGT TTGACATGGA
```

```
1241 GTTGGACGAC TTACCTAAGG AGAAGCTCAA AGAACTCATT
1281 TTTGAAGAGA CTGCTAGATT CCAGCCAGGA TACAGATCTT
1321 AAATTGGTCA GGACAAGGGC TCAGAGGACT GGACGAGTTC
1361 AGATGTCGGT GTCCCCCCAG TTCTTTACCC TGGTCCTGTC
1401 TTCAGCCCGT CTCAGCTTAC CCACTCTTGA CTCCTTTGAG
1441 CCTTTCAGAG GGGCAGTTTC TGGTAGTAGC AGCTTTTATA
1481 CTTTCACGGA ATTCCTTCAG TCCAGAGAGT TCTGGCAGCA
1521 GGCCGTGCAG CAGTGTGCAC TTTCAATGCA CTTAACTGCT
1561 TACTGTTGTT TAGTCACGAA CTGCTTTCTG GTTTGAAAGA
1601 TGCAGTGGTT CCTCCCTGTT CTGAATCCTT TCTCCATATC
1641 ATGTGCTGAA CCATCAGCCT CATCAGAGGG AGAGTCTTTC
1681 CAGACTTGTT CCAGTTACTG GCACCTCACT TCACAGTAGG
1721 GAGGCTAGGA CATAAGGCAC CTTAAGTCAG TGACAGCTCC
1761 AAATTTGCAC TTCATCTGTT GGCTAGTAAC TGTCTACCTA
1801 GACAGTAGGA GCTTGTGGGT ATCCCTGGAT GGTATTACAG
1841 GCTACAGGGG CAGGGGCTTC TGTTCAGGA GTCCTTTGGG
1881 GCTATTTTCC TGTGTATCAT GTTAGTCCTA AATTTAAGGT
1921 ATGTACTATT TGCCCAGCTT TTTAAAAATT TGATCATTGT
1961 TTAAATGAAA TAGGAAGGAA GCATTGCACC AGCAGTATCT
2001 GTTGTTCTGC AGATTTTATA TGGTTACTTG TATCGTAATG
2041 GAGGTGGAGC TCTTGCCAAA ATGTTACATG CTATCCTTAG
2081 CCAGAGAGTG AAAGTAACAG CTGTGCTTGT CATTTACTGA
2121 AAGGTGGACA CACACAAAGC TGTGGAAGTT CCAGAACAG
2161 TAGAGAGCAA GCTGACCTAG ATGTTCAGGG CAGAGCTCCA
2201 TATAACCTTG AACAGCCACA CAGAAGGCTG TTTGCGTAAC
2241 CACATTCACT ACCTAGGGAT TTAGCTAAAA GGAACACTGC
2281 ATCTTTAAAT GAGAAAGTGT ACAGTTCTTC TCCTGCAGCA
2321 TGTCAGCATC TCGAGCTCAC TTTTCAGCAG TGTAATGACT
2361 TGTATGTAAT AAAGCCTTGA TGGGCTCTCC TCATGAAGCT
2401 CTGCTCTGTT GCCAAGTTAG AGATGTTTCT GGTACTGCTG
2441 AGTTAATGTC ATAAAAGGCT AGCAGTAACT GTTCGAGCTC
2481 TCTTTTATTT CCTTCTCTCC TATATTTTGT TCCTGCACTG
2521 TGTGCTGTGG AGTTGATGGT GTTATCCCAG TGCGGTGCCT
2561 CCAGACCCCC TCACTGCTCT CTGATGAGAA ATATGCCTTG
2601 TTCAATACTT ACTGTGCTCT TGCATGACTG TTAAGGTTTC
2641 TGTGCAGAGA CCAATGTCCA AGTGTCACAT CCTTTGATTG
2681 AACGAAATCT GTTGTGACCT CTGAGTTGTA TTCCATGAAG
2721 AGAATGCTAC CCAGAAGATA ATGTAGAAAA GATAATTATA
2761 TTGTTAACTT TTCATTTCTC AGCTGTCCTT TTGTTTTCTT
2801 GGTTTTTATT TTTTATTTTG ACATCAATGG AAAATGGGTT
2841 CTATAAAGAC TGCCTGCTAG TATGAACAGC AATGCAATGC
2881 ACTTGTAACT CATGGAAATA AATGTACATC TTTATCTTTA
2921 CACCCATGAT AAGATTCAGT GTTGATTTTC TCTGGATTGG
2961 TGTGTCCTAA GTAGGCACTC ATAATCAATT TATGGCTTGT
3001 GCTTCAGACA AAAATGTTCA TGGGCCTTAC TCTACTTCTC
3041 CCCACTCCAC CCTACCCCCC ATGCACTGCC CCTCACAGCA
3081 GTTTACGTAT ATGGCTGGGA AAGGTCCTTT TCAGCTGCAC
3121 ATGGTGCCAT GCATCGTTAA TCCCAGCATT CAGAAGTCAG
3161 AGGCAGGTGG ATCTCTGAAT GGAAGCAGGC CTGATTTGCA
3201 TAGGGAGGTC CAAGACAGCT GGAACTCTAT AGGTCCTGTC
3241 TCAAAAAAAA CAGAGTCCTC CCCGTCTGCC TCTCAGCAGC
3281 AAATGAATCT GACATGATCC TCTCTAAAAC AGGTCTCAAG
3321 TAGTCAGATG TTGATGATGG CACCCAAACA TGCCCAAGTT
3361 AGGATCTGGT TCCCTCTGAA AAGGGCCTTC TTGCCTCTGT
3401 ATCCTAGAGC TGTAGGAAGG GCTGTTCAAG ATCTCATGTA
3441 CCTGCTACCA AGTTCAAGGT AGCACATACC TCACCTGGCT
3481 AAAGAATGGC TGACTCATCC CAGAAACCAG ATCTCAGTTC
3521 TTGGCCTAAA TCCCTGCTTT TCACTTCCAC ACATGAAGCC
3561 CACTGGCATT GAAGGAATAG AGGTTCAGCT TTCATTGATA
3601 CAGTAGTGGT CAGTTTTCCT TTTTCTTTTT GTCTTTTTTT
3641 TTAAAGCACT GACTGTTCTC CTACTTGTTT CTTTTTCATA
3681 TTTTTAATCC CATGAGATTA ATTTGCATTC TTGTGAATAA
3721 GGAAACCATA GCCTCATCTT CTCGAGGTCT GAGCTTTCTG
3761 CCCTTCCTGG CACTGTGGAG AGGGGTTGGT GTGAGATCAC
3801 TCACTTCATC CTAGTCACTG TATCACAAGT GTGGCTTTCA
3841 TGTAGCCATT GTAAATGACA GCTCAGAGCT GTCAGGTATA
3881 GAAACGCTCA TTATTTTGGT TCTCATGTTT CTAAAAATGT
3921 TTGGATAACG TCATCTGCAT ACTGGTGTCA TTGGGTGCCT
3961 CTACTATTCA TACACATAGA TAAGCTGTCT GGTGGATGGG
4001 CTTTTTGTCC AAGTCTTAAT ATGTGAGGGA AAAAACCCA
4041 AAAACATGAA AACATTTAGC ATGAAGAAGA TAGCTATCCA
4081 ACAATCCCAG AGCGCTTGAT GATACCGGCA TTCAGAGCTG
4121 ACACTGACCT ACTCTGTGGT GCATTATTC TGCCCCCACC
4161 CTCATCCCTC TCATTTGAGG ACAGGCAACA CTTGGGCTGG
4201 GCATGACTGT TAGTTTTGGG AAGCTGTGAA TTAACAGCAG
4241 CTATCTCTGA GGAATCACAA AGGTAGACAC CTACACTGCA
4281 TGCCACATAG TATTCAGACC ACTTAGGGAG ACTTCCATTT
4321 GCTTAGGATA ATATTTACAT TAATATTAGT AGTTAGGTTT
4361 GAACTTTTGG TGACTTCTAT ACTACGGTAA CACATTCATA
4401 TATGCATATG CTTTGGGTCC TTCATACTAC TTTTTATATTT
```

```
4441 GTAAATCAGT GTTTTGGAGC AATTCCAAGT TTAAGGGAAA

4481 TATTTTTGTA AATGTGATGG TTTTGAAAAT CTGAGCAATT

4521 CTTTTGCTTA CAAGTTTTTT TAAAGCATTT GTGCTTTAAA

4561 ATTGTGCTAG TGTTTGGAAT ATGATACCCT ATAACCCAGA

4601 TAAGAAACAT AAGAATGGAG TAAACGCTGT CGCTTGTCGT

4641 GCTATGCCCA GCTTGGCGTG CTGGATCAGC AGTGGGACTC

4681 CGGAGTCCCT AGGGTCACAC CAGCTCACCT GCAGCTTGTT

4721 GCCTTTCTGT GCCGTCCGCC CGCCCTTCAG AGCACTCCAG

4781 AAAGTTCTGA CATGGCTCTG TATCTGCTCT GTACTGTGGA

4801 TGCCTTTTTG GTGTTGTATC CCAAACTGCA TAGATTATTT

4841 AGGATAATGA TAAGTTTAAA AAATTAATGT TGAAGAAAGA

4881 TTTTATTAAG AATTTAAATG TTTTTTCATT ATATTGTTAA

4921 ACTTGAACAT TTATCTGTGG CTTATGTGAT TTGGTTAATA

4961 TGTATAAAAA TTGTAAGAGG TTTATATTTC ATCTTAATTC

5001 TTTTGATGTT GTAAACGTGC TTTTCAATTC ATTATTTGAA

5041 TGTTTATGGC ACCTGACTTG TAAAAAGAAT TACAAAAAAA

5081 AAAATCCTTA GAATCATTA
```

A scrambled ERK2-7 sequence (MM), 5'-ACCCAGTAT-TATGACGAGG (SEQ ID NO:772) was used as the control.

In vivo delivery of the rAAV vectors. The viral vectors, ERK2-5, 2-7, 2-8 and MM were micro-injected into the spinal cord dorsal horn (SCDH) as described by South et al. (South et al., 2003). The mice were anesthetized with ketamine/xylazine. A laminectomy was performed to remove part of the dorsal L2 and L3 spinous process and the lumbar area of spinal cord was exposed for intraparenchymal injection (IPI). Three unilateral injections of 1 µl ($1-3\times10^9$ viral particles/µl) were administered 0.5-0.7 mm apart, at a depth of 0.3 mm from the dorsal border and 0.5 mm from the midline, using a glass pipette with a 40-µm-diameter tip attached to a 5 µl Hamilton syringe. The syringe was mounted on a microinjector (David Kopf Instruments, Tujunga, Calif.) attached to a stereotaxic unit (David Kopf Instruments). After the injection, the overlying muscles were closed with 5-0 chromic gut and the skins were closed with wound clips. Animals were allowed to recover for three weeks before undergoing behavioral tests, or sacrificed for histological and Western blot analysis.

Immunohistochemistry (IHC). Mice were anesthetized with pentobarbital and then perfused transcardially with 4% paraformaldehyde (PFA) in phosphate buffered saline (PBS) with 1 mM NaF. Fifty mL of fixative was perfused over 5 min by using a peristaltic pump. The spinal cord was dissected and placed in 4% PFA for 1 hr before being transferred to 30% sucrose for cryoprotection for 72 hr. Lumbar spinal cord cryosections of 20-µm thick were obtained from a cryostat (Leica, Bannockburn, Ill.) for IHC and in situ hybridization.

For IHC, the spinal cord sections were incubated in blocking solution (3% normal goat serum, 0.1% Triton X-100 in Tris buffered saline) for 30 min. After washing in Tris buffered saline (TBS), sections were incubated with one or two of the following primary antibodies: rabbit anti-GFP (1:1000; Invitrogen-Molecular Probes Inc, Eugene, Oreg.), rabbit anti-phospho-ERK1/2 (1:1000; Cell Signaling Technology, Inc., Danvers, Mass.), mouse anti-NeuN (1:400; Millipore-Chemicon, Bedford, Mass.), rabbit anti-c-fos (1:2000, Santa Cruz Biotechnology, Santa Cruz, Calif.), rabbit anti-Dynorphin A(1:2000, Bachem, San Carlos, Calif.), mouse anti-GFAP (1:2000; Millipore-Chemicon) and rat anti-OX42 (1:1000, BD Biosciences, San Diego, Calif.) overnight in blocking solution at 4° C. The sections were washed in TBS and then incubated in appropriate fluorescent secondary antibodies or biotinylated goat anti-rabbit or anti-mouse IgG (1:250; Vector Laboratories, Burlingame, Calif.) in blocking solution. Biotin slides were further incubated with 3,3-diaminobenzidinetetra-hydrochloride (DAB). Fluorescent slides were mounted in the anti-fading mounting medium Gel-Mount (Invitrogen, Eugene, Oreg.). DAB slides were dehydrated through a series of ethanol and xylenes, then coverslipped in Permount (Thermo Fisher Scientific, Inc., Waltham, Mass.). To minimize variability in staining, tissues from all treatment groups were run in the same session. A negative control was performed using diluted normal goat serum instead of the primary antibody.

Non-radioactive in situ hybridization. ERK2 mRNA expression in the SCDH was detected by non-radioactive in situ hybridization as described by (Garraway et al., 2007). Digoxigenin (DIG) labeled antisense or sense riboprobes were synthesized using an in vitro transcription kit (Roche Applied Science, Indianapolis, Ind.) from the mouse ERK2 cDNA (kindly provided by Dr. Michael J. Weber, University of Virginia). On day 1, slide mounted cryosections of spinal cord (20 µm) were incubated in the following: (1) 4% paraformaldehyde (PFA) in phosphate buffer saline (PBS) for 20 min; (2) PBS, three times for 5 min each; (3) Proteinase K solution (Sigma) for 2 min; (4) PBS, twice for 5 min each; (5) 4% PFA in PBS for 5 min; (6) PBS for 5 min; (7) 0.25% acetic anhydride in 0.1 M Triethanolamine for 10 min; (8) 2×SSC, twice for 5 min each. Next sections were incubated in pre-hybridization solution (50% formamide, 0.3M NaCl, 10 mM Tris pH 8.0, 1 mM EDTA, pH 8.0, 500 µg/ml salmon sperm DNA and 500 µg/ml yeast tRNA) at 55° C. in a chamber containing towels moistened with 4×SSC and 50% formamide. After incubation for 2 hr, the pre-hybridization solution was drained and sections were hybridized with DIG-labeled antisense or sense probes for ERK2 (1:1000), coverslipped, and placed in a 55° C. oven overnight. On day 2, the coverslips were removed and the hybridized spinal cord sections were sequentially incubated in the following: (1) 5×SSC at 55° C. for 10 min; (2) 50% formamide in 2×SSC at 55° C. for 20 min; (3) RNAse buffer at 37° C., twice for 5 min each; (4) RNAse A (50 µg/mL, Sigma) at 37° C. for 30 min; (5) RNAse buffer at 37° C. for 15 min; (6) 50% formamide, 2×SSC at 55° C. for 20 min; (7) 2×SSC, twice for 15 min each; (8) washing buffer for 10 min; (9) blocking solution for 30 min; (10) anti-DIG antisera conjugated to alkaline phosphatase (1:500) for 2 hr; (II) washing buffer, twice for 15 min each; (12) detection buffer for 5 min; (13) nitro blue tetrazolium/5-bromo-4-chloro-3-indolyl phosphate (NBT/BCIP) overnight. On day 3, slides were rinsed in distilled water and dehydrated through a graded ethanol series, xylenes, and coverslipped in Permount (Thermo Fisher Scientific, Inc.).

Microscopic analysis. Fluorescent IHC images were captured by a Zeiss LSM 510 laser scanning confocal microscope. Bright field IHC and in situ images were captured by a Nikon Eclipse 80 i microscope (Nikon, Melville, N.Y.) equipped with a digital CoolSnap camera (Photometrics, Huntington Beach, Calif.) through an interface between the camera and a Macintosh computer using the IPlab software (BD Biosciences Bioimaging, Rockville, Md.). Quantitative analysis was performed by a blinded observer using Metamorph software (Universal Imaging, Downingtown, Pa.) as described previously (Garraway et al., 2007). A total of 4-5 sections spacing 400-500 μm apart were used for each animal. At least three animals were included in each treatment group.

Immunoblot. Animals were deeply anesthetized by isoflurane, decapitated and the lumbar spinal cord dorsal horn at the level of L4-L6 were rapidly dissected. The right and left dorsal horn were separated and immediately homogenized in modified RIPA buffer (50 mM Tris-HCl, pH7.4, 1% NP40, 1 mM EDTA, 150 mM NaCl) supplemented with protease inhibitor cocktail (Sigma) diluted 1:10, 2 mM PMSF, 2 mM NaF and phosphatase inhibitor cocktail I and II (Sigma), then frozen in liquid nitrogen. After all the samples were collected, tissues were thawed on ice, sonicated and centrifuged at 4° C. at 14000 g for 10 min to obtain the supernatant. The protein level of each sample was measured by the BioRad DC assay. Samples were then diluted in Laemmli sample buffer on the same day to a final concentration of 2 ug/ul, boiled for 5 min and stored at −80° C.

The spinal cord dorsal horn samples were separated on SDS-PAGE gels (10% Tris-HCl gel; Bio-Rad, Hercules, Calif.) and transferred to polyvinylidene difluoride filters (PVDF, Millipore, Bedford, Mass.), which were subsequently blocked in blocking solution (5% dry milk in TBS with 0.1% Tween-20) for at least an hour. Membranes were incubated with rabbit anti-pERK1/2 antibody (1:1000; 07-362; Cell Signaling Technology, Inc.) in blocking solution overnight at 4° C., washed in TBS with 0.1% Tween-20 (TBST), then incubated with HRP-conjugated anti-rabbit IgG (1:1000, Pierce Biotechnology, Inc., Rockford, Ill.) in blocking solution for 1 hr. Membranes were washed with TBST followed by TBS and developed using SuperSignal West Pico ECL kit (Pierce Biotechnology, Inc.), then exposed to film (Kodak, Rochester, N.Y.) for various times. Next, membranes were stripped (Pierce) and reprobed for ERK1/2 using rabbit anti-ERK1/2 antibody (1:5000, Cell Signaling Technology, Inc.) followed by HRP-conjugated anti-rabbit secondary antibody (1:10,000, Pierce Biotechnology, Inc.). For loading control, blots were further stripped and re-probed for β-actin using a mouse monoclonal antibody (1:50,000, Sigma) followed by HRP-conjugated anti-mouse secondary antibody (1:200,000, Pierce Biotechnology, Inc.). Exposures yielding signal intensity in the linear range without saturation were used for densitometry analysis with Fluorchem 9900 (Alpha Innotech, San Leandro, Calif.). Ratios of intensity of pERK1/2 or ERK1/2 to β-actin were calculated, normalized to the control samples and subject to statistical analysis. At least 4 animals were included in each treatment group.

Behavioral testing. All behavioral testing was conducted in groups of 10 mice per treatment by a blinded observer. Motor function tests were performed before mechanical stimulus threshold or thermal paw withdrawal threshold were measured (Garraway et al., 2007). No deficits in reflexes for surface righting, placing/stepping and grasping/climbing were found in animals treated with either the control rAAV vector or rAAV viral vectors.

Mechanical stimulus threshold to a non-noxious mechanical stimulus was determined by paw withdrawal to the application of a series of calibrated von Frey filaments to the surface of the hind paws. The animals were placed in a Plexiglas cage with mesh flooring suspended above the researcher and left to acclimate for 30 min. von Frey filaments were applied perpendicularly against the mid-plantar surface of the foot. The "up-down" method of Dixon (Chaplan et al., 1994) was used to determine the value at which paw withdrawal occurred 50% of the time, interpreted as the mechanical threshold.

Thermal paw withdrawal threshold was assessed using a thermal nociceptive stimulus apparatus (Hargreaves et al., 1988). Prior to the test, the animals were allowed to acclimate for 30 min to the test chamber on a pre-heated glass plate maintained at 30° C. A radiant thermal stimulus (5.10 amps) was applied to the mid-plantar surface of the hind paw through the glass plate. The latency, in seconds, for the withdrawal of the paw from the heat source was determined automatically. If no response was elicited, the heat source was automatically shut off at 20 sec to prevent tissue injury. A minimum break of 5 min was allowed between each trial. Three to six trials were performed for each paw.

Fifteen μl of Complete Freund's adjuvant (CFA, Sigma) was injected into the right hind paws of lightly restrained mice. The mice had received either the control vector MM or siRNA vector 2-7 in the right spinal cord dorsal horn at least three weeks prior to the intraplantar injection of CFA. Mechanical stimulus threshold, thermal paw withdrawal threshold and paw size were measured before (baseline) and at 24, 48 and 96 hr after CFA.

Statistical analysis. The immunohistochemical, in situ hybridization, Western blot and behavioral data were analyzed by one-way ANOVA followed by the Student-Newman-Keuls test (multiple groups) or the t test (two groups) using the InStat software (GraphPad, version 3.00, San Diego, Calif.). The data are represented as mean±SEM.

EXAMPLE 2

Reduction of ERK2 Expression Inhibits Pain in Mice

This Example describes the effects of inhibiting ERK2 expression by siRNAs that are specifically targeted to ERK2.

Figure 1J:
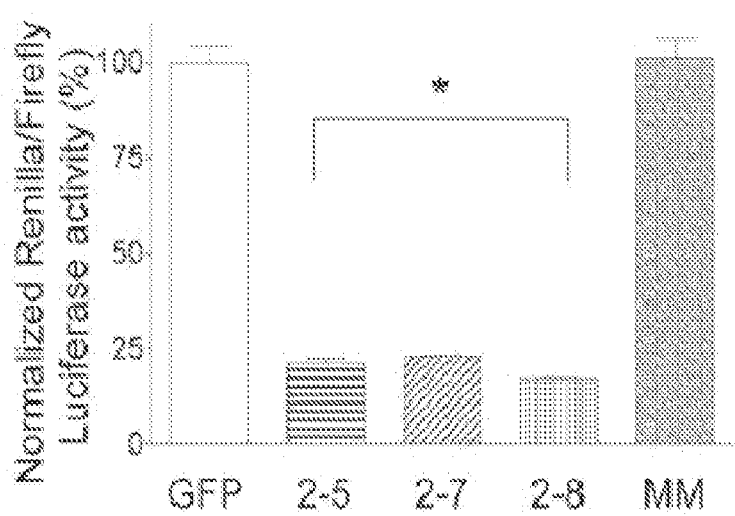

Knockdown of ERK2 expression in the lumbar spinal cord dorsal horn neurons by rAAV vectors expressing active siRNAs. Three serotype-2 rAAV vectors (vector 2-5, 2-7 and 2-8) expressing ERK2 siRNAs and one control vector expressing a scrambled siRNA (vector MM) were used in the current study. The psiCHECK Dual Luciferase Assay was performed before the virus preparation and injection to examine the ability of vectors to inhibit ERK2 expression in cultured cells. Compared to a control rAAV plasmid that did not express an siRNA, all three active siRNA vector plasmids significantly inhibited the activity of Renilla luciferase, which was translated from a fusion mRNA containing the ERK2 and luciferase cDNA sequences. The control MM vector was ineffective in this assay (FIG. 1J).

The rAAV vectors were injected intraparenchymally into the spinal cord dorsal horn of adult mice. Three weeks after intraparenchymal injection of rAAV vectors, a robust and spatially localized expression of GFP was observed on the ipsilateral side of lumbar spinal cord dorsal horn (FIG. 1A-D). The expression of GFP resulting from each of the four rAAV vectors extended for more than 3 mm rostrocaudally, encompassing the full L4, L5 and L6 spinal segments in mouse. In situ hybridization was performed on slides adjacent to the GFP slides to examine the mRNA expression of ERK2. On the side contralateral to the vector injection, ERK2 mRNA was observed in the gray matter. Vector MM did not alter the ERK2 mRNA level (FIG. 1E) in the ipsilateral dorsal horn. In contrast, there was a nearly complete depletion of ERK2 mRNA in the region corresponding to the GFP immunolabeling in animals treated with vector 2-5, 2-7 or 2-8 (FIG. 1F-H). A densitometry analysis of the in situ images showed that the extent of ERK2 mRNA knockdown was similar among the three active siRNA vectors, ranging from 75% to 80% reduction on the ipsilateral side compared to the contralateral side (II, p<0.05, vs. vector MM).

To determine whether vector administration resulted in glial activation, sections of SCDH were compared from mice that were untreated or had received either the vector MM or the active siRNA vector 2-7 at 3 weeks before the analysis. One example of the immunolabeling is shown in FIG. 2G. Compared with sections from untreated mice, there was no evidence of hypertrophy, thickened processes, or enlarged cell bodies in GFAP-labeled astrocytes (Guo et al., 2007) or the shortened, thickened processes seen with activated microglia labeled with OX42 (Raghavendra et al., 2004). Examination of sections at a higher magnification than is shown in FIG. 2G supported these observations (data not shown). There was no evidence of neuronal cell loss, a finding consistent with a previous observation that vector derived siRNAs did not result in loss of nuclei in the spinal cord dorsal horn (Garraway et al., 2007).

GFP immunolabeling was colocalized with NeuN, a neuronal marker, but not with GFAP, an astroglial marker, or with OX42, a microglial marker, as revealed by confocal fluorescent immunohistochemistry in animals that received the control MM vector (FIG. 3G1-G9) or siRNA vector 2-7 (FIG. 3H1-H9). There was no evidence of gliosis in the spinal cord dorsal horn of animals treated with either vector.

Due to the high sequence similarity between the ERK1 and ERK2 proteins and the lack of a specific ERK2 antiserum, immunohistochemistry was not able to distinguish between ERK1 and ERK 2 expression. Therefore, Western blot analysis was used to quantify the knockdown of ERK2 expression. Compared to the control vector MM, vector 2-7 induced greater than 50% reduction in the expression of ERK2 in the ipsilateral spinal cord dorsal horn (FIGS. 2A and B, p<0.05), while the expression of ERK1 was not affected (FIGS. 2A and C). This knockdown was not present on the contralateral side (FIGS. 2A and B). As expected, the level of phospho-ERK2 (pERK2), the active form of ERK2, was also decreased on the ipsilateral side in animals treated with vector 2-7 compared to control vector MM (FIGS. 2D and 2E, p<0.05). Interestingly, there was an accompanying increase in pERK1 in blots from these animals (FIGS. 2D and 2F, p<0.05), suggesting a loss of competition between ERK1 and ERK2 for their binding and activation by MEK. Vector MM did not have any effect on the expression or phosphorylation of ERK1 and ERK2 compared to animals that did not receive intraparenchymal injection of a vector (FIG. 5A-E).

Figure 3A:
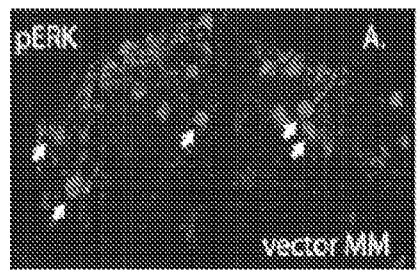
Figure 3D:
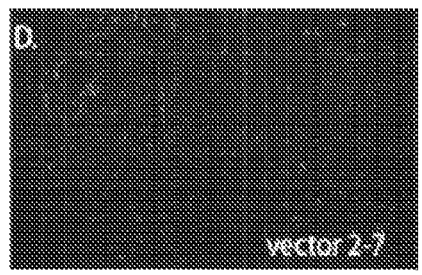
Figure 3B:
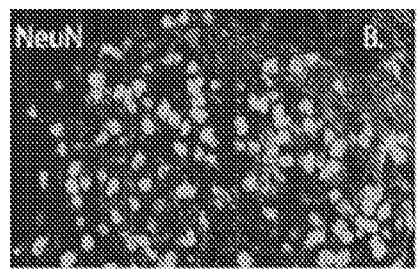
Figure 3E:
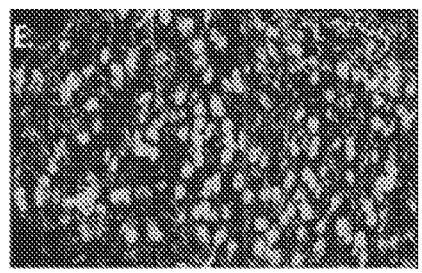
Figure 3C:
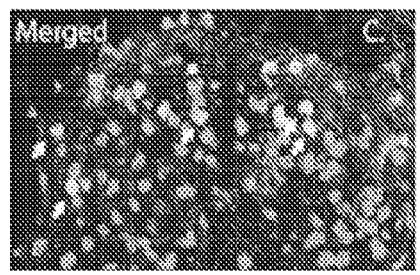
Figure 3F:
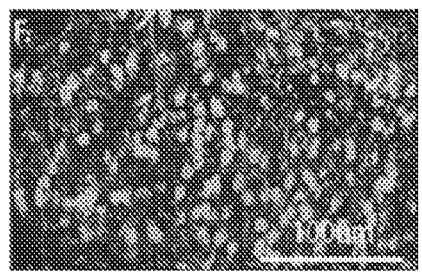

The cellular localization of pERK1/2 on spinal sections was examined using an antibody that recognizes both pERK1 and pERK2. In animals that received the control vector MM, pERK1/2 was observed in the lumbar spinal cord dorsal horn, mainly in lamina I and II (FIG. 3A). Confocal double fluorescent immunohistochemistry revealed that pERK1/2 immunolabeling was co-localized with NeuN (FIG. 3A-C) but not with GFAP or OX42 (data not shown). In animals treated with siRNA vector 2-7, the pERK1/2 immunolabeling was dramatically decreased in the ipsilateral dorsal horn (FIG. 3D-F), suggesting that pERK1/2 immunolabeling is mainly comprised of pERK2. As stated previously, an increase in pERK1 accompanying ERK2 knockdown was observed. However, the increase in phosphorylation of ERK1 was apparently not sufficient to overcome the knockdown of ERK2 expression and phosphorylation in these spinal cord dorsal horn neurons.

Knockdown of ERK2 expression prevented ERK activation in the spinal cord dorsal horn following intraplantar CFA administration. Injection of the Complete Freund's Adjuvant (CFA) into the hindpaw of mouse induces a rapid increase in the phosphorylation of ERK1 and ERK2 in the ipsilateral lumbar spinal cord dorsal horn, which is then maintained for at least 7 days (Ji et al., 2002; Adwanikar et al., 2004). This induction is associated with the development of hyperalgesia and allodynia in the injected paw. ERK1/2 may regulate their targets by either post-translational or transcriptional mechanisms, presumably at different stages of the injury-induced pain. Therefore, ERK1/2 phosphorylation was examined in the lumbar spinal cord dorsal horn at both 1 hour and 96 hour after injection of the Complete Freund's Adjuvant (CFA).

Figure 4A:
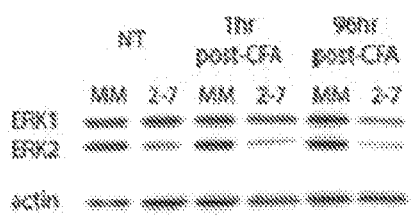
FIGS. 4A-F show that siRNA vector 2-7, but not the control MM vector, reduces ERK2 expression in the ipsilateral spinal cord dorsal horn (SCDH) and prevents the phosphorylation of ERK2 that is typically induced by intraplantar administration of Complete Freund's adjuvant (CFA).
Figure 5A:
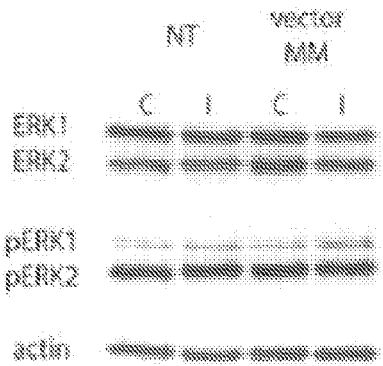
FIG. 5A-F show that the control vector MM did not change the expression or phosphorylation of ERK1 and ERK2 compared to mice that did not receive treatment (NT).
Figure 5D:
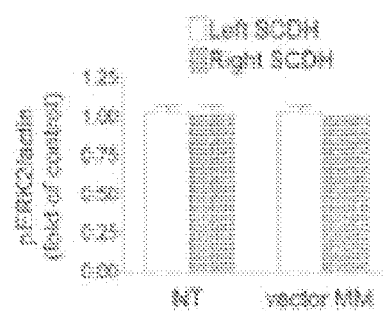
Figure 5B:
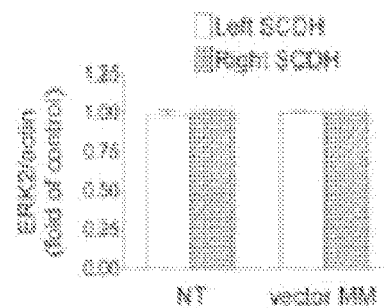
Figure 5E:
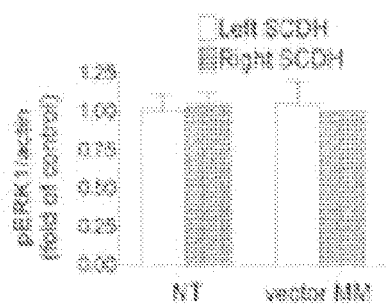
Figure 5C:
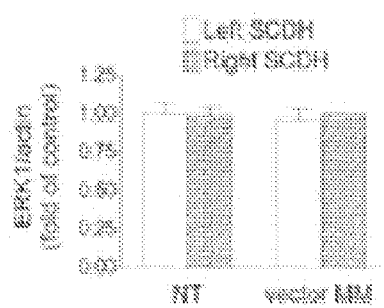
Figure 5F:
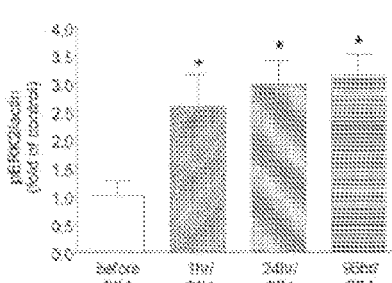

As illustrated in FIG. 4A, Western blot analysis showed a significant reduction in ERK2 in the ipsilateral spinal cord dorsal horn after administration of vector 2-7 compared to the control MM vector. The reduction was observed at 1 hr and maintained to 96 hr after CFA injection (p<0.05, vs. vector MM). In the control animals, ERK2 was increased at 96 hr after CFA in the ipsilateral spinal cord dorsal horn compared to no treatment (NT) or 1 hr (FIGS. 4A and B, p<0.05). There was also an increase in ERK1 expression at 96 hr in the control animals compared to no treatment and 1 hr (FIGS. 4A and C, p<0.05). Vector 2-7 did not alter ERK1 expression and prevented the ERK1 increase induced by CFA (FIGS. 4A and C). In control mice (no vector treatment), CFA induced an increase in pERK2 at 1 h that persisted at 24 and 96 h after CFA (FIG. 5F).

Figure 4D:
Figure 4B:
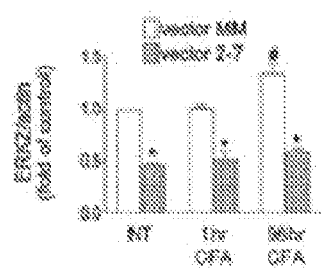
Figure 4E:
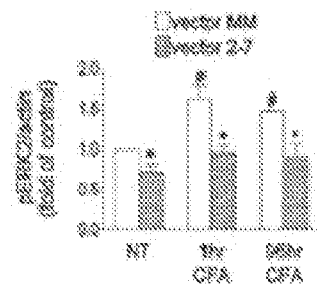
Figure 4C:
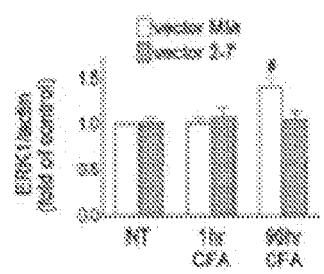
Figure 4F:
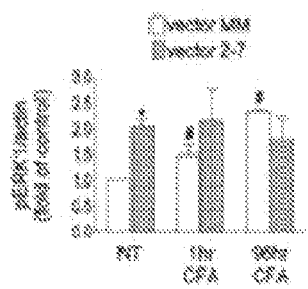

There was a decrease in basal pERK2 after vector 2-7 was administered and this reduction persisted from 1 hr to 96 hr after CFA (FIGS. 4D and E, p<0.05, vs. vector MM). In contrast, pERK2 was increased at 1 hr and 96 hr after CFA in the control animals treated with vector MM (FIGS. 4D and E, p<0.05, vs. vector MM/NT). Basal pERK1 was increased as a result of intraparenchymal injection of vector 2-7. This increase was not altered by CFA at either 1 hr or 96 hr. In contrast, pERK1 was increased by CFA in the control vector MM group at 1 hr and 96 hr (FIGS. 4D and 4F, p<0.05, vs. vector MM/no treatment). These results clearly demonstrated that the increases in ERK2, ERK1 and pERK2 following CFA were prevented by vector 2-7, although vector 2-7 induced an increase in basal pERK1 level.

Figure 6G:
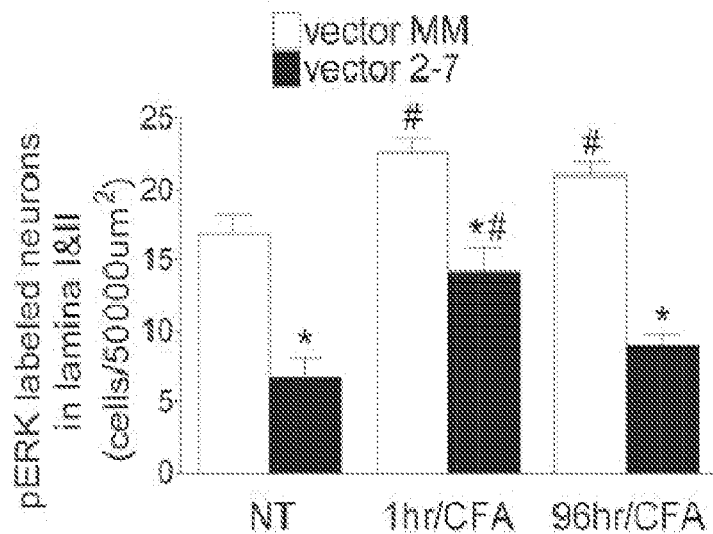
Figure 6H:
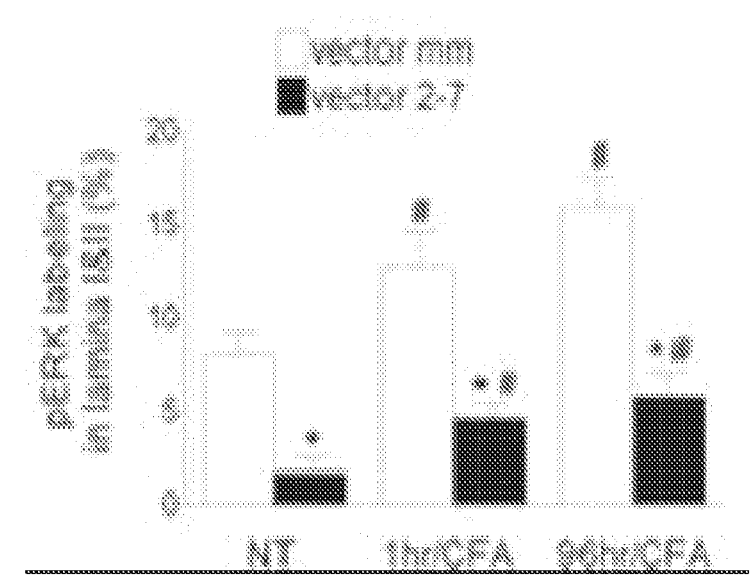

Next, 3,3-diaminobenzidinetetra-hydrochloride (DAB) immunohistochemistry was performed to quantify and localize pERK1/2 changes in the spinal cord dorsal horn after CFA. In the control vector MM group, immunolabeling of pERK1/2 was observed mainly in laminas I and II in the ipsilateral spinal cord dorsal horn. Intraplantar CFA injection induced a significant increase in the pERK1/2 labeling at 1 hr and 96 hr, measured as the number of pERK of labeled neurons in laminas 1 and II or percentage of field (FIG. 6A-C,G, H) (p_0.05 vs vector MM/no treatment). The level of pERK1/2 immunolabeling in the vector 2-7 group was significantly lower than the control group at each corresponding time point (FIG. 6D-G,H)(p<0.05 vs vector MM).

Figure 7A:
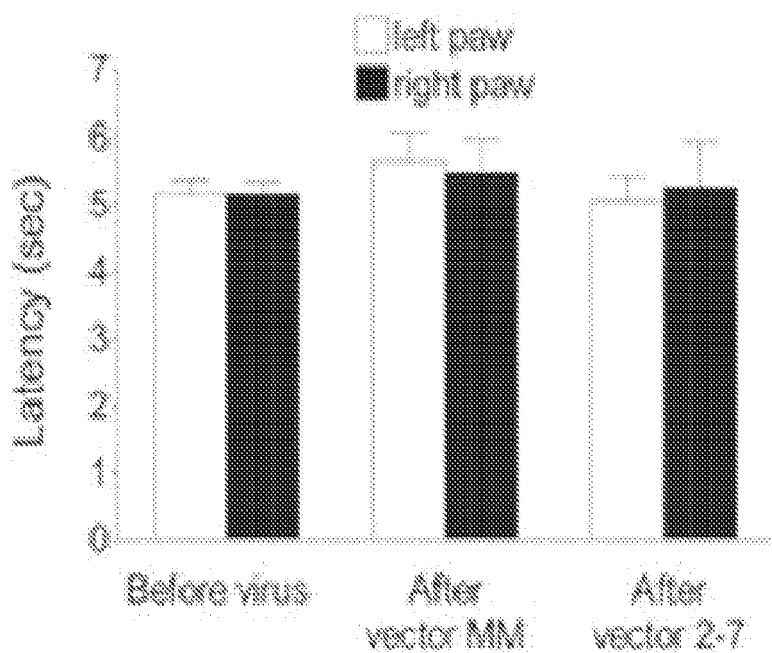
FIGS. 7A-B graphically illustrate that a spatial knockdown of ERK2 in the spinal cord dorsal horn (SCDH) by siRNA vector 2-7 does not affect thermal (FIG. 7A) or mechanical (FIG. 7B) paw-withdrawal thresholds. A brief thermal stimulus was applied to the paw (FIG. 7A), or mechanical (tactile) stimuli were applied using von Frey hairs (FIG. 7B). These thresholds were measured before and 3 weeks after the ipsilateral intraparenchymal injection of vector into the right SCDH of either the control vector (MM) or the siRNA vector 2-7 (n=10 per treatment group).
Figure 7B:
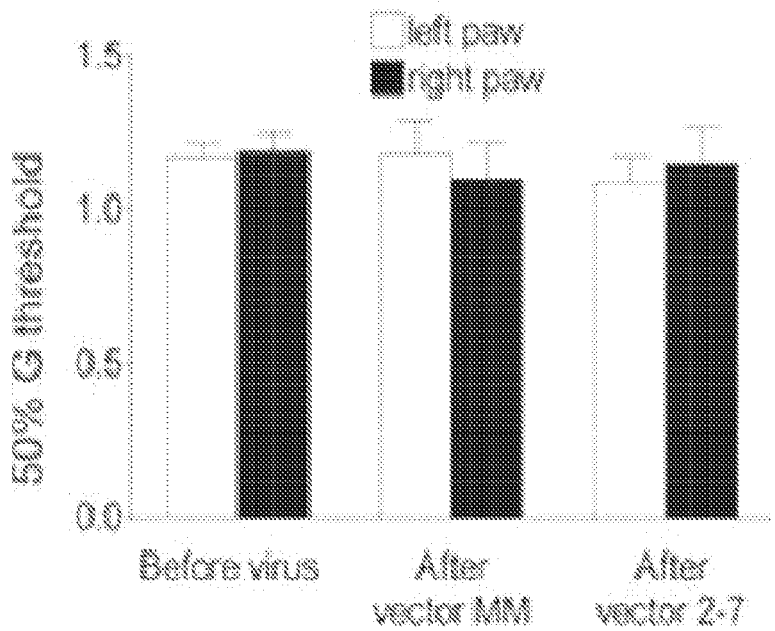

Effects of the knockdown of neuronal ERK2 in the spinal cord dorsal horn on motor reflexes, acute thermal and mechanical thresholds. To investigate the functional consequences of the ERK2 knockdown, the motor reflexes, hind paw thermal withdrawal latency, and mechanical withdrawal threshold in animals were first examined before and after intraparenchymal injection of each viral vector. None of the animals that received either control vector MM or vector 2-7 exhibited any signs of motor deficits (data not shown). No change was observed in heat withdrawal latency or mechanical withdrawal threshold, when tested at least 3 weeks after the vector administration (FIGS. 7A and 7B), indicating that neither the intraparenchymal injection procedure nor knockdown of neuronal ERK2 in the spinal cord dorsal horn affected acute pain thresholds.

Figure 8A:
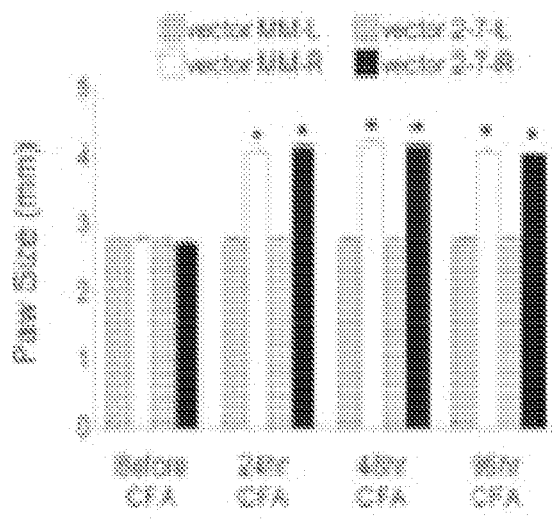
FIGS. 8A-C illustrate that a spatial knockdown of ERK2 in the spinal cord dorsal horn (SCDH) by vector 2-7 significantly reduces thermal hyperalgesia (FIG. 8B) and mechanical allodynia (FIG. 8C) resulting from the intraplantar injection of the inflammatory agent, Complete Freund's adjuvant (CFA).
Figure 8B:
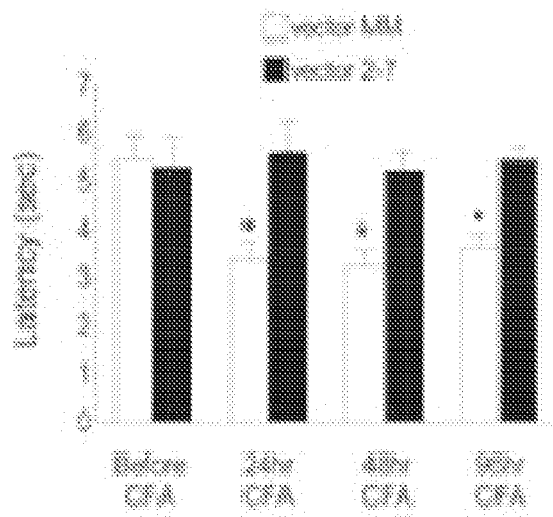
Figure 8C:
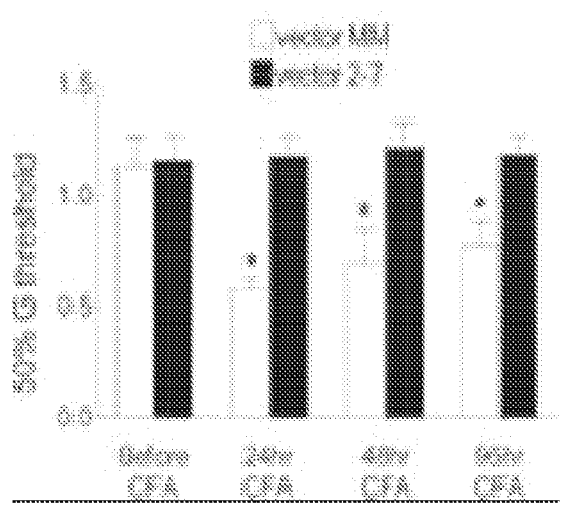

Knockdown of ERK2 in the spinal cord dorsal horn prevented CFA-induced pain. After intraplantar CFA administration, there was an equal increase in paw size in animals treated with either the control vector MM or the siRNA vector 2-7 (FIG. 8A, p<0.05, vs. baseline, n=10 per treatment group), indicating a similar degree of peripheral inflammation. However, only the vector control animals exhibited significant decreases in the thermal withdrawal latency (thermal hyperalgesia) (FIG. 8B, p<0.05) and mechanical withdrawal threshold (mechanical allodynia) (FIG. 8C, p<0.05) at 24, 48 and 96 hr after CFA. The ERK2 knockdown in the spinal cord dorsal horn protected the animals from developing thermal hyperalgesia and mechanical allodynia for up to 96 hr after CFA (FIGS. 8B and 8C).

Figure 9C:
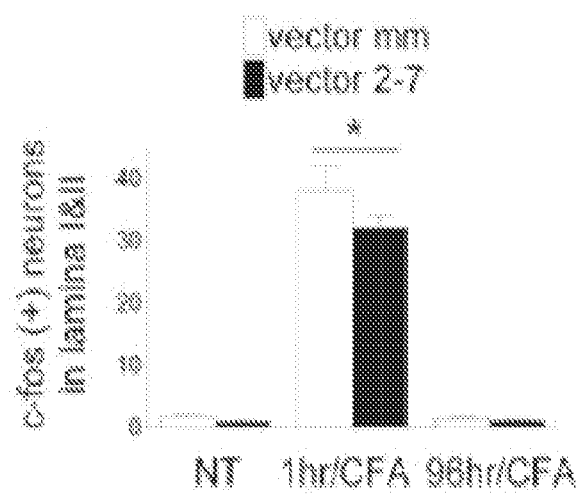
Figure 10G:
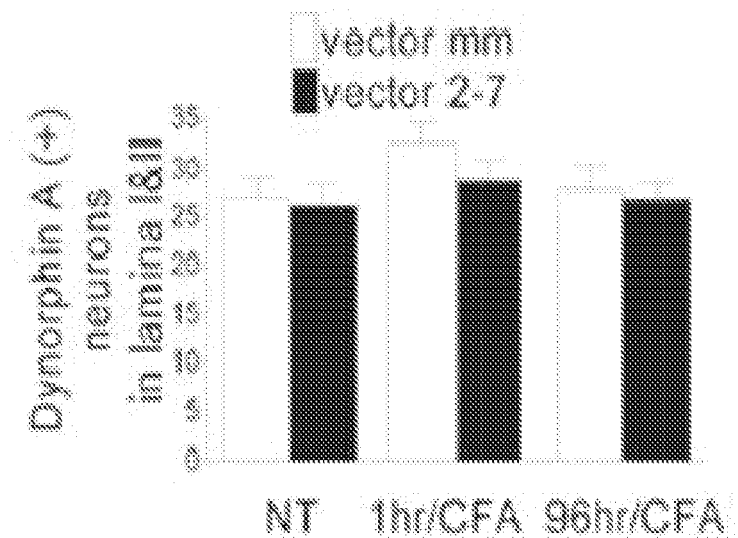
Figure 10H:
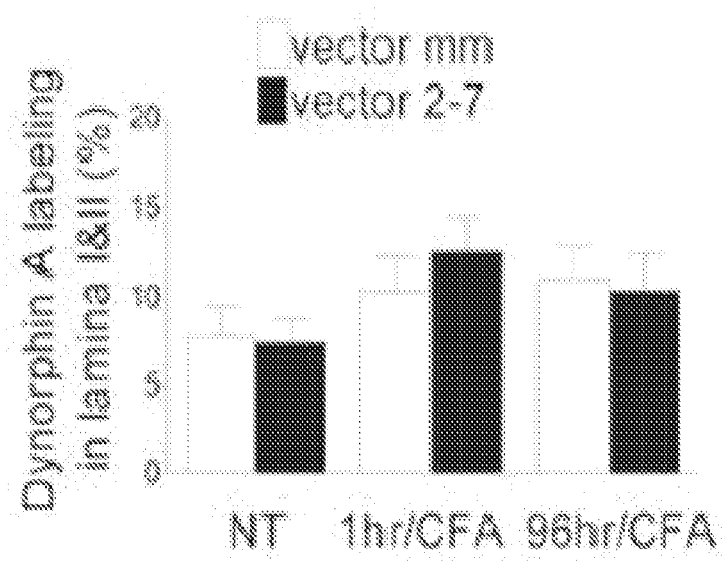

The expression of c-fos and dynorphin A following CFA. To investigate how ERK2 knockdown may prevent CFA-induced inflammatory pain, the expression of c-fos (FIG. 9) and dynorphin A (FIG. 10) was examined. These two genes may be regulated by ERK via CRE-mediated mechanism and lead to long-lasting synaptic modifications in pain (Ji et al., 2002; Obata et al., 2003). A very low level of c-fos immunolabeling was observed before CFA. At 1 hour after CFA, the expression of c-fos was strongly induced in the ipsilateral spinal cord dorsal horn. This induction was equal in both groups of animals and diminished at 96 hr. Dynorphin A immunolabeling was not different in animals that received vector 2-7 compared with the control animals. In addition, no changes were observed in the level of dynorphin A at either 1 hr or 96 hr after CFA. These results indicate that the expression of c-fos or dynorphin A is unlikely to be regulated by neuronal ERK2 at either 1 hr or 96 hr following CFA.

This is the first report of spatial-temporal knockdown of ERK2 gene expression mediated by a siRNA in the spinal cord dorsal horn of adult mice. The ERK2 siRNAs delivered by a neurotropic rAAV vector produced a localized reduction in the basal level of both ERK2 and its phosphorylated form (pERK2) in spinal cord dorsal horn neurons. The increase in both ERK2 and pERK2 induced by intraplantar CFA in the spinal cord dorsal horn of control mice was prevented by the ERK2 siRNA. In addition, the ERK2 siRNA vector protected the mice from CFA-induced thermal hyperalgesia and mechanical allodynia for at least 96 h.

The rAAV vector-based siRNA approach presents a potent and facile tool to produce a spatial and temporal knockdown of the expression of a gene of interest (Garraway et al., 2007). Several factors dictated the choice of a rAAV vector for the delivery of the ERK2 siRNA. First, the serotype-2 rAAV vector used in the current study selectively transduces neurons in vivo (Kaspar et al., 2002). Second, rAAV is able to mediate long-term siRNA expression and gene knockdown in the transduced cells. Although the GFP and ERK expression was examined for only 6 weeks, previous studies by the inventors demonstrated that a single administration of a rAAV vector resulted in the knockdown of NR1 gene expression that persisted for at least 6 months (Garraway et al., 2007). Third, rAAV is safe and therefore convenient to use in behavioral experiments requiring repeated measurements. Fourth, rAAV mediated gene knockdown could be controlled both temporally and spatially. This conditional approach avoids embryonic lethality associated with a constitutive knock-out of ERK2 (Hatano et al., 2003; Saba-El-Leil et al., 2003; Yao et al., 2003).

Consistent with the observations described herein, several reports (Kaspar et al., 2002; South et al., 2003; Garraway et al., 2007) have provided evidence at the ultrastructural and light microscope levels as well as direct behavioral threshold evidence that the injection of AAV into the brain or spinal cord dorsal horn does not result in significant immune or glial activation or behavioral sensitization. It has been reported that a high dose of a siRNA might induce nonspecific and off-target effects (Bridge et al., 2003; Sledz et al., 2003). However, previous studies by the inventors indicated that neither an NR1 siRNA nor a control siRNA delivered by the rAAV vector induced detectable cellular toxicity (Garraway et al., 2007). Transduced neurons exhibited unaltered expression of NeuN compared with the contralateral side. In addition, no signs of gliosis or neuronal damage were observed (FIG. 2G). The three vectors expressing different siRNAs induced a similar degree of GFP expression and knockdown of the ERK2 mRNA in the spinal cord dorsal horn, suggesting the knockdown is unlikely to be induced by nonspecific or off-target effects. The knockdown clearly targets the ERK2 mRNA and protein as revealed by in situ hybridization and Western blot. The closely related ERK1 was unaffected at the protein level.

Thus, the data clearly show that the ERK2 siRNA vector 2-7 greatly reduced basal and induced pERK immunolabeling in the spinal cord dorsal horn (FIG. 3A,D) and that this pERK species was pERK2 as measured by Western blot (FIG. 2D). Moreover, the ERK2 knockdown completely blocked CFA-induced thermal hyperalgesia and mechanical allodynia. Additional experiments examining inflammatory pain behaviors earlier than 24 hour after CFA are required to demonstrate the role of ERK2 in the early induction of inflammatory pain.

Injury-inducing stimuli such as intraplantar CFA injection result in a rapid activation of ERK1/2 in the spinal cord dorsal horn. NMDA receptors play a major role in ERK1/2 activation (Ji et al., 1999; Cheng et al., 2008), although other players are also involved (Kawasaki et al., 2004). This activation of ERK1/2 after CFA is sustained at 24 h and persists for at least 96 h. Several sources may contribute to the prolonged ERK1/2 activation, such as sustained primary afferent input from the periphery. The injected hindpaw remains swollen at 96 h, indicating an ongoing peripheral inflammation. Another source could be the descending excitatory pathway from supraspinal sites (Svensson et al., 2006).

ERK1/2 can phosphorylate several pain-related proteins including the NR1 subunit of the NMDA receptor (Krapivinsky et al., 2003) and the Kv4.2 potassium channel (Hu et al., 2006). Phosphorylation of these proteins can contribute to the central sensitization in spinal neurons after peripheral injury, which leads to increased membrane excitability in the affected neurons. In addition to its role in the posttranslational regulation, ERK1/2 may also maintain pain hypersensitivity by promoting transcription of genes that are important for neuronal plasticity. A major transcription factor activated by ERK1/2 is cAMP response element-binding protein (CREB), which in turn induces transcriptional activation of many genes such as c-fos, TrkB (Obata et al., 2003), NK-1, and prodynorphin (Ji et al., 2002) via CRE-mediated mechanism. As described above, the immediate-early gene c-fos was activated in the SCDH in control animals at 1 h but not 96 h after CFA. However, a comparable change was observed in the ERK2 knockdown animals, indicating c-fos was activated by ERK2-independent mechanisms. No changes were detected in the level of dynorphin A at 1 or 96 h after CFA.

ERK1 and ERK2 mRNA levels are upregulated at 12 h after formalin (Li et al., 2004). We found the expression of ERK1 and ERK2 protein remains upregulated at 96 h after intraplantar CFA in control animals, but was prevented by the ERK2 siRNA vector.

EXAMPLE 3

Reduction of ERK2 Expression in Human Cells

This Example illustrates that ERK2 expression can be inhibited by siRNAs that are specifically targeted to human ERK2.

Separate cultures of an immortalized cell line of human embryonic kidney cells (HEK293) were transfected with three active siRNAs directed against human ERK2. Another culture of HEK293 cells was transfected with an inactive control mismatch (MM) siRNA. The sequences of the three human ERK2 siRNAs (#1, #2, and #3) and the control mismatch siRNA are shown below.

```
#1 (1833-1851):
GCAGGAGCUUGUGGAAAUAUU      (SEQ ID NO: 773)

#2 (884-902):
GCUGCAUUCUGGCAGAAAUUU      (SEQ ID NO: 774)

#3 (357-375):
GUGCUCUGCUUAUGAUAAUUU      (SEQ ID NO: 775)

mm (1178-1196):
CCUCGUCAUAAUACUGGGUUU      (SEQ ID NO: 776)
```

The siRNAs were expressed from the rAAV vector. Thus, to generate the siRNA #1, the DNA sequence of the sense strand GCAGGAGCTTGTGGAAATATT (SEQ ID NO:777) was linked to a spacer derived from an miRNA (TTCAAGAGA; SEQ ID NO:766) at the 3' end, which was then linked to the corresponding antisense sequence (AATATTTCCACAAGCTCCTGC (SEQ ID NO:778)). Thus, the non-template strand sequence used in the expression cassette for the GCAGGAGCTTGTGGAAATATT (SEQ ID NO:777) siRNA will have the following sequence (SEQ ID NO:779)): GCAGGAGCTTGTGGAAATATT-TTCAAGAGA-AATATTTCCACAAGCTCCTGC. This sequence was placed downstream of an RNA polymerase III (RNA pol III) promoter in the rAAV vector. The vector also contained 6 consecutive dTs in the non-template strand following the SEQ ID NO:779 sequence to stop the transcription.

To generate the siRNA #2, the 3' end of the DNA sequence of the sense strand GCTGCATTCTGGCAGAAATTT (SEQ ID NO:780) was linked to the TTCAAGAGA (SEQ ID NO:766) spacer which was then linked to the corresponding antisense sequence AAATTTCTGCCAGAATGCAGC (SEQ ID NO:781) to form the following shRNA sequence (SEQ ID NO:782): GCTGCATTCTGGCAGAAATTT-TTCAAGAGA-AAATTTCTGCCAGAATGCAGC.

To generate the siRNA#3, the 3' end of the DNA sequence of the sense strand GTGCTCTGCTTATGATAATTT (SEQ ID NO:783) was linked to the TTCAAGAGA (SEQ ID NO:766) spacer which was then linked to the corresponding antisense sequence AAATTATCATAAGCAGAGCAC (SEQ ID NO:784) to form the following shRNA sequence (SEQ ID NO:785): GTGCTCTGCTTATGATAATTT-TTCAAGAGA-AAATTATCATAAGCAGAGCAC.

Note that other spacer sequences can be used instead of the TTCAAGAGA (SEQ ID NO:766) spacer. For example, the following spacer can be used: CTTCCTGTCA (SEQ ID NO:786)

Figure 11A:
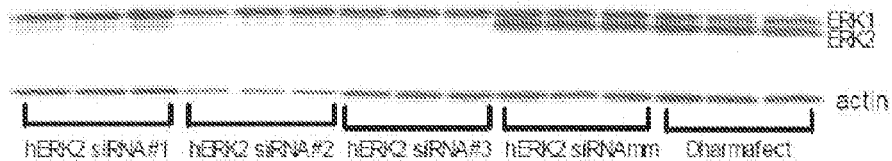
FIG. 11A-B illustrate that siRNAs directed against human ERK2 dramatically reduce expression of human ERK2 in cultured human embryonic kidney (HEK293) cells.

As shown in FIG. 11A, each of the human ERK2 siRNAs significantly reduced ERK2 expression without significantly changing ERK1 expression, as detected by Western blot analysis of ERK1 and ERK2 protein levels in the transfected cells.

Figure 11B:
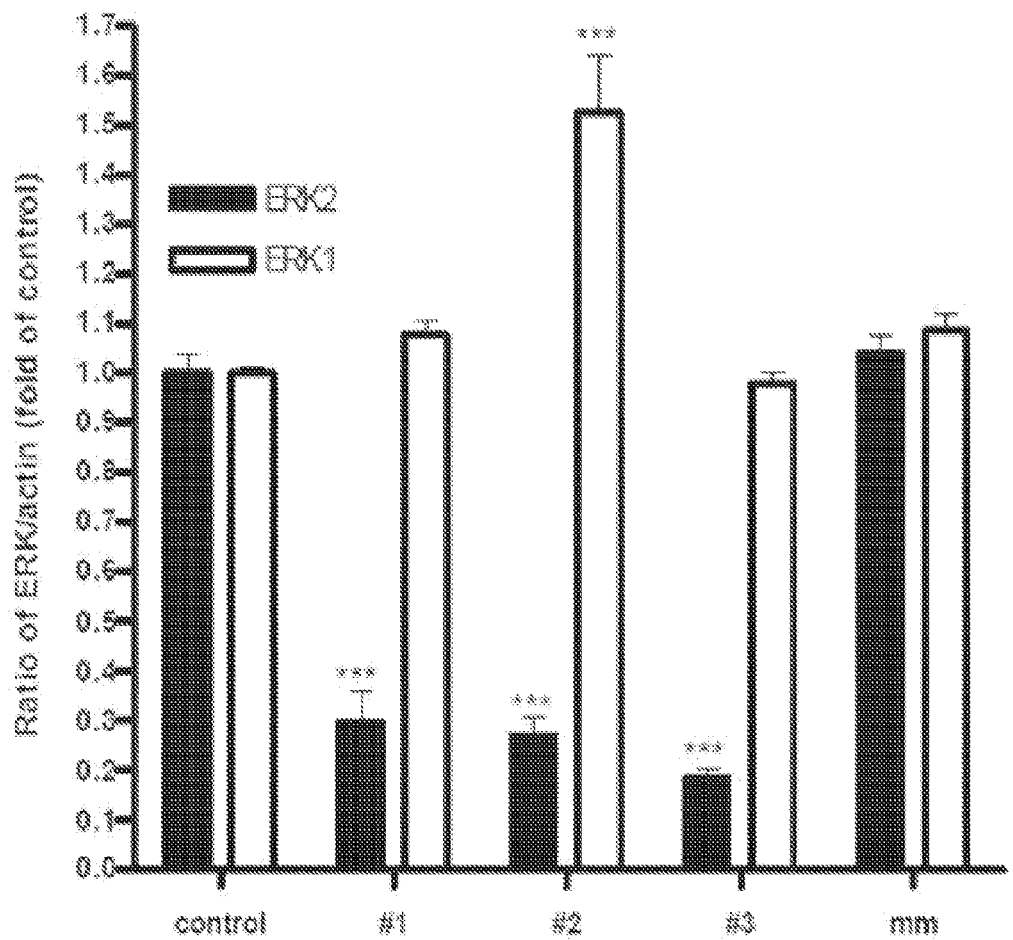
Figure 12A:
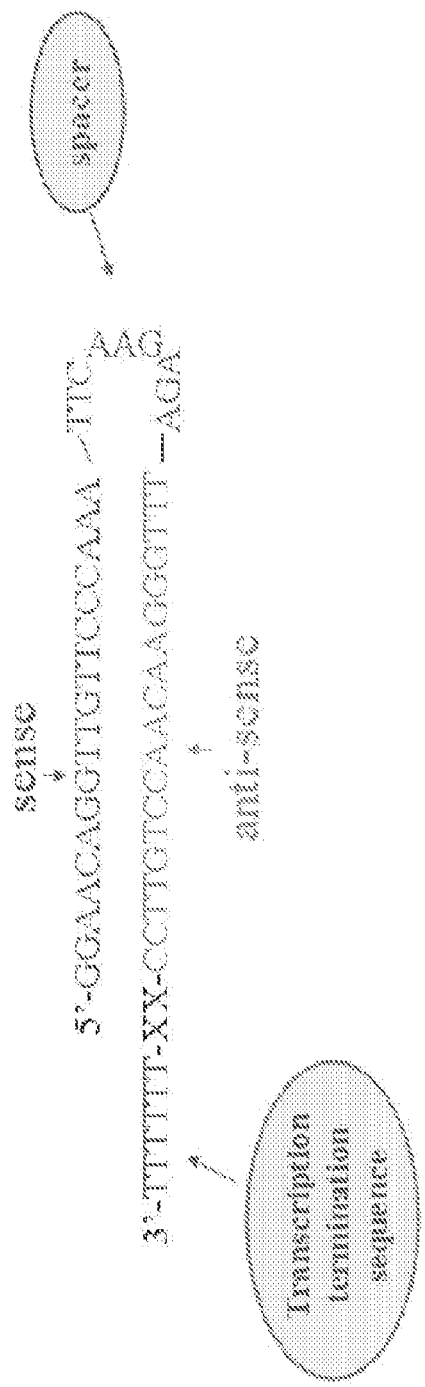
FIG. 12A-B illustrates the construction of nucleic acids that encode an shRNA.
Figure 12B:
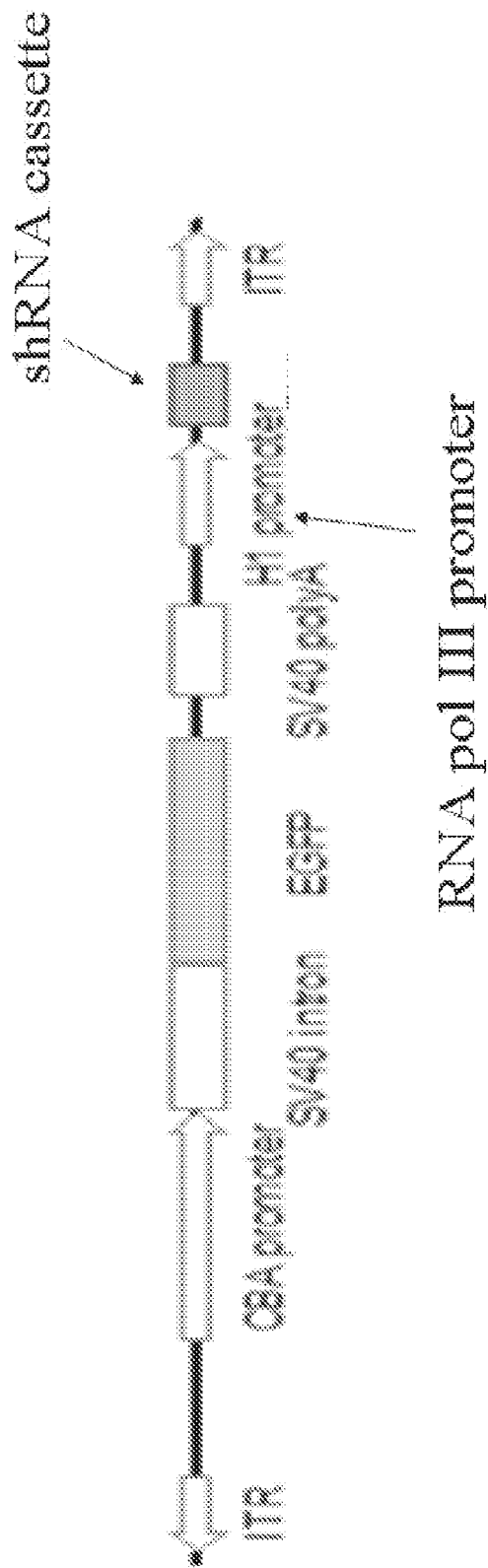

FIG. 11B graphically illustrates the reduction of ERK2 expression by each of the human ERK2 siRNAs. As shown, each of human ERK2 siRNAs #1 (SEQ ID NO:773), #2 (SEQ ID NO:774) and #3 (SEQ ID NO:775) reduced human ERK2 expression by about 70-80%.

REFERENCES

Adwanikar H, Karim F, Gereau R W 4th (2004) Inflammation persistently enhances nocifensive behaviors mediated by spinal group I mGluRs through sustained ERK activation. Pain 111:125-135.

Boulton T G, Nye S H, Robbins D J, Ip N Y, Radziejewska E, Morgenbesser S D, DePinho R A, Panayotatos N, Cobb M H, Yancopoulos G D (1991) ERKs: a family of protein-serine/threonine kinases that are activated and tyrosine phosphorylated in response to insulin and NGF. Cell 65:663-675.

Bridge A J, Pebernard S, Ducraux A, Nicoulaz A L, Iggo R (2003) Induction of an interferon response by RNAi vectors in mammalian cells. Nat Genet. 34:263-264.

Brummelkamp T R, Bernards R, Agami R (2002) A system for stable expression of short interfering RNAs in mammalian cells. Science 296:550-553.

Chaplan S R, Bach F W, Pogrel J W, Chung J M, Yaksh T L (1994) Quantitative assessment of tactile allodynia in the rat paw. J Neurosci Methods 53:55-63.

Cheng H T, Suzuki M, Hegarty D M, Xu Q, Weyerbacher A R, South S M, Ohata M, Inturrisi C E (2008) Inflammatory pain-induced signaling events following a conditional deletion of the N-methyl-D-aspartate receptor in spinal cord dorsal horn. Neuroscience 155:948-958.

Cruz C D, Neto F L, Castro-Lopes J, McMahon S B, Cruz F (2005) Inhibition of ERK phosphorylation decreases nociceptive behaviour in monoarthritic rats. Pain 116:411-419.

Dai Y, Fukuoka T, Wang H, Yamanaka H, Obata K, Tokunaga A, Noguchi K (2004) Contribution of sensitized P2X receptors in inflamed tissue to the mechanical hypersensitivity revealed by phosphorylated ERK in DRG neurons. Pain 108:258-266.

English J D, Sweatt J D (1996) Activation of p42 mitogen-activated protein kinase in hippocampal long term potentiation. J Biol Chem 271:24329-24332. Fre'min C, Ezan F, Boisselier P, Bessard A, Page's G, Pouysse'gur J, Baffet G (2007) ERK2 but not ERK1 plays a key role in hepatocyte replication: an RNAi-mediated ERK2 knockdown approach in wild-type and ERK1 null hepatocytes. Hepatology 45:1035-1045.

Galan A, Lopez-Garcia J A, Cervero F, Laird J M (2002) Activation of spinal extracellular signaling-regulated kinase-1 and -2 by intraplantar carrageenan in rodents. Neurosci Lett 322:37-40.

Garraway S M, Xu Q, Inturrisi C E (2007) Design and evaluation of small interfering RNAs that target expression of the N-methyl-D-aspartate receptor NR1 subunit gene in the spinal cord dorsal horn. J Pharmacol Exp Ther 322: 982-988.

Guo W, Wang H, Watanabe M, Shimizu K, Zou S, LaGraize S C, Wei F, Dubner R, Ren K (2007) Glial-cytokine-neuronal interactions underlying the mechanisms of persistent pain. J Neurosci 27:6006-6018.

Hanks S K, Hunter T (1995) Protein kinases 6. The eukaryotic protein kinase superfamily: kinase (catalytic) domain structure and classification. FASEB J 9:576-596.

Hargreaves K, Dubner R. Brown F, Flores C, Joris J (1988) A new and sensitive method for measuring thermal nociception in cutaneous hyperalgesia. Pain 32:77-88.

Hatano N, Mori Y, Oh-hora M, Kosugi A, Fujikawa T, Nakai N, Niwa H, Miyazaki J, Hamaoka T, Ogata M (2003) Essential role for ERK2 mitogen-activated protein kinase in placental development. Genes Cells 8:847-856.

Hu H J, Carrasquillo Y, Karim F, Jung W E, Nerbonne J M, Schwarz T L, Gereau R W 4th (2006) The kv4.2 potassium channel subunit is required for pain plasticity. Neuron 50:89-100.

Ji R R, Baba H, Brenner G J, Woolf C J (1999) Nociceptive-specific activation of ERK in spinal neurons contributes to pain hypersensitivity. Nat Neurosci 2:1114-1119.

Ji R R, Befort K, Brenner G J, Woolf C J (2002) ERK MAP kinase activation in superficial spinal cord neurons induces prodynorphin and NK-1 upregulation and contributes to persistent inflammatory pain hypersensitivity. J Neurosci 22:478-485.

Karim F, Hu H J, Adwanikar H, Kaplan D, Gereau R W 4th (2006) Impaired inflammatory pain and thermal hyperalgesia in mice expressing neuronspecific dominant negative mitogen activated protein kinase kinase (MEK). Mol Pain 2:2.

Kaspar B K, Vissel B, Bengoechea T, Crone S, Randolph-Moore L, Muller R, Brandon E P, Schaffer D, Verma I M, Lee K F, Heinemann S F, Gage F H (2002) Adeno-associated virus effectively mediates conditional gene modification in the brain. Proc Natl Acad Sci USA 99:2320-2325.

Kawasaki Y, Kohno T, Zhuang Z Y, Brenner G J, Wang H, Van Der Meer C, Befort K, Woolf C J, Ji R R (2004) Ionotropic and metabotropic receptors, protein kinase A, protein kinase C, and Src contribute to C-fiber-induced ERK activation and cAMP response element-binding protein phosphorylation in dorsal horn neurons, leading to central sensitization. J Neurosci 24:8310-8321.

Krapivinsky G, Krapivinsky L, Manasian Y, Ivanov A, Tyzio R, Pellegrino C, Ben-Ari Y, Clapham D E, Medina I (2003) The NMDA receptor is coupled to the ERK pathway by a direct interaction between NR2B and Ras-GRF 1. Neuron 40:775-784.

Li J, Johnson S E (2006) ERK2 is required for efficient terminal differentiation of skeletal myoblasts. Biochem Biophys Res Commun 345:1425-1433.

Li X, Lighthall G, Liang D Y, Clark J D (2004) Alterations in spinal cord gene expression after hindpaw formalin injection. J Neurosci Res 78:533-541.

Musatov S, Roberts J, Pfaff D, Kaplitt M (2002) A cis-acting element that directs circular adeno-associated virus replication and packaging. J Virol 76:12792-12802.

Obata K, Yamanaka H, Dai Y, Tachibana T, Fukuoka T, Tokunaga A, Yoshikawa H, Noguchi K (2003) Differential activation of extracellular signal-regulated protein kinase in primary afferent neurons regulates brain-derived neurotrophic factor expression after peripheral inflammation and nerve injury. J Neurosci 23:4117-4126.

Page's G, Stanley E R, Le Gall M, Brunet A, Pouysse'gur J (1995) The mouse p44 mitogen-activated protein kinase (extracellular signal-regulated kinase 1) gene. Genomic organization and structure of the 5'-flanking regulatory region. J Biol Chem 270:26986-26992.

Page's G, Gue'rin S, Grall D, Bonino F, Smith A, Anjuere F, Auberger P, Pouysse'gur J (1999) Defective thymocyte maturation in p44 MAP kinase (Erk 1) knockout mice. Science 286:1374-1377.

Raghavendra V, Tanga F Y, DeLeo J A (2004) Complete Freunds adjuvant-induced peripheral inflammation evokes glial activation and proinflammatory cytokine expression in the CNS. Eur J Neurosci 20:467-473.

Robbins D J, Zhen E, Cheng M, Xu S, Vanderbilt C A, Ebert D, Garcia C, Dang A, Cobb M H (1993) Regulation and properties of extracellular signal-regulated protein kinases 1, 2, and 3. J Am Soc Nephrol 4:1104-1110.

Saba-El-Leil M K, Vella F D, Vernay B, Voisin L, Chen L, Labrecque N, Ang S L, Meloche S (2003) An essential function of the mitogen-activated protein kinase Erk2 in mouse trophoblast development. EMBO Rep 4:964-968.

Sledz C A, Holko M, de Veer M J, Silverman R H, Williams B R (2003) Activation of the interferon system by short-interfering RNAs. Nat Cell Biol 5:834-839.

South S M, Kohno T, Kaspar B K, Hegarty D, Vissel B, Drake C T, Ohata M, Jenab S, Sailer A W, Malkmus S, Masuyama T, Horner P, Bogulaysky J, Gage F H, Yaksh T L, Woolf C J, Heinemann S F, Inturrisi C E (2003) A conditional deletion of the NR1 subunit of the NMDA receptor in adult spinal cord dorsal horn reduces NMDA currents and injury-induced pain. J Neurosci 23:5031-5040.

Sugiura N, Suga T, Ozeki Y, Mamiya G, Takishima K (1997) The mouse extracellular signal-regulated kinase 2 gene. Gene structure and characterization of the promoter. J Biol Chem 272:21575-21581.

Svensson C I, Tran T K, Fitzsimmons B, Yaksh T L, Hua X Y (2006) Descending serotonergic facilitation of spinal ERK activation and pain behavior. FEBS Lett 580:6629-6634.

Tseng T J, Hsieh Y L, Hsieh S T (2007) Reversal of ERK activation in the dorsal horn after decompression in chronic constriction injury. Exp Neurol 206:17-23.

Wang H, Dai Y, Fukuoka T, Yamanaka H, Obata K, Tokunaga A, Noguchi K (2004) Enhancement of stimulation-induced ERK activation in the spinal dorsal horn and gracile nucleus neurons in rats with peripheral nerve injury. Eur J Neurosci 19:884-890.

Yao Y, Li W, Wu J, Germann U A, Su M S, Kuida K, Boucher D M (2003) Extracellular signal-regulated kinase 2 is necessary for mesoderm differentiation. Proc Natl Acad Sci USA 100:12759-12764.

Yuan B, Latek R, Hossbach M, Tuschl T, Lewitter F (2004) siRNA selection server: an automated siRNA oligonucleotide prediction server. Nucleic Acids Res 32:W130-W134.

Zeng P, Wagoner H A, Pescovitz O H, Steinmetz R (2005) RNA interference (RNAi) for extracellular signal-regulated kinase 1 (ERK1) alone is sufficient to suppress cell viability in ovarian cancer cells. Cancer Biol Ther 4:961-967.

Zhao P, Waxman S G, Hains B C (2007) Extracellular signal-regulated kinase-regulated microglia-neuron signaling by prostaglandin E2 contributes to pain after spinal cord injury. J Neurosci 27:2357-2368.

Zheng C F, Guan K L (1993) Properties of MEKs, the kinases that phosphorylate and activate the extracellular signal-regulated kinases. J Biol Chem 268:23933-23939.

Zhuang Z Y, Gerner P, Woolf C J, Ji R R (2005) ERK is sequentially activated in neurons, microglia, and astrocytes by spinal nerve ligation and contributes to mechanical allodynia in this neuropathic pain model. Pain 114: 149-159.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for treating or inhibiting pain in an animal comprising administering to the animal specific inhibitor of extracellular signal-regulated kinase 2 (ERK2) to thereby treat or inhibit pain in the animal without reducing inflammation, wherein the inhibitor is a nucleic acid that can inhibit the expression of ERK2.

2. The method of claim 1, wherein the animal is a human, domesticated animal, experimental animal or a zoo animal.

3. The method of claim 1, wherein the inhibitor is administered locally.

4. The method of claim 1, wherein the nucleic acid can hybridize to an mRNA encoding a ERK2 polypeptide with SEQ ID NO: 2.

5. The method of claim 1, wherein the nucleic acid can hybridize to an ERK2 polynucleotide comprising SEQ ID NO:2 and/or SEQ ID NO:771.

6. The method of claim 1, wherein the nucleic acid is a small interfering RNA.

7. The method of claim 1, wherein the nucleic acid has a modified backbone or one or more non-natural internucleoside linkages.

8. The method of claim 1, wherein the nucleic acid is a small interfering RNA comprising a DNA or RNA sequence with any of SEQ ID NO:3-162, 166-764, 765, 769, 770, 773, 774, 775, or a combination thereof; and/or a DNA or RNA that can specifically hybridize to any of SEQ ID NO:3-162, 166-764, 765, 769, 770, 773, 774, 775, or a combination thereof.

9. The method of claim 1, wherein the nucleic acid is a small interfering RNA comprising a DNA or RNA sequence with any of SEQ ID NO: 765, 769, 770, 773, 774, 775, or a combination thereof; and/or a DNA or RNA that can specifically hybridize to any of SEQ ID NO: 765, 769, 770, 773, 774, 775, or a combination thereof.

10. The method of claim 1, wherein the nucleic acid is a small interfering RNA comprising a DNA or RNA sequence corresponding to any one SEQ ID NO: 773, 774, 775, 779, 782, 785, or a combination thereof.

11. The method of claim 1, wherein the nucleic acid is encoded within an expression cassette comprising a promoter and a polynucleotide segment comprising a DNA or RNA corresponding to any of SEQ ID NO: SEQ ID NO:3-162, 166-764, 765, 769, 770, 773-775, 779, 782, 785, or a combination thereof.

12. The method of claim 11, wherein the segment comprises X-L-Y, wherein X is a sense sequence, L is a spacer linked to the 3' end of the sense sequence, and Y is an antisense sequence linked to the 3' end of the linker, and wherein the Y antisense sequence is complementary to the X sequence so that upon expression of the polynucleotide segment, a short hairpin RNA (shRNA) is generated.

13. The method of claim 11, wherein the expression cassette is present in an expression vector.

14. The method of claim 11, wherein the expression vector is within a neurotropic recombinant adeno-associated virus (rAAV).

15. The method of claim 1, wherein administering the nucleic acid that can inhibit the expression of ERK2 does not significantly change ERK1 expression.

16. The method of claim 1, wherein the pain is neuropathic pain.

17. The method of claim 1, wherein the nucleic acid is expressed from a viral vector, which is a neurotropic recombinant adeno-associated virus vector.

18. A method for treating or inhibiting inflammatory pain in an animal comprising administering to the animal's central nervous system or spinal fluid a specific inhibitor of extracellular signal-regulated kinase 2 (ERK2) to thereby treat or inhibit pain in the animal without reducing inflammation, wherein the inhibitor is a nucleic acid that can inhibit the expression of ERK2.

* * * * *